United States Patent
Giencke et al.

(10) Patent No.: US 6,861,389 B2
(45) Date of Patent: Mar. 1, 2005

(54) SUBSTITUTED 2-AMINO-1,3,5-TRIAZINES, THEIR PREPARATION, AND THEIR USE AS HERBICIDES AND PLANT GROWTH REGULATORS

(75) Inventors: Wolfgang Giencke, Hofheim (DE); Lothar Willms, Hofheim (DE); Thomas Auler, Bad Soden (DE); Hermann Bieringer, Eppstein (DE); Hubert Menne, Hofheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 10/262,001

(22) Filed: Oct. 1, 2002

(65) Prior Publication Data

US 2003/0204083 A1 Oct. 30, 2003

Related U.S. Application Data

(63) Continuation of application No. 09/906,932, filed on Jul. 17, 2001, now abandoned.

(30) Foreign Application Priority Data

Jul. 19, 2000 (DE) .......................................... 100 35 038

(51) Int. Cl.$^7$ .................. A01N 43/66; A01N 43/68; C07D 25/42; C07D 25/48
(52) U.S. Cl. .................. 504/230; 504/231; 504/232; 544/197; 544/198; 544/206; 544/207; 544/208; 544/209; 544/211; 544/212
(58) Field of Search .............................. 504/230, 231, 504/232; 544/197, 198, 211, 212, 206, 207, 208, 209

(56) References Cited

U.S. PATENT DOCUMENTS 6,001,382 A * 12/1999 Levy .......................... 424/405

FOREIGN PATENT DOCUMENTS

| AU | 47790/97 | 4/1998 |
|----|----------|--------|
| AU | 22786/99 | 8/1999 |
| WO | WO 98/15537 | 4/1998 |
| WO | WO 99/37627 | 7/1999 |

OTHER PUBLICATIONS

Bredereck, et al., "Über Säureamid–Dialkylsulfat–Komplexe," Chem. Ber., vol. 96, (1962), pp. 1350–1355.

Meerwein, et al., "Reaktionen mit Alkylkationen" Chem. Ber., vol. 89, 1956, pp. 2060–2079.

Meerwein, et al., Über Säureamidacetal, Harnstoffacetal Und Lactamacetal Liebigs Ann. Chem., vol. 641, (1961) pp. 1–39.

Lorenz, et al., "A New Indole Synthesis," J. Org. Chem., vol. 30, (1965), pp. 2531–2533.

* cited by examiner

*Primary Examiner*—Richard L. Raymond
(74) *Attorney, Agent, or Firm*—Frommer Lawrence & Haug LLP

(57) ABSTRACT

The compounds of the formula (I) and their salts

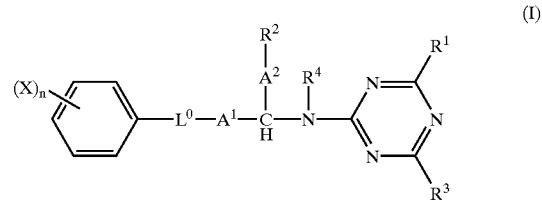

where the radicals $R^1$ to $R^4$, $A^1$, $A^2$, $L^0$, X and n are as defined in claim 1 are suitable as herbicides and plant growth regulators and can be prepared by processes as claimed in claim 6.

9 Claims, No Drawings

SUBSTITUTED 2-AMINO-1,3,5-TRIAZINES, THEIR PREPARATION, AND THEIR USE AS HERBICIDES AND PLANT GROWTH REGULATORS

This application is a continuation of Ser. No. 09/906,932, filed Jul. 17, 2001, now abandoned.

DESCRIPTION

Substituted 2-amino-1,3,5-triazines, their preparation, and their use as herbicides and plant growth regulators The invention relates to the technical field of the crop protection agents, such as herbicides and plant growth regulators, in particular of the herbicides for selectively controlling harmful plants in crops of useful plants.

It is known that 2-amino-4-(N-phenylalkylamino)-1,3,5-triazines which are substituted in the 6-position and which can be further substituted have herbicidal and plant-growth-regulatory properties; cf. WO 97/08156 and literature cited therein, WO 99/37627 and literature cited therein, WO 98/15537 and literature cited therein; cf. to some extent also WO 97/00254 and literature cited therein.

In some cases, the known active substances have disadvantages when used, be it an insufficient herbicidal action against harmful plants, too narrow a weed plant spectrum which can be controlled with an active substance, or too little selectivity in crops of useful plants. Other active substances cannot be prepared economically on an industrial scale, owing to precursors and reagents which are not easily available; in the case of others, the chemical stability is insufficient.

The object of the present invention is to provide alternative active substances of the 2-amino-1,3,5-triazine type which can be employed as herbicides or plant-growth regulators, if appropriate advantageously.

Subject matter of the present invention are compounds of the formula (I) and their salts

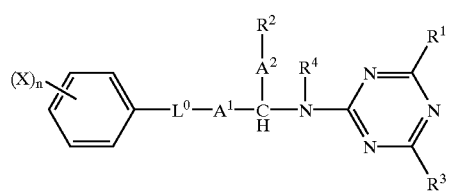

(I)

in which $R^1$ is aryl, aryloxy, arylthio, arylamino, N-aryl-N-$(C_1-C_4)$alkylamino, $(C_3-C_9)$cycloalkyl, $(C_3-C_9)$cycloalkyloxy, $(C_3-C_9)$cycloalkylthio, $(C_3-C_9)$cycloalkylamino, N-$(C_3-C_9)$cycloalkyl-N-$(C_1-C_4)$alkylamino, di-[$(C_3-C_9)$cycloalkyl]amino, heterocyclyl, heterocyclyloxy, heterocyclylthio, heterocyclylamino or N-heterocyclyl-N-$(C_1-C_4)$alkylamino, where each of the last-mentioned 16 radicals is unsubstituted or substituted, preferably unsubstituted or substituted by one or more radicals selected from the group consisting of halogen, hydroxyl, amino, nitro, formyl, carboxyl, sulfo, cyano, thiocyanato, $(C_1-C_6)$alkyl, $(C_1-C_6)$haloalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy, $(C_1-C_6)$haloalkoxy, $(C_2-C_6)$alkenyloxy, $(C_2-C_6)$haloalkenyloxy, $(C_2-C_6)$alkynyloxy, $(C_2-C_6)$haloalkynyoxy, $(C_1-C_6)$alkylthio, $(C_1-C_6)$haloalkylthio, mono$(C_1-C_6)$alkylamino, di$(C_1-C_6)$alkylamino, $(C_3-C_9)$cycloalkyl, $(C_5-C_9)$cycloalkenyl, [$(C_1-C_5)$alkyl]carbonyl, [$(C_1-C_6)$alkoxy]carbonyl, aminocarbonyl, mono$(C_1-C_6)$alkylaminocarbonyl, di$(C_1-C_6)$alkylaminocarbonyl, $(C_1-C_6)$alkylsulfonyl and $(C_1-C_6)$haloalkylsulfonyl, and, inclusive of substituents, preferably has up to 30 carbon atoms, or is hydrogen, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkylthio, $(C_2-C_6)$alkenylthio, $(C_2-C_6)$alkynylthio, $(C_1-C_6)$alkylamino or di-[$(C_1-C_6)$alkyl]amino, where each of the last-mentioned 11 radicals can be unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, preferably, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted, and where Z and Z' independently of one another are in each case an oxygen or sulfur atom, and, inclusive of substituents, preferably has 1 to 30 carbon atoms, $R^2$ is $(C_3-C_9)$cycloalkyl which is unsubstituted or substituted, $(C_4-C_9)$cycloalkenyl which is unsubstituted or substituted, heterocyclyl which is unsubstituted or substituted, or phenyl which is unsubstituted or substituted, where $R^2$, inclusive of substituents, preferably has up to 30 carbon atoms, $R^3$ is a group

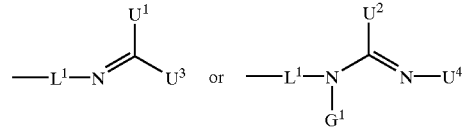

in which $L^1$ is a direct bond, —O—, —S— or a group of the formula —NG$^2$—, preferably a direct bond, $U^1$, $U^2$ independently of one another are a group of the formula $G^3$, $OG^4$, $SG^5$, $NG^6G^7$, $NG^8NG^9G^{10}$, $NG^{11}OG^{12}$ or $NG^{11}SG^{12}$, $U^3$ is a group of the formula $G^{13}$, $OG^{14}$, $SG^{15}$, $NG^{16}G^{17}$, $NG^{18}NG^{19}G^{20}$, $NG^{21}OG^{22}$ or $NG^{23}SG^{24}$, $U^4$ is a group of the formula $G^{25}$, $OG^{26}$, $SG^{27}$ or $NG^{28}G^{29}$, where the radicals $G^1$ to $G^{29}$ independently of one another are hydrogen, aryl which is unsubstituted or substituted and, inclusive of substituents, preferably has 6 to 30 carbon atoms, or $(C_3-C_9)$cycloalkyl which is unsubstituted or substituted and, inclusive of substituents, preferably has 3 to 30 carbon atoms, or heterocyclyl which is substituted or unsubstituted and, inclusive of substituents, preferably has 2 to 30 carbon atoms, or are $(C_1-C_6)$alkyl, $(C_2-C_6)$alkenyl or $(C_2-C_6)$alkynyl, where each of the last-mentioned 3 radicals is unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, preferably, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and where Z and Z' independently of one another are in each case an oxygen or sulfur atom, and, inclusive of substituents, preferably has 1 to 30 carbon atoms, or the radicals $U^1$ and $U^3$ or $U^2$ and $U^4$ or $U^2$ and $G^1$ or $U^4$ and $G^1$, as a pair, together with the atoms linking them are in each case a carbocyclic or heterocyclic ring having 4 to 7 ring atoms, the ring being unsubstituted or substituted, $R^4$ is a radical of the formula —$B^1$-$D^1$, where $B^1$ and $D^1$ are as defined hereinbelow, and $R^4$, inclusive of substituents, preferably has up to 20 carbon atoms, $A^1$ is a direct bond or straight-chain alkylene having 1 to 5 carbon atoms or straight-chain alkenylene or alkynylene having in each case 2 to 5 carbon atoms, where each of the three last-mentioned diradicals is unsubstituted or substituted by one or more radicals selected from the group consisting of halogen, nitro, cyano, thiocyanato and radicals of the formula —$B^2$-$D^2$, where $B^2$ and $D^2$ are as defined hereinbelow, $A^2$ is a direct bond or straight-chain alkylene having 1 to 4 carbon atoms or straight-chain alkenylene or alkynylene having in each case 2 to 5 carbon atoms, where each of the three last-mentioned diradicals is unsubstituted or substituted by one or more radicals selected from the group consisting of halogen, nitro, cyano, thiocyanato and radicals of the formula —$B^3$-$D^3$, or a divalent radical of the formula $V^1$, $V^2$, $V^3$, $V^4$ or $V^5$, —CR$^a$R$^b$—W*—CR$^c$R$^d$—  (V$^1$)

—CR$^a$R$^b$—W*—CR$^c$R$^d$—CR$^e$R$^f$—  (V$^2$)

—CR$^a$R$^b$—CR$^c$R$^d$—W*—CR$^e$R$^f$—  (V$^3$)

—CR$^a$R$^b$—CR$^c$R$^d$W*—  (V$^4$)

—CR$^a$R$^b$—W*—  (V$^5$), where each of the radicals $R^a$, $R^b$, $R^c$, $R^d$, $R^e$ and $R^f$ in each case independently of one another is hydrogen, halogen, nitro, cyano, thiocyanato or a radical of the formula —$B^4$-$D^4$, W* is in each case an oxygen atom, a sulfur atom or a group of the formula N($B^5$-$D^5$) and $B^3$, $B^4$, $B^5$, $D^3$, $D^4$ and $D^5$ are as defined hereinbelow, $B^1$ and $B^5$ in each case independently of one another are a direct bond or a divalent group of the formulae —C(=Z*)—, —C(=Z*)—Z**—, —C(=Z*)—NH— or —C(=Z*)—NR*—, where Z*=an oxygen or sulfur atom, Z**=an oxygen or sulfur atom and R*=$(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and, inclusive of substituents, preferably has up to 20 carbon atoms, $B^2$, $B^3$ and $B^4$ in each case independently of one another are a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —NR$^O$—, —O—NR$^O$—, —NR$^O$—O—, —NR$^O$—CO—, —CO—NR$^O$—, —O—CO—NR$^O$— or —NR$^O$—CO—O—, where p is the integer 0, 1 or 2 and $R^O$ is hydrogen, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and, inclusive of substituents, preferably has up to 20 carbon atoms, $D^1$, $D^2$, $D^3$, $D^4$ and $D^5$ in each case independently of one another are hydrogen, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and, inclusive of substituents, preferably has up to 20 carbon atoms, or in each case two radicals $D^3$ of two groups —b$_3$-$D^3$ bound to one carbon atom are linked to each other and form an alkylene group having 2 to 4 carbon atoms which is unsubstituted or substituted by one or more radicals selected from the group consisting of $(C_1-C_4)$alkyl and $(C_1-C_4)$alkoxy, $L^O$ is a direct bond, oxygen, sulfur or a group NG$^{30}$ in which the radical $G^{30}$ is hydrogen, aryl which is unsubstituted or substituted and, inclusive of substituents, preferably has 6 to 30 carbon atoms, or $(C_3-C_9)$cycloalkyl which is unsubstituted or substituted and, inclusive of substituents, preferably has 3 to 30 carbon atoms, or heterocyclyl which is substituted or unsubstituted and, inclusive of substituents, preferably has 2 to 30 carbon atoms, or is $(C_1-C_6)$alkyl, $(C_2-C_6)$alkenyl or $(C_2-C_6)$alkynyl, where each of the last-mentioned 3 radicals is unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, preferably, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and where Z and Z' independently of one another are in each case an oxygen or sulfur atom, and, inclusive of substituents, preferably has 1 to 30 carbon atoms, $(X)_n$ is n substituents X, where the X in each case independently of one another are halogen, hydroxyl, amino, nitro, formyl, carboxyl, cyano, thiocyanato, aminocarbonyl or $(C_1-C_6)$alkyl, $(C_1-C_6)$alkoxy, $(C_1-C_6)$alkylthio, mono $(C_1-C_6)$alkylamino, di$(C_1-C_4)$alkylamino, $(C_2-C_6)$ alkenyl, $(C_2-C_6)$alkynyl, $[(C_1-C_6)$alkyl]carbonyl, $[(C_1-C_6)$alkoxy]carbonyl, mono$(C_1-C_6)$ alkylaminocarbonyl, di$(C_1-C_4)$alkylaminocarbonyl, N—$(C_1-C_6)$alkanoylamino or N—$(C_1-C_4)$alkanoyl-N—$(C_1-C_4)$alkylamino, where each of the last-mentioned 13 radicals is unsubstituted or substituted, preferably unsubstituted or substituted by one or more radicals selected from the group consisting of halogen, hydroxyl, amino, nitro, formyl, carboxyl, cyano, thiocyanato, $(C_1-C_4)$alkoxy, $(C_1-C_4)$ haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $(C_3-C_9)$cycloalkylamino, $[(C_1-C_4)$ alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, where each of the last-mentioned 8 radicals is unsubstituted or has one or more substituents selected from the group consisting of halogen, nitro, cyano, $(C_1-C_4)$ alkyl, $(C_1-C_4)$alkoxy, $(C_1-C_4)$alkylthio, $(C_1-C_4)$ haloalkyl, $(C_1-C_4)$haloalkoxy, formyl, $(C_1-C_4)$ alkylcarbonyl and $(C_1-C_4)$alkoxycarbonyl, or is $(C_3-C_9)$cycloalkyl, $(C_3-C_9)$cycloalkoxy, $(C_3-C_9)$ cycloalkylamino, phenyl, phenoxy, phenylthio, phenylcarbonyl, heterocyclyl, heterocyclyloxy, heterocyclylthio or heterocyclylamino, where each of the last-mentioned 11 radicals is unsubstituted or substituted, preferably unsubstituted or substituted by one or more radicals selected from the group consisting of halogen, hydroxyl, amino, nitro, formyl, carboxyl, cyano, thiocyanato, $(C_1-C_4)$alkyl, $(C_1-C_4)$haloalkyl, $(C_1-C_4)$alkoxy, $(C_1-C_4)$ haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono $(C_1-C_4)$alkylaminocarbonyl and Di$(C_1-C_4)$ alkylaminocarbonyl, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$alkyl and oxo, n is 0, 1, 2, 3, 4 or 5, preferably 0, 1, 2, 3 or 4, in particular 0, 1 or 2, and heterocyclyl in the abovementioned radicals independently of one another in each case is a heterocyclic radical having 3 to 7 ring atoms and 1 to 3 hetero atoms selected from the group consisting of N, O and S.

Unless specified in greater detail, divalent radicals, for example $B^1$=—C(=$Z^*$)—$Z^{**}$—, are defined such that, in the composite groups, for example —$B^1$-$D^1$, it is the bond of the divalent radical that is written on the right in the formula for the divalent radical which is linked to the group $D^1$, i.e. —$B^1$-$D^1$ is a group of the formula —C(=$Z^*$)—$Z^{**}$-$D^1$; this applies similarly to analogous divalent radicals.

The compounds of the formula (I) can form salts by addition of a suitable inorganic or organic acid such as, for example, HCl, HBr, $H_2SO_4$ or $HNO_3$, but also oxalic acid or sulfonic acids, to a basic group such as, for example, amino or alkylamino. Suitable substituents which are present in deprotonated form such as, for example, sulfonic acids or carboxylic acids, can form internal salts with groups which are protonable themselves, such as amino groups. Likewise, salts can be formed by replacing the hydrogen in suitable substituents such as, for example, sulfonic acids or carboxylic acids, by an agriculturally suitable cation. These salts are, for example, metal salts, in particular alkali metal salts or alkaline earth metal salts, in particular sodium salts and potassium salts, or else ammonium salts, salts with organic amines, or quaternary ammonium salts.

In formula (I) and all subsequent formulae, the radicals alkyl, alkoxy, haloalkyl, haloalkoxy, alkylamino and alkylthio and the corresponding unsaturated and/or substituted radicals can be in each case straight-chain or branched in the carbon skeleton. Unless specifically indicated, the lower carbon skeletons, for example those having 1 to 6 carbon atoms or, in the case of unsaturated groups, 2 to 6 carbon atoms, are preferred for these radicals. Alkyl radicals, also in the composite meanings such as alkoxy, haloalkyl and the like, are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meanings of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Cycloalkyl is a carbocyclic, saturated ring system having preferably 3–8 carbon atoms, for example cyclopropyl, cyclobutyl, cyclopentyl or cyclohexyl. In the case of substituted cycloalkyl, this encompasses cyclic systems with substituents, where the substituents are bonded to the cycloalkyl radical by a double bond, for example, an alkylidene group such as methylidene. In the case of substituted cycloalkyl, this also encompasses polycyclic aliphatic systems such as, for example, bicyclo[1.1.0]butan-1-yl, bicyclo [1.1.0]butan-2-yl, bicyclo[2.1.0]pentan-1-yl, bicyclo[2.1.0] pentan-2-yl, bicyclo[2.1.0]pentan-5-yl, adamantan-1-yl and adamantan-2-yl.

Cycloalkenyl is a carbocyclic, nonaromatic, partially unsaturated ring system having preferably 4–8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, what has been said for substituted cycloalkyl applies analogously.

Halogen is, for example, fluorine, chlorine, bromine or iodine. Haloalkyl, -alkenyl and -alkynyl are alkyl, alkenyl or alkynyl, respectively, each of which is partially or fully substituted by, preferably, fluorine, chlorine and/or bromine, in particular by fluorine or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic; it preferably contains one or more, in particular 1, 2 or 3, hetero atoms in the heterocyclic ring, preferably selected from the group consisting of N, O and S; it is preferably an aliphatic heterocyclyl radical having 3 to 7 ring atoms or a heteroaromatic radical having 5 or 6 ring atoms. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, or it is a partially or fully hydrogenated radical such as oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl. Suitable substituents for a substituted heterocyclic radical are the substituents stated further below, and additionally also oxo. The oxo group can also be present at those hetero ring atoms where various oxidation numbers are possible, for example in the case of N and S.

Substituted radicals such as a substituted alkyl, alkenyl, alkynyl, aryl, phenyl, benzyl, heterocyclyl and heteroaryl radical are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl.

In this context, "one or more radicals selected from the group consisting of" in the definition are to be understood as meaning in each case one or more identical or different radicals selected from the stated group of radicals, unless specific limitations are defined expressly.

The term "substituted radicals" such as substituted alkyl and the like includes, in addition to the saturated hydrocarbon-containing radicals stated, corresponding unsaturated aliphatic and aromatic radicals such as unsubstituted or substituted alkenyl, alkynyl, alkenyloxy, alkynyloxy, phenyl, phenoxy and the like, as substituents. In the case of substituted cyclic radicals with aliphatic moieties in the ring, this also encompasses cyclic systems with those substituents which are bonded to the ring by a double bond, for example which are substituted by an alkylidene group such as methylidene or ethylidene.

In the case of radicals with carbon atoms, those having 1 to 4 carbon atoms, in particular 1 or 2 carbon atoms, are preferred. Substituents which are preferred are, as a rule, those selected from the group consisting of halogen, e.g. fluorine and chlorine, $(C_1-C_4)$alkyl, preferably methyl or ethyl, $(C_1-C_4)$haloalkyl, preferably trifluoromethyl, $(C_1-C_4)$ alkoxy, preferably methoxy or ethoxy, $(C_1-C_4)$haloalkoxy, nitro and cyano. Especially preferred in this context are the substituents methyl, methoxy and chlorine.

Mono- or disubstituted amino is a chemically stable radical selected from the group consisting of substituted amino radicals which are N-substituted by, for example, one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred in this context are alkyl radicals having 1 to 4 carbon atoms; aryl is preferably phenyl or substituted phenyl in this context; acyl is as defined further below, preferably $(C_1-C_4)$alkanoyl. This also applies analogously to substituted hydroxylamino or hydrazino.

Unsubstituted or substituted phenyl is preferably phenyl which is unsubstituted or mono- or polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is, in a broad sense, the radical of an organic acid which is formed formally by removing an OH group, for example the radical of a carboxylic acid and radicals of acids derived therefrom, such as thiocarboxylic acid, unsubstituted or N-substituted iminocarboxylic acids or the radical of carbonic monoesters, unsubstituted or N-substituted carbamic acid, sulfonic acids, sulfinic acids, phosphonic acids, and phosphinic acids. Acyl is, for example, formyl, alkylcarbonyl such as $[(C_1-C_4)$alkyl$]$ carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. In this context, the radicals can be even further substituted in each of the alkyl or phenyl moieties, for example in the alkyl moiety by one or more radicals selected from the group consisting of halogen, alkoxy, phenyl and phenoxy; examples of substituents in the phenyl moiety are the substituents which have already been mentioned further above in general for substituted phenyl. Acyl in the narrower sense is, for example, the radical of an alkanoic acid, alkenoic acid, alkynoic acid, arylcarboxylic acid (for example benzoyl), alkoxycarbonyl, alkenyloxycarbonyl, alkynyloxycarbonyl, aryloxycarbonyl, alkylsulfonyl or alkysulfinyl; in an even narrower sense, acyl is a radical of an alkanoic acid, for example a $(C_1-C_{24})$ alkanoic acid, preferably $(C_1-C_{18})$alkanoic acid, in particular $(C_1-C_{12})$alkanoic acid, very especially $(C_1-C_6)$alkanoic acid such as formyl, acetyl or propionyl.

By combination of variables the generic formulae may formally define instable functional groups, e.g. the carbamyl radical or the hydroxy carbonyloxy radical, which are instable in neutral or acidic aqueous medium and which thus are not preferred or are used by way of their stable salts or degradation products only, respectively.

Subject matter of the invention are all stereoisomers which are encompassed by formula (I), and their mixtures. Such compounds of the formula (I) contain one or more asymmetric carbon atoms or else double bonds which are not stated specifically in the formula (I). The possible stereoisomers which are defined by their specific spatial form, such as enantiomers, diastereomers, Z- and E-isomers, are all encompassed by formula (I) and can be obtained by customary methods from mixtures of the stereoisomers, or else be prepared by stereoselective reactions in combination with the use of stereochemically pure starting materials.

Compounds of the stated formula (I) according to the invention or their salts in which individual radicals have one of the preferred meanings which have already been stated or are stated hereinbelow, or in particular those in which one or more of the preferred meanings which have already been stated or which are stated hereinbelow are combined, are of particular interest, mainly because of the more potent herbicidal action, better selectivity and/or greater ease of preparation.

$R^1$ is preferably phenyl, phenoxy, phenylthio, phenylamino, N-phenyl-N—$(C_1-C_4)$alkylamino, where each of the last-mentioned 5 radicals is unsubstituted or substituted by one or more radicals selected from the group consisting of halogen, hydroxyl, amino, nitro, formyl, carboxyl, sulfo, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl and, inclusive of substituents, has 6 to 30 carbon atoms, preferably 6 to 20 carbon atoms, in particular 6 to 15 carbon atoms. In this context, $R^1$ is, in particular, phenyl which is unsubstituted or substituted.

$R^1$ is preferably also $(C_3-C_9)$cycloalkyl which is unsubstituted or substituted by one or more radicals selected from the group consisting of halogen, hydroxyl, amino, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino and di$(C_1-C_4)$alkylamino and, inclusive of substituents, has 3 to 30 carbon atoms, preferably 3 to 20 carbon atoms, in particular 3 to 15 carbon atoms. In this context, $R^1$ is, in particular, $(C_3-C_6)$cycloalkyl which is unsubstituted or substituted.

$R^1$ is preferably also heterocyclyl which is unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl and, inclusive of substituents, has 2 to 30 carbon atoms, preferably 2 to 20 carbon atoms, in particular 2 to 15 carbon atoms.

In this context, and also in other radicals, heterocyclyl is as defined further above in general terms or by preference.

In particular, heterocyclyl preferably is, in this context, a heterocyclic radical having 3 to 7, in particular 3 to 6, ring atoms and one hetero atom selected from the group consisting of N, O and S, for example pyridyl, thienyl, furyl, pyrrolyl, oxiranyl, oxetanyl, oxolanyl (=tetrahydrofuryl), oxanyl, pyrrolidyl, piperidyl, or is a heterocyclic radical having two or three hetero atoms selected from the group consisting of pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl, morpholinyl.

$R^1$ is preferably also hydrogen or, in particular, $(C_1-C_6)$alkyl, $(C_2-C_6)$alkenyl, $(C_2-C_6)$alkynyl, $(C_1-C_6)$alkoxy or $(C_1-C_6)$alkylthio, where each of the last-mentioned 5 radicals is unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl and $(C_3-C_6)$cycloalkyl, which is unsubstituted or substituted by one or more radicals selected from the group consisting of halogen, hydroxyl, amino, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino and di$(C_1-C_4)$alkylamino, and phenyl and heterocyclyl, where each of the two last-mentioned radicals is unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl, and radicals of the formulae R'—C(=Z')—, R'—C(=Z')—Z—, R'—Z—C(=Z')—, R'R''N—C(=Z')—, R'—Z—C(=Z')—O—, R'R''N—C(=Z')—Z—, R'—Z—C(=Z')—NR''— and R'R''N—C(=Z')—NR'''—, where R', R'' and R''' in each case independently of one another are hydrogen or, in particular, $(C_1-C_4)$alkyl, phenyl, phenyl$(C_1-C_4)$alkyl, $(C_3-C_6)$cycloalkyl or $(C_3-C_6)$cycloalkyl-$(C_1-C_4)$alkyl, where each of the 5 last-mentioned radicals is unsubstituted or substituted by one or more radicals selected from the group consisting of halogen, hydroxyl, amino, nitro, formyl, cyano, thiocyanato, $(C_1-C_4)$alkoxy, $(C_1-C_4)$alkylthio, mono$(C_1-C_4)$alkylamino, di$(C_1-C_4)$alkylamino, $(C_2-C_4)$alkenyl, $(C_2-C_4)$alkynyl, $(C_3-C_6)$cycloalkyl and, in the case of cyclic radicals, also $(C_1-C_4)$alkyl and $(C_1-C_4)$haloalkyl, and where Z and Z' independently of one another are in each case an oxygen or sulfur atom, and, inclusive of substituents, preferably has 1 to 20 carbon atoms, in particular 1 to 15 carbon atoms, $R^1$ is furthermore preferably $(C_1-C_4)$alkyl which is unsubstituted or substituted by one or more radicals selected from the group consisting of halogen, $(C_1-C_4)$alkoxy, $(C_1-C_4)$alkylthio, $(C_1-C_4)$alkylsulfonyl and $(C_3-C_9)$cycloalkyl which is unsubstituted or substituted, and phenyl which is unsubstituted or substituted by one or more radicals selected from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, amino, mono- and di$[(C_1-C_4)$alkyl]amino, $(C_1-C_4)$alkanoylamino, benzoylamino, nitro, cyano, $[(C_1-C_4)$alkyl]carbonyl, formyl, carbamoyl, mono- and di-$[(C_1-C_4)$alkyl]aminocarbonyl and $(C_1-C_4)$alkylsulfonyl, and heterocyclyl having 3 to 6 ring atoms and 1 to 3 hetero ring atoms selected from the group consisting of N, O and S, where the ring is unsubstituted or substituted by one or more radicals selected from the group consisting of halogen, $(C_1-C_4)$alkyl and oxo, or phenyl which is unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl and, inclusive of substituents, has 2 to 30 carbon atoms, preferably 2 to 20 carbon atoms, in particular 2 to 15 carbon atoms.

$R^1$ is furthermore preferably $(C_1-C_4)$alkyl, $(C_1-C_4)$haloalkyl, benzyl or $[(C_3-C_6)$cycloalkyl]-$(C_1-C_2)$alkyl, in particular $(C_1-C_4)$alkyl, $(C_1-C_4)$haloalkyl or $[(C_3-C_6)$cycloalkyl]methyl, very especially —$CH_3$, —$CH_2F$, —$CHF_2$, —$CF_3$, —$CH_2Cl$, —$CHCL_2$, —$CCl_3$, —$CH_2Br$, —$CHBr_2$, —$CH_2CH_3$, —$CH_2CH_2F$, —$CF_2CHF_2$, —$CH_2CH_2Cl$, —$CHFCH_3$, —$CHFCH_2CH_3$, —$CH_2CH_2Br$, —$CH(CH_3)_2$, —$CF(CH_3)_2$, —$C(CH_3)_2Cl$, —$CH_2CH_2CH_2F$, —$CH_2CH_2CH_2Cl$ or cyclopropylmethyl or 1-fluorocycloprop-1-yl.

Other preferred compounds (I) according to the invention are those in which $R^1$ is aryl which is unsubstituted or substituted and, inclusive of substituents, preferably has 6 to 30 carbon atoms, or $(C_3-C_9)$cycloalkyl which is unsubstituted or substituted and, inclusive of substituents, preferably has 3 to 30 carbon atoms, or heterocyclyl which is unsubstituted or substituted and, inclusive of substituents, preferably has 2 to 30 carbon atoms, or is $(C_1-C_6)$alkyl, $(C_2-C_6)$alkenyl or $(C_2-C_6)$alkynyl, where each of the last-mentioned 3 radicals is unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"'— and R'R"N—C(=Z')—NR"'—, where R', R" and R'" in each case independently of one another are $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and where Z and Z' independently of one another are in each case an oxygen or sulfur atom, and, inclusive of substituents, preferably has 1 to 30 carbon atoms, $R^1$ is preferably also phenyl which is unsubstituted or substituted by one or more radicals selected from the group consisting of halogen, hydroxyl, amino, nitro, formyl, carboxyl, sulfo, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl and, inclusive of substituents, has 6 to 30 carbon atoms, preferably 6 to 20 carbon atoms, in particular 6 to 15 carbon atoms.

Independently of the radicals $R^1$, $R^3$, $R^4$, $L^O$, $A^1$, $A^2$ and $(X)_n$ and preferably in combination with preferred meanings of one or more of these radicals, the following meanings of $R^2$ are of particular interest.

$R^2$ is preferably $(C_3-C_9)$cycloalkyl which is unsubstituted or substituted by one or more radicals selected from the group consisting of the radicals A), B), C) and D), where group A) consists of the radicals halogen, hydroxyl, amino, nitro, formyl, carboxyl, aminocarbonyl, sulfo, cyano, thiocyanato and oxo, group B) consists of the radicals $(C_1-C_6)$alkyl, $(C_1-C_6)$alkoxy, $(C_1-C_6)$alkylthio, mono$(C_1-C_6)$alkylamino, di$(C_1-C_4)$alkylamino, $(C_2-C_6)$alkenyl, $(C_2-C_6)$alkynyl, $(C_3-C_9)$cycloalkyl, $(C_4-C_9)$cycloalkenyl, $(C_1-C_6)$alkylidene, $(C_4-C_9)$cycloalkylidene, radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"'— and R'R"N—C(=Z')—NR"'—, where R', R" and R'" in each case independently of one another are hydrogen or, in particular, $(C_1-C_6)$alkyl, phenyl, phenyl-$(C_1-C_6)$alkyl, $(C_3-C_9)$cycloalkyl or $(C_3-C_9)$cycloalkyl-$(C_1-C_6)$alkyl and where Z and Z' independently of one another are in each case an oxygen or sulfur atom, group C) consists of radicals as defined for group B), but where each radical is substituted by one or more radicals selected from the group consisting of halogen, hydroxyl, amino, nitro, formyl, carboxyl, sulfo, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $(C_4-C_9)$cycloalkylene $(C_4-C_9)$cycloalkylidene, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, where each of the last-mentioned 21 radicals is unsubstituted or substituted by one or more radicals selected from the group consisting of halogen, nitro, cyano, $(C_1-C_4)$alkoxy, $(C_1-C_4)$alkylthio, $(C_1-C_4)$haloalkoxy, formyl, $(C_1-C_4)$alkylcarbonyl and $(C_1-C_4)$alkoxycarbonyl and, in the case of cyclic radicals, also $(C_1-C_4)$alkyl, $(C_1-C_4)$haloalkyl and $(C_1-C_6)$alkylidene, and, in the case of cyclic radicals, also $(C_1-C_6)$alkyl, $(C_1-C_6)$haloalkyl and $(C_1-C_6)$alkylidene, and group D) consists of divalent or trivalent aliphatic bridges having 1 to 6, preferably 1 to 4, carbon atoms which, in the case of divalent bridges, connect two and, in the case of trivalent bridges, three carbon atoms of the cyclic skeleton and the radical $R^2$ thus constitutes the radical of a bicyclic or tricyclic system, where each of the bridges is unsubstituted or substituted by one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl and oxo, and where $R^2$, inclusive of substituents, preferably has 3 to 20 carbon atoms, in particular 3 to 15 carbon atoms. Preferred $(C_3-C_9)$cycloalkyl radicals are, in this context, cyclopropyl, cyclobutyl, cyclopentyl or cyclohexyl, in particular cyclopropyl, cyclobutyl or cyclopentyl.

$R^2$ is preferably also $(C_4-C_9)$cycloalkenyl which is unsubstituted or substituted by one or more radicals selected from the group consisting of the radicals A), B), C) and D), as are defined as radicals for the case $R^2=(C_3-C_9)$cycloalkyl, and, inclusive of substituents, preferably has 4 to 20 carbon atoms, in particular 4 to 15 carbon atoms.

Preferred $(C_4-C_9)$cycloalkenyl radicals are 1-cyclobutenyl, 2-cyclobutenyl, 1-cyclopentenyl, 2-cyclopentenyl and 3-cyclopentenyl.

$R^2$ is preferably also heterocyclyl which is unsubstituted or substituted by one or more radicals selected from the group consisting of the radicals A), B), C) and D), as are defined as radicals for the case $R^2=(C_3-C_9)$cycloalkyl.

In this context, heterocyclyl is preferably a heterocyclic radical having 3 to 6 ring atoms and one heteroring atom, in particular, a radical selected from the group consisting of pyridyl, thienyl, furyl, pyrrolyl, oxiranyl, 2-oxetanyl, 3-oxetanyl, oxolanyl (=tetrahydrofuryl), pyrrolidyl, piperidyl, in particular oxiranyl, 2-oxetanyl, 3-oxetanyl or oxolanyl, or is a heterocyclic radical having two or three hetero atoms, for example pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

$R^2$ is preferably also phenyl which is unsubstituted or substituted by one or more radicals selected from the group of the radicals A), B) and C) as are defined as radicals for $R^2$=$(C_3-C_9)$cycloalkyl.

Inclusive of substituents, $R^2$ preferably has up to 20 carbon atoms, in particular up to 15 carbon atoms, very especially up to 10 carbon atoms.

$R^2$ is preferably $(C_3-C_9)$cycloalkyl which is unsubstituted or substituted by one or more radicals selected from the group consisting of the radicals A), B), C) and D), where group A) consists of the radicals halogen, hydroxyl, nitro, formyl, aminocarbonyl, cyano and thiocyanato, group B) consists of the radicals $(C_1-C_4)$alkyl, $(C_1-C_4)$alkoxy, $(C_1-C_4)$alkylthio, mono$(C_1-C_4)$alkylamino, di$(C_1-C_4)$alkylamino, $(C_2-C_4)$alkenyl, $(C_2-C_4)$alkynyl, $(C_3-C_6)$cycloalkyl, $(C_4-C_6)$cycloalkenyl, $(C_1-C_4)$alkylidene, $(C_4-C_6)$cycloalkylidene, radicals of the formulae R'—C(=Z')—, R'—C(=Z')—Z—, R'—Z—C(=Z')—, R'R"N—C(=Z'), R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, in particular, $(C_1-C_4)$alkyl, phenyl, phenyl-$(C_1-C_4)$alkyl, $(C_3-C_6)$cycloalkyl or $(C_3-C_6)$cycloalkyl-$(C_1-C_6)$alkyl and where Z and Z' independently are in each case one oxygen or sulfur atom, group C) consists of radicals as shown for group B), but where each radical is substituted by one or more radicals selected from the group consisting of halogen, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, where each of the last-mentioned 8 radicals is unsubstituted or has one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, $(C_1-C_4)$alkylcarbonyl and $(C_1-C_4)$alkoxycarbonyl, and group D) consists of divalent aliphatic bridges which connect two carbon atoms of the cyclic skeleton and the radical $R^2$ thus represents the radical of a bicyclic system, for example bicyclo[1.1.0]butan-1-yl, bicyclo[1.1.0]butan-2-yl, bicyclo[2.1.0]pentan-1-yl, bicyclo[2.1.0]pentan-2-yl or bicyclo[2.1.0]pentan-5-yl, where each of the bridges is unsubstituted or substituted by one or more substituents selected from the group consisting of halogen, $(C_1-C_4)$alkyl, $(C_1-C_4)$alkoxy, $(C_1-C_4)$alkylthio, $(C_1-C_4)$haloalkyl, $(C_1-C_4)$haloalkoxy, $(C_1-C_4)$alkylcarbonyl, $(C_1-C_4)$alkoxycarbonyl and oxo.

$R^2$ is especially preferably $(C_3-C_9)$cycloalkyl which is unsubstituted or substituted by one or more radicals selected from the group consisting of halogen, hydroxyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, $(C_1-C_4)$alkylidene, mono$(C_1-C_4)$alkylamino and di$(C_1-C_4)$alkylamino, or is heterocyclyl or phenyl, where each of the last-mentioned two radicals is unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, heterocyclyl having 3 to 6 ring atoms, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl.

Independently of the radicals $R^1$, $R^2$, $R^4$, $A^1$, $A^2$, $L°$ and $(X)_n$, and preferably in combination with preferred meanings of one or more of these radicals, the following meanings of $R^3$ are of particular interest:

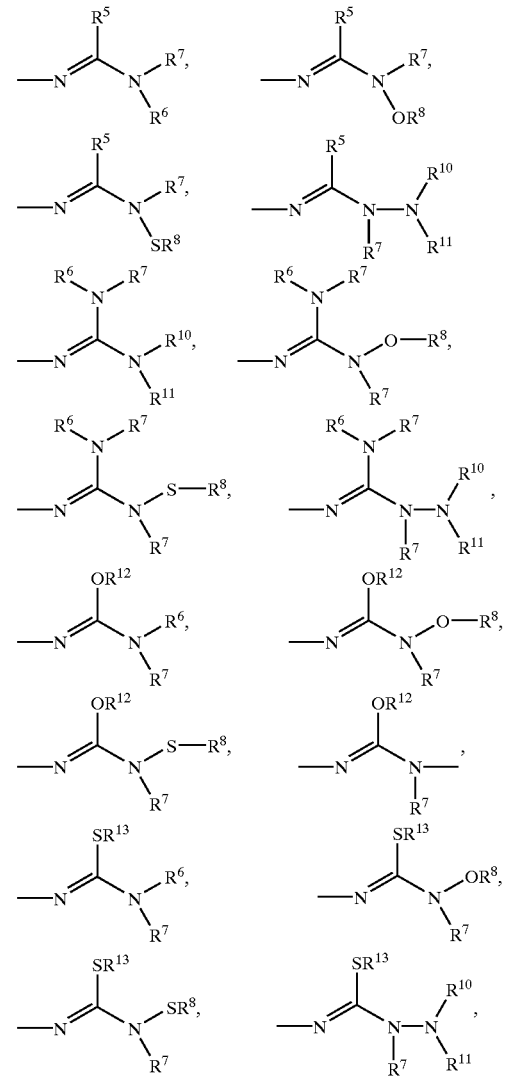

-continued

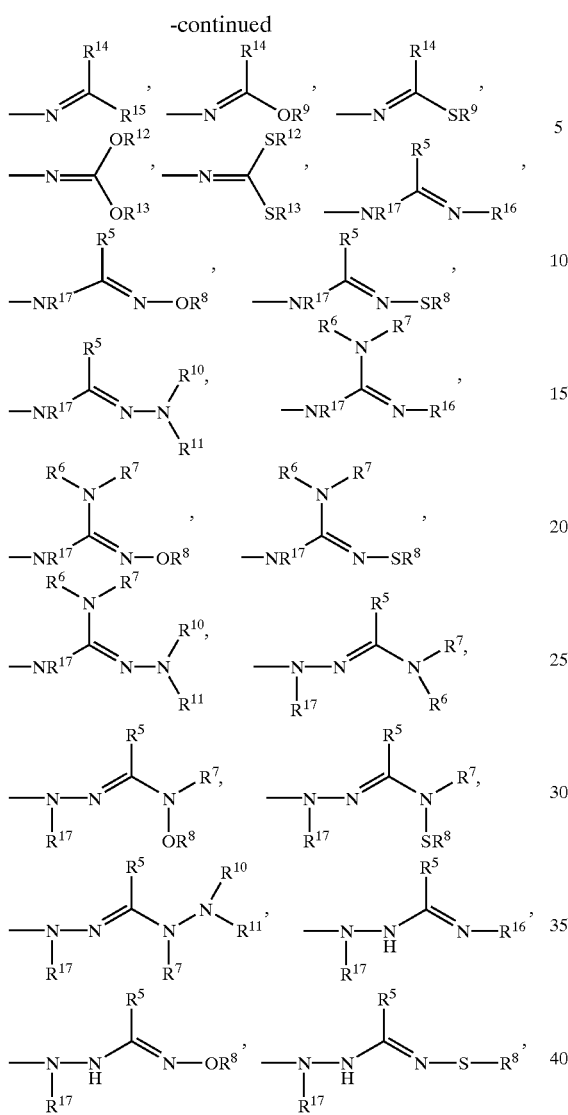

where the radicals $R^5$ to $R^{17}$ are defined further below.

Also of particular interest are compounds

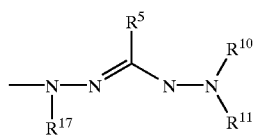

in which $R^6$ and $R^7$ together with the nitrogen atom of the group $NR^6R^7$, $R^7$ and $OR^8$ together with the nitrogen atom of the group $NOR^8R^7$, $R^7$ and $SR^8$ together with the nitrogen atom of the group $NSR^8R^7$, $R^{10}$ and $R^{11}$ together with the nitrogen atom of the group $NR^{10}R^{11}$, $OR^{12}$ and $OR^{13}$ or $SR^{12}$ and $SR^{13}$ together with the carbon atom of the groups of the formulae

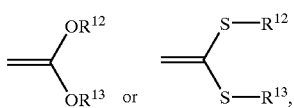

respectively, $OR^9$ and $R^{14}$ or $SR^9$ and $R^{14}$ together with the carbon atom of the groups

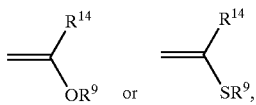

respectively, $R^{14}$ and $R^{15}$ together with the carbon atom of the group

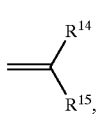

$R^5$ and $R^7$ together with the atom group

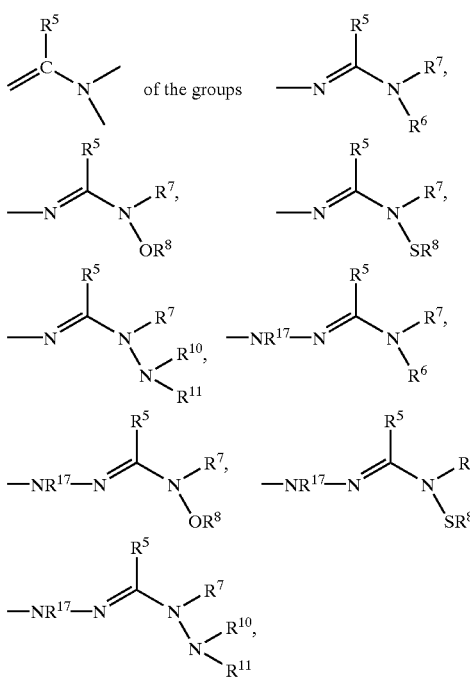

$R^5$ and $R^{17}$ together with the carbon atom of the group

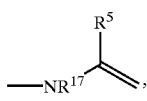

$R^5$ and $R^{16}$ together with the atom group

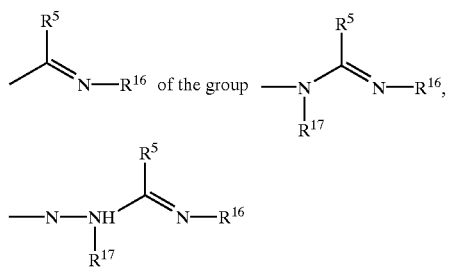

$R^7$ and $R^{10}$ together with the atom group

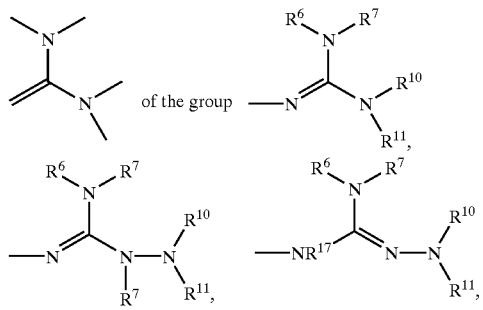

in each case independently of one another form a carbocyclic or heterocyclic ring having 3 to 7 ring atoms and 1 to 6 hetero atoms, where the optional further hetero ring atoms are selected from the group consisting of N, O and S and the carbocyclic or heterocyclic ring is in each case unsubstituted or substituted, the radicals $R^5$ to $R^{17}$ being defined hereinbelow.

In the above formulae for atom groups, the symbol for a double bond "=" which has substituents on one side only (unilateral double bond) denotes the bonding site of a double bond (= a free double bond, synonymous with the binding sites of an ylidene radical) and not the abbreviated form of vinyl.

$R^5$, $R^6$, $R^7$, $R^8$, $R^9$, $R^{10}$, $R^{11}$, $R^{14}$, $R^{15}$, $R^{16}$, $R^{17}$ in the above formulae independently of one another are hydrogen, aryl which is unsubstituted or substituted and, inclusive of substituents, preferably has 6 to 30 carbon atoms, or $(C_3-C_9)$cycloalkyl which is unsubstituted or substituted and, inclusive of substituents, preferably has 3 to 30 carbon atoms, or heterocyclyl which is unsubstituted or substituted and, inclusive of substituents, preferably has 2 to 30 carbon atoms, or $(C_1-C_6)$alkyl, $(C_2-C_6)$alkenyl or $(C_2-C_6)$alkynyl, where each of the last-mentioned 3 radicals is unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, in particular, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and where Z and Z' independently of one another are in each case an oxygen or sulfur atom, and, inclusive of substituents, preferably has 1 to 30 carbon atoms.

$R^{12}$, $R^{13}$ in each case independently of one another are aryl which is unsubstituted or substituted and, inclusive of substituents, preferably has 6 to 30 carbon atoms, or $(C_3-C_9)$cycloalkyl which is unsubstituted or substituted and, inclusive of substituents, preferably has 3 to 30 carbon atoms, or heterocyclyl which is unsubstituted or substituted and, inclusive of substituents, preferably has 2 to 30 carbon atoms, or are $(C_1-C_6)$alkyl, $(C_2-C_6)$alkenyl or $(C_2-C_6)$alkynyl, where each of the last-mentioned 3 radicals is unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, in particular, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted and where Z and Z' independently of one another are in each case one oxygen or sulfur atom, and, inclusive of substituents, preferably has 1 to 30 carbon atoms.

Preferably, the radicals $R^5$, $R^6$, $R^7$, $R^8$, $R^9$, $R_{10}$, $R^{11}$, $R^{14}R^{15}$, $R^{16}$, $R^{17}$ independently of one another are hydrogen.

Preferably, the radicals $R^5$, $R^6$, $R^7$, $R^8$, $R^9$, $R^{10}$, $R^{11}$, $R^{14}R^{15}$, $R^{16}$, $R^{17}$ in each case independently of one another are also phenyl which is unsubstituted or substituted by one or more radicals selected from the group consisting of halogen, hydroxyl, amino, nitro, formyl, carboxyl, sulfo, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl and, inclusive of substituents, has 6 to 30 carbon atoms, preferably 6 to 20 carbon atoms, in particular 6 to 15 carbon atoms.

Preferably, the radicals $R^5$, $R^6$, $R^7$, $R^8$, $R^9$, $R^{10}$, $R^{11}$, $R^{14}$, $R^{15}$, $R^{16}$, $R^{17}$ in each case independently of one another are also $(C_3-C_9)$cycloalkyl which is unsubstituted or substituted by one or radicals selected from the group consisting of halogen, hydroxyl, amino, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkythio, $(C_1-C_4)$haloalkylthio, mono($C_1$–$C_4$)alkylamino and di($C_1$–$C_4$)alkylamino and, inclusive of substituents, has 3 to 30 carbon atoms, preferably 3 to 20 carbon atoms, in particular 3 to 15 carbon atoms.

Preferably, the radicals $R^5$, $R^6$, $R^7$, $R^8$, $R^9$, $R^{10}$, $R^{11}$, $R^{14}$, $R^{15}$, $R^{16}$, $R^{17}$ in each case independently of one another are also heterocyclyl which is unsubstituted or substituted by one or more radicals selected from the group consisting of halogen, hydroxyl, amino, nitro, formyl, carboxyl, sulfonyl, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino, di($C_1$–$C_4$)alkylamino, ($C_3$–$C_9$)cycloalkyl, [($C_1$–$C_4$)alkyl]carbonyl, [($C_1$–$C_4$)alkoxy]carbonyl, aminocarbonyl, mono($C_1$–$C_4$)alkylaminocarbonyl, di($C_1$–$C_4$)alkylaminocarbonyl, ($C_1$–$C_4$)alkylsulfonyl and ($C_1$–$C_4$)haloalkylsulfonyl and, inclusive of substituents, has 2 to 30 carbon atoms, preferably 2 to 20 carbon atoms, in particular 2 to 15 carbon atoms.

Here and also in other radicals, heterocyclyl preferably is a heterocyclic radical having 3 to 7, in particular 3 to 6, ring atoms and one hetero atom selected from the group consisting of N, O and S, for example pyridyl, thienyl, furyl, pyrrolyl, oxiranyl, oxetanyl, oxolanyl (=tetrahydrofuryl), oxanyl, pyrrolidyl, piperidyl, or is a heterocyclic radical having two or three hetero atoms selected from the group consisting of pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl, morpholinyl.

$R^5$, $R^6$, $R^7$, $R^8$, $R^9$, $R^{10}$, $R^{11}$ $R^{14}$, $R^{15}$, $R^{16}$, $R^{17}$ independently of one another are preferably also ($C_1$–$C_6$)alkyl, ($C_2$–$C_6$)alkenyl or ($C_2$–$C_6$)alkynyl, where each of the last-mentioned 3 radicals is unsubstituted or substituted by one or more radicals selected from the group consisting of halogen, hydroxyl, cyano, nitro, thiocyanato, ($C_1$–$C_4$)alkoxy, ($C_1$–$C_4$)haloalkoxy, ($C_2$–$C_4$)alkenyloxy, ($C_2$–$C_4$)haloalkenyloxy, ($C_1$–$C_4$)alkylthio, ($C_1$–$C_4$)alkylsulfinyl, ($C_1$–$C_4$)alkylsulfonyl, ($C_1$–$C_4$)haloalkylsulfinyl, ($C_1$–$C_4$)haloalkylsulfonyl, ($C_3$–$C_6$)cycloalkyl which is unsubstituted or substituted by one or more radicals selected from the group consisting of halogen, hydroxyl, amino, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino and di($C_1$–$C_4$)alkylamino, phenyl and heterocyclyl, where each of the two last-mentioned radicals is unsubstituted or substituted by one or more radicals selected from the group consisting of halogen, hydroxyl, amino, nitro, formyl, carboxyl, sulfonyl, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino, di($C_1$–$C_4$)alkylamino, ($C_3$–$C_9$)cycloalkyl, [($C_1$–$C_4$)alkyl]carbonyl, [($C_1$–$C_4$)alkoxy]carbonyl, aminocarbonyl, mono($C_1$–$C_4$)alkylaminocarbonyl, di($C_1$–$C_4$)alkylaminocarbonyl, ($C_1$–$C_4$)alkylsulfonyl and ($C_1$–$C_4$)haloalkylsulfonyl, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, in particular, ($C_1$–$C_4$)alkyl, phenyl, phenyl-($C_1$–$C_4$)alkyl, ($C_3$–$C_6$)cycloalkyl or ($C_3$–$C_6$)cycloalkyl-($C_1$–$C_4$)alkyl, where each of the 5 last-mentioned radicals is unsubstituted or substituted by one or more radicals selected from the group consisting of halogen, hydroxyl, amino, nitro, formyl, cyano, thiocyanato, ($C_1$–$C_4$)alkoxy, ($C_1$–$C_4$)alkylthio, mono($C_1$–$C_4$)alkylamino, di($C_1$–$C_4$)alkylamino, ($C_2$–$C_4$)alkenyl, ($C_2$–$C_4$)alkynyl, ($C_3$–$C_6$)cycloalkyl and, in the case of cyclic radicals, also ($C_1$–$C_4$)alkyl and ($C_1$–$C_4$)haloalkyl, and where Z and Z' independently of one another are in each case one oxygen or sulfur atom, and, inclusive of substituents, preferably has 1 to 20 carbon atoms, in particular 1 to 15 carbon atoms, $R^5$, $R^6$, $R^7$, $R^8$, $R^9$, $R^{10}$, $R^{11}$, $R^{14}$, $R^{15}$, $R^{16}$, $R^{17}$ in each case independently of one another are preferably ($C_1$–$C_4$) alkyl which is unsubstituted or substituted by one or more radicals selected from the group consisting of halogen, ($C_1$–$C_4$)alkoxy, ($C_1$–$C_4$)alkylthio, ($C_1$–$C_4$)alkylsulfonyl, ($C_3$–$C_9$)cycloalkyl which is unsubstituted or substituted and phenyl which is unsubstituted or substituted by one or more radicals selected from the group consisting of halogen, ($C_1$–$C_4$)alkyl and ($C_1$–$C_4$)haloalkyl, ($C_1$–$C_4$)alkoxy, ($C_1$–$C_4$)haloalkoxy, ($C_1$–$C_4$)alkylthio, amino, mono- and di[($C_1$–$C_4$)alkyl]amino, ($C_1$–$C_4$)alkanoylamino, benzoylamino, nitro, cyano, [($C_1$–$C_4$)alkyl]carbonyl, formyl, carbamoyl, mono- and di[($C_1$–$C_4$)alkyl]aminocarbonyl and ($C_1$–$C_4$)alkylsulfonyl, and heterocyclyl having 3 to 6 ring atoms and 1 to 3 hetero ring atoms selected from the group consisting of N, O and S, the ring being unsubstituted or substituted by one or more radicals selected from the group consisting of halogen, ($C_1$–$C_4$)alkyl and oxo, or phenyl which is unsubstituted or substituted by one or more radicals selected from the group consisting of halogen, hydroxyl, amino, nitro, formyl, carboxyl, sulfonyl, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino, di($C_1$–$C_4$)alkylamino, ($C_3$–$C_9$)cycloalkyl, [($C_1$–$C_4$)alkyl]carbonyl, [($C_1$–$C_4$)alkoxy]carbonyl, aminocarbonyl, mono($C_1$–$C_4$)alkylaminocarbonyl, di($C_1$–$C_4$)alkylaminocarbonyl, ($C_1$–$C_4$)alkylsulfonyl and ($C_1$–$C_4$)haloalkylsulfonyl and, inclusive of substituents, has 2 to 30 carbon atoms, preferably 2 to 20 carbon atoms, in particular 2 to 15 carbon atoms.

$R^{12}$, $R^{13}$ in each case independently of one another are preferably also phenyl which is unsubstituted or substituted by one or more radicals selected from the group consisting of halogen, hydroxyl, amino, nitro, formyl, carboxyl, sulfo, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino, di($C_1$–$C_4$)alkylamino, ($C_3$–$C_9$)cycloalkyl, [($C_1$–$C_4$)alkyl]carbonyl, [($C_1$–$C_4$)alkoxy]carbonyl, aminocarbonyl, mono($C_1$–$C_4$)alkylaminocarbonyl, di($C_1$–$C_4$)alkylaminocarbonyl, ($C_1$–$C_4$)alkylsulfonyl and ($C_1$–$C_4$)haloalkylsulfonyl and, inclusive of substituents, has 6 to 30 carbon atoms, preferably 6 to 20 carbon atoms, in particular 6 to 15 carbon atoms.

$R^{12}$, $R^{13}$ in each case independently of one another are preferably also ($C_3$–$C_9$)cycloalkyl which is unsubstituted or substituted by one or more radicals selected from the group consisting of halogen, hydroxyl, amino, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino and di($C_1$–$C_4$)alkylamino and, inclusive of substituents, has 3 to 30 carbon atoms, preferably 3 to 20 carbon atoms, in particular 3 to 15 carbon atoms.

$R^{12}$, $R^{13}$ in each case independently of one another are preferably also heterocyclyl which is unsubstituted or substituted by one or more radicals selected from the group consisting of halogen, hydroxyl, amino, nitro, formyl, carboxyl, sulfonyl, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)

alkylamino, di($C_1$–$C_4$)alkylamino, ($C_3$–$C_9$)cycloalkyl, [($C_1$–$C_4$)alkyl]carbonyl, [($C_1$–$C_4$)alkoxy]carbonyl, aminocarbonyl, mono($C_1$–$C_4$)alkylaminocarbonyl, di($C_1$–$C_4$)alkylaminocarbonyl, ($C_1$–$C_4$)alkylsulfonyl and ($C_1$–$C_4$)haloalkylsulfonyl and, inclusive of substituents, has 2 to 30 carbon atoms, preferably 2 to 20 carbon atoms, in particular 2 to 15 carbon atoms.

Here and also in other radicals, heterocyclyl is preferably a heterocyclic radical having 3 to 7, in particular 3 to 6, ring atoms and one hetero atom selected from the group consisting of N, O and S, for example pyridyl, thienyl, furyl, pyrrolyl, oxiranyl, oxetanyl, oxolanyl (=tetrahydrofuryl), oxanyl, pyrrolidyl, piperidyl, or is a heterocyclic radical having two or three hetero atoms selected from the group consisting of pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl, morpholinyl.

$R^{12}$, $R^{13}$ in each case independently of one another are preferably also ($C_1$–$C_6$)alkyl, ($C_2$–$C_6$)alkenyl or ($C_2$–$C_6$) alkynyl, where each of the last-mentioned 3 radicals is unsubstituted or substituted by one or more radicals selected from the group consisting of halogen, hydroxyl, cyano, nitro, thiocyanato, ($C_1$–$C_4$)alkoxy, ($C_1$–$C_4$)haloalkoxy, ($C_2$–$C_4$)alkenyloxy, ($C_2$–$C_4$)haloalkenyloxy, ($C_1$–$C_4$) alkylthio ($C_1$–$C_4$)alkylsulfinyl, ($C_1$–$C_4$)alkylsulfonyl, ($C_1$–$C_4$)haloalkylsulfinyl, ($C_1$–$C_4$)haloalkylsulfonyl, ($C_3$–$C_6$)cycloalkyl which is unsubstituted or substituted by one or more radicals selected from the group consisting of halogen, hydroxyl, amino, cyano, thiocyanato, ($C_1$–$C_4$) alkyl, ($C_1$–$C_4$)haloalkyl, ($C_1$–$C_4$)alkoxy, ($C_1$–$C_4$) haloalkoxy, ($C_1$–$C_4$)alkylthio, ($C_1$–$C_4$)haloalkylthio, mono ($C_1$–$C_4$)alkylamino and di($C_1$–$C_4$)alkylamino, or phenyl and heterocyclyl, where each of the two last-mentioned radicals is unsubstituted or substituted by one or more radicals selected from the group consisting of halogen, hydroxyl, amino, nitro, formyl, carboxyl, sulfonyl, cyano, thiocyanato, ($C_1$–$C_4$)alkyl, ($C_1$–$C_4$)haloalkyl, ($C_1$–$C_4$) alkoxy, ($C_1$–$C_4$)haloalkoxy, ($C_1$–$C_4$)alkylthio, ($C_1$–$C_4$) haloalkylthio, mono($C_1$–$C_4$)alkylamino, di($C_1$–$C_4$) alkylamino, ($C_3$–$C_9$)cycloalkyl, [($C_1$–$C_4$)alkyl]carbonyl, [($C_1$–$C_4$)alkoxy]carbonyl, aminocarbonyl, mono($C_1$–$C_4$) alkylaminocarbonyl, di($C_1$–$C_4$)alkylaminocarbonyl, ($C_1$–$C_4$)alkylsulfonyl and ($C_1$–$C_4$)haloalkylsulfonyl, and radicals of the formulae R'—C(=Z')—, R'—C(=Z')—Z—, R'—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen or, in particular, ($C_1$–$C_4$)alkyl, phenyl, phenyl-($C_1$–$C_4$)alkyl, ($C_3$–$C_6$)cycloalkyl or ($C_3$–$C_6$)cycloalkyl-($C_1$–$C_4$)alkyl, where each of the 5 last-mentioned radicals is unsubstituted or substituted by one or more radicals selected from the group consisting of halogen, hydroxyl, amino, nitro, formyl, cyano, thiocyanato, ($C_1$–$C_4$)alkoxy, ($C_1$–$C_4$)alkylthio, mono($C_1$–$C_4$)alkylamino, di($C_1$–$C_4$)alkylamino, ($C_2$–$C_4$)alkenyl, ($C_2$–$C_4$)alkynyl, ($C_3$–$C_6$)cycloalkyl and, in the case of cyclic radicals, also ($C_1$–$C_4$)alkyl and ($C_1$–$C_4$)haloalkyl, and where Z and Z' independently of one another are in each case one oxygen or sulfur atom, and, inclusive of substituents, preferably has 1 to 20 carbon atoms, in particular 1 to 15 carbon atoms.

$R^{12}$, $R^{13}$ in each case independently of one another are preferably ($C_1$–$C_4$)alkyl which is unsubstituted or substituted by one or more radicals selected from the group consisting of halogen, ($C_1$–$C_4$)alkoxy, ($C_1$–$C_4$)alkylthio, ($C_1$–$C_4$)alkylsulfonyl, ($C_3$–$C_9$)cycloalkyl which is unsubstituted or substituted and phenyl which is unsubstituted or substituted by one or more radicals selected from the group consisting of halogen, ($C_1$–$C_4$)alkyl and ($C_1$–$C_4$)haloalkyl, ($C_1$–$C_4$)alkoxy, ($C_1$–$C_4$)haloalkoxy, ($C_1$–$C_4$)alkylthio, amino, mono- and di[($C_1$–$C_4$)alkyl]amino, ($C_1$–$C_4$) alkanoylamino, benzoylamino, nitro, cyano, [($C_1$–$C_4$)alkyl] carbonyl, formyl, carbamoyl, mono- and di-[($C_1$–$C_4$)alkyl] aminocarbonyl and ($C_1$–$C_4$)alkylsulfonyl, and heterocyclyl having 3 to 6 ring atoms and 1 to 3 hetero ring atoms selected from the group consisting of N, O and S, where the ring is unsubstituted or substituted by one or more radicals selected from the group consisting of halogen, ($C_1$–$C_4$)alkyl and oxo, or phenyl which is unsubstituted or substituted by one or more radicals selected from the group consisting of halogen, hydroxyl, amino, nitro, formyl, carboxyl, sulfonyl, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino, di($C_1$–$C_4$) alkylamino, ($C_3$–$C_9$)cycloalkyl, [($C_1$–$C_4$)alkyl]carbonyl, [($C_1$–$C_4$)alkoxy]carbonyl, aminocarbonyl, mono($C_1$–$C_4$) alkylaminocarbonyl, di($C_1$–$C_4$)alkylaminocarbonyl, ($C_1$–$C_4$)alkylsulfonyl and ($C_1$–$C_4$)haloalkylsulfonyl and, inclusive of substituents, has 2 to 30 carbon atoms, preferably 2 to 20 carbon atoms, in particular 2 to 15 carbon atoms.

Independently of the radicals $R^1$, $R^2$, $R^3$, $L^o$, $A^1$, $A^2$ and $(X)_n$, and preferably in combination with preferred meanings of one or more of these radicals, the following meanings of $R^4$ are of particular interest:

$R^4$ is, for example, a radical of the formula —$B^1$-$D^1$, where $B^1$ and $D^1$ are preferably as defined further below.

$R^4$ is preferably hydrogen, ($C_1$–$C_4$)alkyl, phenyl or ($C_3$–$C_6$)cycloalkyl, where each of the 3 last-mentioned radicals is unsubstituted or substituted by one or more radicals selected from the group consisting of halogen, hydroxyl, amino, nitro, formyl, carboxyl, sulfonyl, cyano, thiocyanato, ($C_1$–$C_4$)alkoxy, ($C_1$–$C_4$)haloalkoxy, ($C_1$–$C_4$) alkylthio, ($C_1$–$C_4$)haloalkylthio, mono($C_1$–$C_4$)alkylamino, di($C_1$–$C_4$)alkylamino, ($C_3$–$C_9$)cycloalkyl, [($C_1$–$C_4$)alkyl] carbonyl, [($C_1$–$C_4$)alkoxy]carbonyl, aminocarbonyl, mono ($C_1$–$C_4$)alkylaminocarbonyl, di($C_1$–$C_4$)alkylaminocarbonyl, ($C_1$–$C_4$)alkylsulfonyl, ($C_1$–$C_4$)haloalkylsulfonyl and, in the case of cyclic radicals, also ($C_1$–$C_4$)alkyl and ($C_1$–$C_4$)haloalkyl, or formyl, [($C_1$–$C_4$)alkyl]carbonyl, [($C_1$–$C_4$)alkoxy]carbonyl, aminocarbonyl, mono($C_1$–$C_4$) alkylaminocarbonyl or di($C_1$–$C_4$)alkylaminocarbonyl; in particular hydrogen, methyl, ethyl, n-propyl or isopropyl; especially preferably hydrogen.

Independently of the radicals $R^1$ to $R^4$, $A^1$, $A^2$ and $(X)_n$, and preferably in combination with preferred meanings of one or more of these radicals, the following meanings of $L^o$ are of particular interest:

$L^o$ is a direct bond or oxygen.

Independently of the radicals $R^1$ to $R^4$, $L^o$, $A^2$ and $(X)_n$ and preferably in combination with preferred meanings of one or more of these radicals, the following meanings of $A^1$ are of particular interest:

$A^1$ is, for example, straight-chain alkylene having 1 to 5 carbon atoms or straight-chain alkenylene or alkynylene having in each case 2 to 5 carbon atoms, where each of the three last-mentioned diradicals is unsubstituted or substituted by one or more radicals selected from the group consisting of halogen, nitro, cyano, thiocyanato and a radical of the formula —$B^2$-$D^2$, in which $B^2$ is a direct bond or a divalent group of the formulae —O—, —$SO_2$—, —CO—, —O—CO—, —$NR^O$—, —NR$^O$—CO—, —CO—NR$^O$—, —O—CO—NR$^O$— or —NR$^O$—CO—O—, in which R$^O$ independently of one another are in each case hydrogen, (C$_1$–C$_4$)alkyl, phenyl, phenyl-(C$_1$–C$_4$)alkyl, (C$_3$–C$_6$)cycloalkyl or (C$_3$–C$_6$)cycloalkyl-(C$_1$–C$_4$)alkyl, where each of the last-mentioned 5 radicals is unsubstituted or substituted by one or more radicals selected from the group consisting of halogen, hydroxyl, amino, nitro, formyl, carboxyl, sulfonyl, cyano, thiocyanato, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl, (C$_1$–C$_4$)haloalkylsulfonyl and, in the case of cyclic radicals, also (C$_1$–C$_4$)alkyl and (C$_1$–C$_4$)haloalkyl.

A$^1$ is preferably a radical of the formula

—CH$_2$—, —CH$_2$CH$_2$—, —CH$_2$CH$_2$CH$_2$—, —CH$_2$CH$_2$CH$_2$CH$_2$— or —CH$_2$CH$_2$CH$_2$CH$_2$CH$_2$—, which radical is unsubstituted. Also preferred is one of the above radicals which is substituted by one or more of the abovementioned radicals —B$^2$-D$^2$. A$^1$ is especially preferably a radical of the formula —CH$_2$CH$_2$— or —CH$_2$CH$_2$CH$_2$—, which radical is unsubstituted or substituted by one or two radicals of the formula hydroxyl, (C$_1$–C$_4$)alkyl or (C$_1$–C$_4$)alkoxy.

Independently of the radicals R$^1$ to R$^4$, L$^o$, A$^1$ and (X)$_n$ and preferably in combination with preferred meanings of one or more of these radicals, the following meanings of A$^2$ are of particular interest:

A$^2$ is preferably a direct bond or a group of the formula —CH$_2$—, —CH$_2$CH$_2$—, —CH$_2$CH$_2$CH$_2$— or —CH$_2$CH$_2$CH$_2$CH$_2$—, where each of the 4 last-mentioned diradicals is unsubstituted or substituted by one or more radicals selected from the group consisting of halogen, nitro, cyano, thiocyanato and radicals of the formula —B$^3$-D$^3$, or a divalent radical of the formula V$^1$, V$^2$, V$^3$, V$^4$ or V$^5$, —CR$^a$R$^b$—W*—CR$^c$R$^d$— (V$^1$)

—CR$^a$R$^b$—W*—CR$^c$R$^d$—CR$^e$R$^f$— (V$^2$)

—CR$^a$R$^b$—CR$^c$R$^d$—W*—CR$^e$R$^f$— (V$^3$)

—CR$^a$R$^b$—CR$^c$R$^d$—W*— (V4)

—CR$^a$R$^b$—W*— (V$^5$)

where each of the radicals R$^a$ to R$^f$ in each case independently of one other is hydrogen, halogen, nitro, cyano, thiocyanato or a radical of the formula —B$^4$-D$^4$, W* is in each case O, S or a group of the formula N(B$^5$-D$^5$), and B$^3$, B$^4$, B$^5$, D$^3$, D$^4$ and D$^5$ are as defined below.

A$^2$ is especially preferably a direct bond or a group of the formula

—CH$_2$—, —CH$_2$CH$_2$—, —CH$_2$CH$_2$CH$_2$—, —CH$_2$CH$_2$CH$_2$CH$_2$, —CH$_2$O—CH$_2$—, —CH$_2$—O—CH$_2$—CH$_2$—, —CH$_2$—CH$_2$—O—CH$_2$—, —CH$_2$—S—CH$_2$—, —CH$_2$—S—CH$_2$—CH$_2$—, —CH$_2$—CH$_2$—S—CH$_2$—, —CH$_2$NH—CH$_2$—, —CH$_2$—NH—CH$_2$—CH$_2$—, —CH$_2$—CH$_2$—NH—CH$_2$—, —CH$_2$—N(CH$_3$)—CH$_2$—, —CH$_2$—N(CH$_3$)—CH$_2$CH$_2$ or —CH$_2$—CH$_2$—N(CH$_3$)—CH$_2$—.

B$^1$ and B$^5$ are preferably in each case independently of one another a direct bond a divalent group of the formulae —C(=Z*)—, —C(=Z*)—Z**—, —C(=Z*)—NH— or —C(=Z*)—NR*—, where Z*=O or S, Z**=O or S and R*=(C$_1$–C$_4$)alkyl, phenyl, phenyl-(C$_1$–C$_4$)alkyl, (C$_3$–C$_6$)cycloalkyl or (C$_3$–C$_6$)cycloalkyl(C$_1$–C$_4$)alkyl, where each of the 5 last-mentioned radicals is unsubstituted or substituted, preferably unsubstituted or substituted by one or more radicals selected from the group consisting of halogen, hydroxyl, amino, nitro, formyl, carboxyl, sulfo, cyano, thiocyanato, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl, (C$_1$–C$_4$)haloalkylsulfonyl and, in the case of cyclic radicals, also (C$_1$–C$_4$)alkyl and (C$_1$–C$_4$)haloalkyl.

B$^1$ and B$^5$ are also preferably independently of another a direct bond or a divalent group of the formulae —C(=Z*)—, —C(=Z*)—Z**—, —C(=Z*)—NH— or —C(=Z*)—NR*—, where Z*=O or S, Z**=O or S and R*=(C$_1$–C$_4$)alkyl, phenyl, phenyl-(C$_1$–C$_4$)alkyl, (C$_3$–C$_6$)cycloalkyl or (C$_3$–C$_6$)cycloalkyl-(C$_1$–C$_4$)alkyl, where each of the 5 last-mentioned radicals is unsubstituted or substituted by one or more radicals selected from the group consisting of halogen, hydroxyl, amino, formyl, (C$_1$–C$_4$)alkoxy, (C$_1$–C$_4$)haloalkoxy, (C$_1$–C$_4$)alkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl and, in the case of cyclic radicals, also (C$_1$–C$_4$)alkyl and (C$_1$–C$_4$)haloalkyl, in particular R*=(C$_1$–C$_4$)alkyl or (C$_3$–C$_6$)cycloalkyl or in particular R*=phenyl or phenyl-(C$_1$–C$_4$)alkyl, where each of the two last-mentioned radicals is unsubstituted or substituted in the phenyl moiety or by one or more radicals selected from the group consisting of halogen, (C$_1$–C$_4$)alkyl, (C$_1$–C$_4$)haloalkyl, (C$_1$–C$_4$)alkoxy or (C$_1$–C$_4$)haloalkoxy.

B$^2$, B$^3$ and B$^4$ are preferably in each case independently of one another a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —NR$^O$—, —O—NR$^O$—O—, —NR$^O$—CO—, —CO—NR$^O$—, —O—CO—NR$^O$— or —NR$^O$—CO—O—, where p is the integer 0, 1 or 2 and R$^O$=hydrogen, (C$_1$–C$_4$)alkyl, phenyl, phenyl-(C$_1$–C$_4$)alkyl, (C$_3$–C$_6$)cycloalkyl or (C$_3$–C$_6$)cycloalkyl-(C$_1$–C$_4$)alkyl, where each of the 5 last-mentioned radicals is unsubstituted or substituted by one or more radicals selected from the group consisting of halogen, hydroxyl, amino, nitro, formyl, carboxyl, sulfo, cyano, thiocyanato, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl, (C$_1$–C$_4$)haloalkylsulfonyl and, in the case of cyclic radicals, also (C$_1$–C$_4$)alkyl and (C$_1$–C$_4$)haloalkyl, and in particular R$^O$=hydrogen, (C$_1$–C$_4$)alkyl or (C$_3$–C$_6$)cycloalkyl or in particular R$^O$=phenyl or phenyl-(C$_1$–C$_4$)alkyl, where each of the two last-mentioned radicals is unsubstituted or substituted in the phenyl moiety by one or more radicals selected from the group consisting of halogen, (C$_1$–C$_4$) alkyl, (C$_1$–C$_4$)haloalkyl, (C$_1$–C$_4$)alkoxy or (C$_1$–C$_4$)haloalkoxy.

$B^2$, $B^3$ and $B^4$ are also preferably independently of one another a direct bond or a divalent group of the formulae —O—, —S(O)$_p$—, —CO—, —O—CO—, —CO—O—, —S—CO—, —CO—S—, —NR$^O$—, —NR$^O$—CO—, —CO—NR$^O$—, —O—CO—NR$^O$— or —NR$^O$—CO—O—, where p is the integer 0, 1 or 2, in particular 0 or 2, and R$^O$ has the abovementioned meaning, very especially H or (C$_1$–C$_4$)alkyl.

$D^1$, $D^2$, $D^3$, $D^4$ and $D^5$ preferably independently of one another are hydrogen, (C$_1$–C$_6$)alkyl, phenyl, phenyl-(C$_1$–C$_4$)alkyl, (C$_3$–C$_6$)cycloalkyl or (C$_3$–C$_6$)cycloalkyl-(C$_1$–C$_6$)alkyl, where each of the 5 last-mentioned radicals is unsubstituted or substituted, preferably unsubstituted or substituted by one or more radicals selected from the group consisting of halogen, hydroxyl, amino, nitro, formyl, carboxyl, sulfo, cyano, thiocyanato, (C$_1$–C$_4$)alkoxy, (C$_1$–C$_4$)haloalkoxy, (C$_1$–C$_4$)alkylthio, (C$_1$–C$_4$) haloalkylthio, mono(C$_1$–C$_4$)alkylamino, di(C$_1$–C$_4$) alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl, (C$_1$–C$_4$)haloalkylsulfonyl and, in the case of cyclic radicals, also (C$_1$–C$_4$)alkyl and (C$_1$–C$_4$) haloalkyl.

$D^1$, $D^2$, $D^3$, $D^4$ and $D^5$ also preferably independently of one another are (C$_1$–C$_4$)alkyl, phenyl, phenyl-(C$_1$–C$_4$)alkyl, (C$_3$–C$_6$)cycloalkyl or (C$_3$–C$_6$)cycloalkyl-(C$_1$–C$_4$)alkyl, where each of the 5 last-mentioned radicals is unsubstituted or substituted by one or more radicals selected from the group consisting of halogen, hydroxyl, amino, formyl, (C$_1$–C$_4$)alkoxy, (C$_1$–C$_4$)haloalkoxy, (C$_1$–C$_4$)alkylthio, mono(C$_1$–C$_4$)alkylamino, di(C$_1$–C$_4$)alkylamino, (C$_3$–C$_9$) cycloalkyl, [(C$_1$–C$_4$)alkyl]carbonyl, [(C$_1$–C$_4$)alkoxy] carbonyl, aminocarbonyl, mono(C$_1$–C$_4$) alkylaminocarbonyl, di(C$_1$–C$_4$)alkylaminocarbonyl and, in the case of cyclic radicals, also (C$_1$–C$_4$)alkyl and (C$_1$–C$_4$) haloalkyl, and, in particular, they are (C$_1$–C$_4$)alkyl or (C$_3$–C$_6$)cycloalkyl or phenyl or phenyl-(C$_1$–C$_4$)alkyl, where each of the two last-mentioned radicals is unsubstituted or substituted in the phenyl moiety by one or more radicals selected from the group consisting of halogen, (C$_1$–C$_4$)alkyl, (C$_1$–C$_4$)haloalkyl, (C$_1$–C$_4$)alkoxy or (C$_1$–C$_4$)haloalkoxy.

Independently of the radicals $R^1$ to $R^4$, $L^O$, $A^1$ and $A^2$ and preferably in combination with preferred meanings of one or more of these radicals, the following meanings of $(X)_n$ are of particular interest:

$(X)_n$ is n substituents X, where X preferably in each case independently of one another are halogen, hydroxyl, amino, nitro, formyl, carboxyl, cyano, thiocyanato, aminocarbonyl or (C$_1$–C$_4$)alkyl, (C$_1$–C$_4$)alkoxy, (C$_1$–C$_4$) alkylthio, mono(C$_1$–C$_4$)alkylamino, di(C$_1$–C$_4$) alkylamino, (C$_2$–C$_4$)alkenyl, (C$_2$–C$_4$)alkynyl, [(C$_1$–C$_4$) alkyl]carbonyl, [(C$_1$–C$_4$)alkoxy]carbonyl, mono(C$_1$–C$_4$) alkylaminocarbonyl, di(C$_1$–C$_4$)alkylaminocarbonyl, N-(C$_1$–C$_6$)alkanoylamino or N-(C$_1$–C$_4$)alkanoyl-N-(C$_1$–C$_4$)alkylamino, where each of the last-mentioned 13 radicals is unsubstituted or substituted, preferably unsubstituted or substituted by one or more radicals selected from the group consisting of halogen, hydroxyl, amino, cyano, thiocyanato, (C$_1$–C$_4$)alkoxy, (C$_1$–C$_4$)haloalkoxy, (C$_1$–C$_4$)alkylthio, mono(C$_1$–C$_4$)alkylamino, di(C$_1$–C$_4$) alkylamino, (C$_3$–C$_6$)cycloalkyl, (C$_3$–C$_6$) cycloalkylamino, [(C$_1$–C$_4$)alkyl]carbonyl, [(C$_1$–C$_4$) alkoxy]carbonyl, aminocarbonyl, mono(C$_1$–C$_4$) alkylaminocarbonyl, di(C$_1$–C$_4$)alkylaminocarbonyl, phenyl, phenoxy, phenylthio, phenylcarbonyl, heterocyclyl, heterocyclyloxy, heterocyclylthio and heterocyclylamino, where each of the last-mentioned 8 radicals is unsubstituted or has one or more substituents selected from the group consisting of halogen, nitro, cyano, (C$_1$–C$_4$) alkyl, (C$_1$–C$_4$)alkoxy, (C$_1$–C$_4$)alkylthio, (C$_1$–C$_4$) haloalkyl, (C$_1$–C$_4$)haloalkoxy, formyl, (C$_1$–C$_4$) alkylcarbonyl and (C$_1$–C$_4$)alkoxycarbonyl, or (C$_3$–C$_9$)cycloalkyl, phenyl, phenoxy, phenylthio, phenylcarbonyl, heterocyclyl, heterocyclyloxy, heterocyclylthio or heterocyclylamino, where each of the last-mentioned 9 radicals is unsubstituted or substituted, preferably unsubstituted or substituted by one or more radicals selected from the group consisting of halogen, hydroxyl, amino, nitro, formyl, carboxyl, cyano, thiocyanato, (C$_1$–C$_4$)alkyl, (C$_1$–C$_4$)haloalkyl, (C$_1$–C$_4$)alkoxy, (C$_1$–C$_4$) haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_6$)cycloalkyl, [(C$_1$–C$_4$)alkyl]carbonyl, [(C$_1$–C$_4$)alkoxy]carbonyl, aminocarbonyl, mono (C$_1$–C$_4$)alkylaminocarbonyl and di(C$_1$–C$_4$) alkylaminocarbonyl, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, (C$_1$–C$_4$)alkyl and oxo.

In this context, n is preferably 0, 1, 2 or 3, in particular 0, 1 or 2.

$(X)_n$ is also preferably n substituents X, where X in each case independently of one another are halogen, hydroxyl, amino, nitro, formyl, carboxyl, cyano, thiocyanato, (C$_1$–C$_4$)alkyl, cyano-(C$_1$–C$_4$)alkyl, (C$_1$–C$_4$)alkoxy, (C$_1$–C$_4$)alkylamino, di[(C$_1$–C$_4$)alkyl]amino, halo(C$_1$–C$_4$) alkyl, hydroxyl(C$_1$–C$_4$)alkyl, (C$_1$–C$_4$)alkoxy-(C$_1$–C$_4$) alkyl, halo(C$_1$–C$_4$)alkoxy-(C$_1$–C$_4$)alkyl, (C$_1$–C$_4$) alkylthio, halo(C$_1$–C$_4$)alkylthio, (C$_2$–C$_6$)alkenyl, halo (C$_2$–C$_6$)alkenyl, (C$_2$–C$_6$)alkynyl, halo(C$_2$–C$_6$)alkynyl, (C$_1$–C$_4$)alkylamino-(C$_1$–C$_4$)alkyl, di[(C$_1$–C$_4$)alkyl] amino-(C$_1$–C$_4$)alkyl, (C$_3$–C$_6$)cycloalkylamino-(C$_1$–C$_4$) alkyl, (C$_3$–C$_9$)cycloalkyl, heterocyclyl-(C$_1$–C$_4$)alkyl having 3 to 9 ring members, where the cyclic groups in the last-mentioned 3 radicals are unsubstituted or substituted by one or more radicals, preferably up to three radicals, selected from the group consisting of (C$_1$–C$_4$)alkyl, halogen and cyano, or phenyl, phenoxy, phenylcarbonyl, phenylcarbonyl-(C$_1$–C$_4$)alkyl, (C$_1$–C$_4$)alkoxy-carbonyl-(C$_1$–C$_4$)alkyl, (C$_1$–C$_4$)alkylaminocarbonyl-(C$_1$–C$_4$) alkyl, (C$_1$–C$_4$)alkyl-carbonyl, (C$_1$–C$_4$)alkoxycarbonyl, aminocarbonyl, (C$_1$–C$_4$)alkylaminocarbonyl, phenoxy-(C$_1$–C$_4$)alkyl, phenyl-(C$_1$–C$_4$)alkyl, heterocyclyl, heterocyclylamino, heterocyclyloxy, heterocyclylthio or one of the last-mentioned 16 radicals which is substituted in the acyclic moiety or, preferably in the cyclic moiety by one or more radicals selected from the group consisting of halogen, nitro, cyano, (C$_1$–C$_4$)alkyl, (C$_1$–C$_4$)alkoxy, (C$_1$–C$_4$)alkylthio, (C$_1$–C$_4$)haloalkyl, (C$_1$–C$_4$)haloalkoxy, formyl, (C$_1$–C$_4$)alkylcarbonyl, (C$_1$–C$_4$)alkoxycarbonyl, (C$_1$–C$_4$)alkoxy, where heterocyclyl in the radicals contains in each case 3 to 9 ring atoms and 1 to 3 hetero ring atoms selected from the group consisting of N, O and S, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$alkyl and oxo.

$(X)_n$ is especially preferably n substituents X and where X in each case independently of one another are halogen, OH, $NO_2$, CN, $SCN(C_1-C_6)$alkyl, $(C_1-C_6)$alkoxy, $(C_1-C_4)$alkylcarbonyl or $(C_1-C_4)$alkyloxycarbonyl, where the last-mentioned four radicals are unsubstituted or substituted by halogen or $(C_1-C_4)$alkoxy, and very especially preferably n substituents X and where X in each case independently of one another are halogen, hydroxyl, $(C_1-C_4)$alkyl or $(C_1-C_4)$alkoxy.

Heterocyclyl in the radicals mentioned hereinabove or further below are, independently of one another preferably a heterocyclic radical having 3 to 7 ring atoms selected from the group consisting of N, O and S, preferably a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl or a partially or fully hydrogenated heterocyclic radical selected from the group consisting of oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl.

Especially preferably, heterocyclyl is a heterocyclic radical having 3 to 6 ring atoms and one (1) hetero atom selected from the group consisting of N, O and S, in particular a heteroaromatic radical having 5 or 6 ring atoms or a saturated or partially unsaturated heterocyclic (not heteroaromatic) radical having 3 to 6 ring atoms.

Moreover, heterocyclyl is preferably a heterocyclic radical having 5 or 6 ring atoms and 2 or 3 hetero atoms selected from the group consisting of N, O and S, in particular pyrimidinyl, pyridazinyl, pyrazinyl, triazinyl, thiazolyl, thiadiazolyl, oxazolyl, isoxazolyl, pyrazolyl, imidazolyl, triazolyl or piperazinyl, dioxolanyl, oxazolinyl, isoxazolinyl, oxazolidinyl, isoxazolidinyl or morpholinyl.

The composite group $-A^2-R^2$ is preferably cyclopropyl (hereinbelow also "c-Pr"), $CH_2$-c-Pr, $-(CH_2)_2$-Pr, cyclobutyl (hereinbelow also "c-Bu"), $CH_2$-c-Bu; $(CH_2)_2$-c-Bu, oxiranyl, oxiranylmethyl or 2-(oxiranyl)-eth-1-yl.

Subject matter of the present invention are also processes for the preparation of compounds of the formula (I) and their salts

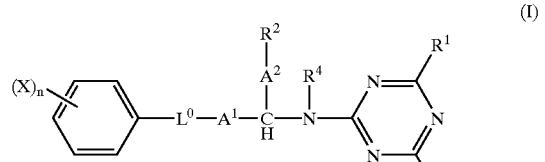

(I)

where $A^1$, $A^2$, $L^0$, $R^1$, $R^2$, $R^3$, $R^4$, X and n are as defined hereinabove, wherein a) in the event that $R^3$ in formula (I) is a group of the formula $-L^1-N=C(U^1)(U^3)$, where $L^1$, $U^1$ and $U^3$ are as defined further above under $R^3$, a compound of the formula (II)

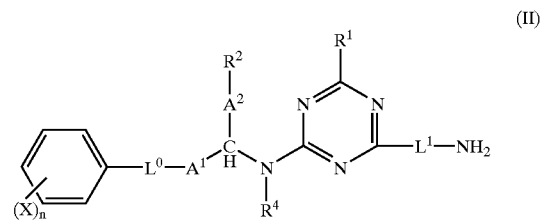

(II)

where $A^1$, $A^2$, $L^0$, $L^1$, $R^1$, $R^2$, $R^4$, X and n are as defined in formula (I) is reacted with a compound of the formula (III)

(III)

where $U^1$ and $U^3$ are as defined in formula (I) and $R^{18}$ and $R^{19}$ independently of one another are unsubstituted or substituted alkyl having up to 12 carbon atoms, preferably $(C_1-C_4)$alkyl, or jointly linked are an alkylene group having 2 to 4 carbon atoms, or b) in the event that $R^3$ in formula (I) is a group of the formula $L^1$-$NG^1$—$C(U^2)$=$N$—$U^4$ where $L^1$, $G^1$, $U^2$ and $U^4$ are as defined further above under $R^3$, a compound of the formula (IV)

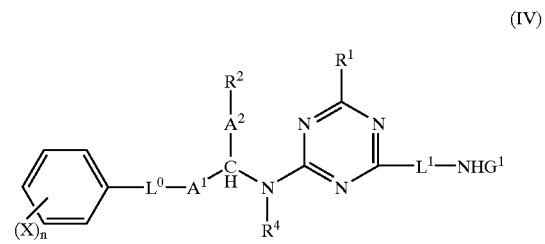

(IV)

where $A^1$, $A^2$, $L^0$, $L^1$, $R^1$, $R^2$, $R^4$, $G^1$, X and n are as defined in formula (I) is reacted with a compound of the formula (V)

(V)

where $U^2$ and $U^4$ are as defined in formula (I) and $R^{18}$ is as defined in formula (III), or c) in the event that $R^3$ in formula (I) is a group of the formula -$L^1$—$N=C(U^1)(U^3)$ where $U^3$=$NG^{18}NG^{19}G^{20}$, $NG^{21}OG^{22}$ or $NG^{23}SG^{24}$ and $L^1$, $U^1$, $G^{18}$, $G^{19}$, $G^{20}$, $G^{21}$, $G^{22}$, $G^{23}$, $G^{24}$ are as defined further above under $R^3$, a compound of the formula (VI)

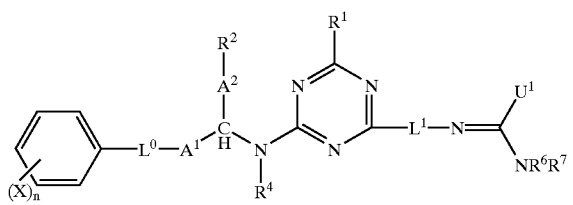
(VI)

where $A^1$, $A^2$, $L^0$, $L^1$, $R^1$, $R^2$, $R^4$, $U^1$, X and n are as defined in formula (I) and $R^6$ and $R^7$ are as defined further above, is reacted with a compound of the formula (VII) or its acid adducts

H—$U^3$ (VII)

where $U^3$ is as defined in formula (I), or d) in the event that $R^3$ in formula (I) is a group of the formula -$L^1$—N=C($U^1$)($U^3$) where $U^1$=$R^{14}$ and $U^3$=$R^{15}$ and $L^1$, $R^{14}$ and $R^{15}$ are as defined further above, a compound of the formula (II) is reacted in accordance with variant a) with an aldehyde or ketone of the formula (VIII)

$U^1$—CO—$U^3$ (VIII)

where $U^1$ and $U^3$ are as defined in formula (I).

The substituted aminotriazines of the formula (II) used in the process according to the invention, variant a) for the preparation of compounds of the formula (I) are known and/or can be prepared by processes known per se (cf. WO-A-9965882). The starting materials of the formula (III) are known (cf. Chem. Ber. 89, 2060 (1956), Liebigs Anm. Chem. 641, 1 (1961), Chem. Ber. 96, 1350 (1963)) or can be prepared analogously to the known processes.

If appropriate, variant a) of the process according to the invention for the preparation of compounds of the formula (I) is carried out using a diluent. Suitable diluents for this purpose are, mainly, inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran, ethylene glycol dimethyl ether or ethylene glycol diethyl ether; ketones such as acetone, butanone or methyl isobutyl ketone; nitriles such as acetonitrile, propionitrile or butyronitrile; amides such as N,N-dimethylformamide, N,N-dimethylacetamide, N-methylformanilide, N-methylpyrrolidone or hexamethylphosphoric triamide; esters such as methyl acetate or ethyl acetate, sulfoxides such as dimethyl sulfoxide, alcohols such as methanol, ethanol, n- or i-propanol, ethylene glycol monomethyl ether, ethylene glycol monoethyl ether, diethylene glycol monomethyl ether or diethylene glycol monoethyl ether. When carrying out the process according to the invention, the reaction temperatures can be varied within a substantial range. In general, the process is carried out at temperatures between 0° C. and 150° C., preferably between 10° C. and 120° C.

As a rule, the process according to the invention is carried out under atmospheric pressure. However, it is also possible to carry out the process according to the invention under elevated or reduced pressure, in general between 0.1 bar and 10 bar.

To carry out the process according to the invention, the starting materials are employed in, for example, equimolar amounts. However, it is also possible to use one of the components in a more or less large excess, for example when the component of which substoichiometric amounts are used is to complete its reaction quickly in order to reduce side reactions. The reaction is carried out for example in a suitable diluent in the presence of a reaction auxiliary, the reaction mixture generally being mixed, for example stirred, for several hours at the temperature required. Work-up can be carried out by customary methods (cf. also the Preparation Examples).

The substituted aminotriazines of the formula (IV) used in variant b) of the process according to the invention for the preparation of compounds of the formula (I) are known and/or can be prepared by processes known per se (cf. WO-A-9965882).

The compounds of the formula (V) are known, for example, from J. Org. Chem. 30, pp. 2531–2533 (1965).

If appropriate, variant b) of the process according to the invention for the preparation of compounds of the formula (I) is carried out using a diluent. Suitable diluents for this purpose are, mainly, inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran, ethylene glycol dimethyl ether or ethylene glycol diethyl ether; ketones such as acetone, butanone or methyl isobutyl ketone; nitriles such as acetonitrile, propionitrile or butyronitrile; amides such as N,N-dimethylformamide, N,N-dimethylacetamide, N-methylformanilide, N-methylpyrrolidone or hexamethylphosphoric triamide; esters such as methyl acetate or ethyl acetate, sulfoxides such as dimethyl sulfoxide, alcohols such as methanol, ethanol, n- or i-propanol, ethylene glycol monomethyl ether, ethylene glycol monoethyl ether, diethylene glycol monomethyl ether or diethylene glycol monoethyl ether.

When carrying out the process according to the invention, the reaction temperatures can be varied within a substantial range. In general, the process is carried out at temperatures between 0° C. and 150° C., preferably between 10° C. and 120° C.

Variant b) of the process according to the invention is carried out in a simple manner, for example under atmospheric pressure. However, it is also possible to carry out the process according to the invention under elevated or reduced pressure, preferably between 0.1 bar and 10 bar.

To carry out variant b) of the process, the starting materials can be employed in equimolar amounts. However, it is also possible to use one of the components in a more or less large excess. The reaction is preferably carried out in a suitable diluent in the presence of a reaction auxiliary. As a rule, the reaction proceeds to completion in the course of several hours with stirring at the temperature required. Work-up can be carried out by customary methods (cf. the Preparation Examples).

To prepare the compounds (I) following variant c), compounds of the formula (VI) are employed. Compounds of the formula (VI) can be prepared from amino compounds of the formula (II) following variant a), for example by reaction with compounds of the formula (III) where $U^1$, $R^{18}$, $R^{19}$ are as defined in formula (III) and $U^3$=$NR^6R^7$, where $R^6$ and $R^7$ are as defined in formula (I) (=Compounds (IIIa)). The compounds of the formula (VII) are known or can be prepared by known methods. If appropriate, variant c) of the process according to the invention is carried out using a diluent. Suitable diluents for this purpose are, mainly, inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran, ethylene glycol dimethyl ether or ethylene glycol diethyl ether; ketones such as acetone, butanone or methyl isobutyl ketone; nitriles such as acetonitrile, propionitrile or butyronitrile; amides such as N,N-dimethylformamide, N,N-dimethylacetamide, N-methylformanilide, N-methylpyrrolidone or hexamethylphosphoric triamide; esters such as methyl acetate or ethyl acetate, sulfoxides such as dimethyl sulfoxide, alcohols such as methanol, ethanol, n- or i-propanol, ethylene glycol monomethyl ether, ethylene glycol monoethyl ether, diethylene glycol monomethyl ether or diethylene glycol monoethyl ether.

The other reaction conditions, such as ranges for reaction temperatures, pressure conditions, proportions and the like are similar to those in variants a) and b).

If appropriate, variant d) of the process according to the invention is carried out using a diluent. Suitable diluents for this purpose are, mainly, inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran, ethylene glycol dimethyl ether or ethylene glycol diethyl ether; ketones such as acetone, butanone or methyl isobutyl ketone; nitriles such as acetonitrile, propionitrile or butyronitrile; amides such as N,N-dimethylformamide, N,N-dimethylacetamide, N-methylformanilide, N-methylpyrrolidone or hexamethylphosphoric triamide; esters such as methyl acetate or ethyl acetate; sulfoxides such as dimethyl sulfoxide, alcohols such as methanol, ethanol, n- or i-propanol, ethylene glycol monomethyl ether, ethylene glycol monoethyl ether, diethylene glycol monomethyl ether or diethylene glycol monoethyl ether.

The compounds of the formula (VIII) which are employed in variant d) of the process are known or can be prepared by known methods.

The other reaction conditions, such as ranges for reaction temperatures, pressure conditions, proportions and the like are similar to those in variants a) and b) and c).

The water which is liberated during the reaction (reaction water) can be removed for example by azeotropic distillation, water-binding salts or molecular sieves.

The respective starting compounds of the formulae (II) to (VIII) are known or can be prepared by the abovementioned methods or analogously to known processes.

The following acids are suitable for preparing the acid addition salts of the compounds of the formula (I): hydrohalic acids such as hydrochloric acid or hydrobromic acid, furthermore phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition compounds of the formula (I) can be obtained simply by the customary salt formation methods, for example by dissolving a compound of the formula (I) in a suitable organic solvent such as, for example, methanol, acetone, methylene chloride or benzine, and adding the acid at temperatures of from 0 to 100° C., and they can be isolated in a known fashion, for example by filtration, and, if appropriate, purified by washing with an inert organic solvent.

The base addition salts of the compounds of the formula (I) are preferably prepared in inert polar solvents such as, for example, water, methanol or acetone at temperature from 0 to 100° C. Examples of suitable bases for preparing the salts according to the invention are alkali metal carbonates, such as potassium carbonate, alkali metal and alkaline earth metal hydroxides, for example NaOH or KOH, alkali metal and alkaline earth metal hydrides, for example NaH, alkali metal and alkaline earth metal alkoxides, for example sodium methoxide, potassium tert-butoxide, or ammonia or ethanolamine. Quaternary ammonium salts can be obtained, for example, by salt exchange or condensation with quaternary ammonium salts of the formula $[NRR'R''R''']^+X^-$ where R, R', R" and R"' independently of one another are $(C_1-C_4)$ alkyl, phenyl or benzyl and X is an anion, for example $Cl^-$ or $OH^-$.

The "inert solvents" which the above process variants refer to are to be understood as meaning in each case solvents which are inert under the reaction conditions in question, but which need not be inert under any desired reaction conditions.

A collection of compounds (I) which can be synthesized by the above-mentioned processes can additionally be prepared in parallelized fashion, which can be effected manually, partly automated or fully automated. In this context, it is possible to automate the procedure of the reaction, work-up or purification of the products or intermediates. In total, this is to be understood as meaning a procedure which is described, for example, by S. H. DeWitt in "Annual Reports in Combinatorial Chemistry and Molecular Diversity: Automated Synthesis", Volume 1, published by Escom, 1997, pages 69 to 77.

For carrying out the reaction and work-up in parallelized fashion, a series of commercially available apparatuses can be used as they are available from, for example, Stem Corporation, Woodrolfe Road, Tollesbury, Essex, CM9 8SE, England or H+P Labortechnik GmbH, Bruckmannring 28,85764 Oberschleißheim, Germany. To carry out the parallelized purification of compounds (I) or of intermediates obtained during the preparation, there are available, inter alia, chromatographic equipment, for example from ISCO, Inc., 4700 Superior Street, Lincoln, Nebr. 68504, USA. The equipment mentioned makes possible a modular procedure, where the individual steps are automated, but manual operation has to be carried out between the steps. This can be circumvented by employing partly or fully integrated automation systems, in which the automation modules in question are operated by, for example, robots. Such automation systems can be obtained from, for example, Zymark Corporation, Zymark Center, Hopkinton, Mass. 01748, USA.

In addition to the above-described methods, compounds (I) can be prepared in full or partly by solid-phase supported methods. To this end, individual intermediates or all intermediates of the synthesis or of a synthesis adapted to the procedure in question are bound to a synthesis resin. Solid-phase supported synthetic methods are described extensively in the specialist literature, for example: Barry A. Bunin in "The Combinatorial Index", published by Academic Press, 1998.

The use of solid-phase supported synthesis methods permits a series of protocols known from the literature which, in turn, can be carried out manually or in an automated fashion. For example, the "teabag method" (Houghten, U.S. Pat. No. 4,631,211; Houghten et al., Proc. Natl. Acad. Sci., 1985, 82, 5131–5135) can be partly automated with products of IRORI, 11149 North Torrey Pines Road, La Jolla, Calif. 92037, USA. Solid-phase supported parallel synthesis can be automated successfully for example using equipment by Argonaut Technologies, Inc., 887 Industrial Road, San Carlos, Calif. 94070, USA or MultiSynTech GmbH, Wullener Feld 4, 58454 Witten, Germany.

The preparation in accordance with the processes described herein yields compounds (I) in the form of substance collections or substance libraries. Subject matter of the present invention are therefore also libraries of the compounds (I) which contain at least two compounds (I), and of their precursors.

The compounds of the formula (I) according to the invention and their salts, hereinbelow together termed compounds of the formula (I) (according to the invention) have an excellent herbicidal activity against a broad spectrum of economically important mono- and dicotyledonous harmful plants. The active substances also act efficiently on perennial weeds which produce shoots from rhizomes, root stocks or other perennial organs and are difficult to control. In this context, it is unimportant whether the substances are applied before sowing, preemergence or postemergence.

Specifically, some representatives of the mono- and dicotyledonous weed flora which can be controlled by the compounds according to the invention may be mentioned by way of example, without a restriction to certain species being intended to take place as a result of the mention.

Amongst the monocotyledonous weed species, those on which the active substances act efficiently are, for example, Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea and Cyperus species from the annual group and, amongst the perennial species, Agropyron, Cynodon, Imperata and Sorghum and also perennial Cyperus species. In the case of dicotyledonous weed species, the spectrum of action extends to species such as, for example, Galium, Viola, Veronica, Lamium, Stellaria, Amaranthus, Sinapis, Ipomoea, Matricaria, Abutilon and Sida amongst the annuals and Convolvulus, Cirsium, Rumex and Artemisia in the case of the perennial weeds. Herbicidal action is also achieved in the case of dicotyledonous harmful plants such as Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica and Xanthium.

Harmful plants occurring under the specific cultivation conditions of rice, such as, for example, Sagittaria, Alisma, Eleocharis, Scirpus and Cyperus, are also outstandingly well controlled by the active substances according to the invention.

If the compounds according to the invention are applied to the soil surface before germination, then the weed seedlings are either prevented completely from emerging or the weeds grow until they have reached the cotyledon stage, but then their growth stops and they finally die completely after three to four weeks have elapsed. When the active substances are applied postemergence to the green parts of the plants, growth stops equally drastically a very short time after treatment and the weed plants remain at the stage of growth at the time of application, or they die completely after a certain time, so that in this manner competition by the weeds, which is harmful to the crop plants, is eliminated at a very early stage and in a sustained manner.

Although the compounds according to the invention have an excellent herbicidal activity against mono- and dicotyledonous weeds, crop plants of economically important crops such as, for example, wheat, barley, rye, triticale, rice, maize, sugar beet, cotton and soybeans, are damaged only to an insignificant extent or not at all. For these reasons, the present compounds are very highly suitable for the selective control of undesired vegetation in stands of agriculturally useful plants or in stands of ornamental plants.

In addition, the substances according to the invention have outstanding growth-regulatory properties in crop plants. They engage in the plants' metabolism in a regulatory fashion and can thus be employed for influencing plant constituents in a targeted fashion and for facilitating harvesting, such as, for example, by triggering desiccation and stunted growth. Moreover, they are also suitable for generally controlling and inhibiting undesired vegetative growth without simultaneously killing the plants. Inhibiting vegetative growth plays an important role in many monocotyledonous and dicotyledonous crops since lodging can be reduced, or prevented completely, hereby.

On account of their herbicidal and plant growth-regulatory properties, the active substances can also be employed for the control of harmful plants in crops of known genetically modified plants or genetically modified plants yet to be developed. As a rule, the transgenic plants are distinguished by particularly advantageous properties, for example by resistances to certain pesticides, especially certain herbicides, resistances to plant diseases or pathogens of plant diseases such as certain insects or microorganisms such as fungi, bacteria or viruses. Other particular properties relate, for example, to the harvested material with respect to quantity, quality, storability, composition and specific constituents. Thus, transgenic plants having an increased starch content or where the quality of the starch is altered or those having a different fatty acid composition of the harvested material are known.

The compounds of the formula (I) according to the invention or their salts are preferably used in economically important transgenic crops of useful and ornamental plants, e.g. of cereals such as wheat, barley, rye, oats, sorghum and millet, rice, cassaya and corn or alternatively crops of sugar beet, cotton, soybeans, oilseed rape, potatoes, tomatoes, peas and other types of vegetables.

The compounds of the formula (I) can preferably be employed as herbicides in useful plant crops which are resistant, or have been made resistant, by recombinant methods, to the phytotoxic effects of the herbicides.

Traditional ways of generating novel plants which have modified characteristics in comparison with existing plants consist, for example, in traditional breeding methods and the generation of mutants. Alternatively, novel plants with modified characteristics can be generated using recombinant procedures (see, for example, EP-A-0221044, EP-A-0131624). For example, a number of cases have been described of recombinant modifications of crop plants for the purpose of modifying the starch synthesized in the plants (e.g. WO 92/11376, WO 92/14827, WO 91/19806), transgenic crop plants which are resistant to certain herbicides of the glufosinate type (cf., for example, EP-A-

0242236, EP-A-242246) or of the glyphosate type (WO 92/00377) or of the sulfonylurea type (EP-A-0257993, U.S. Pat. No. 5,013,659), transgenic crop plants, for example cotton, with the capability of producing Bacillus thuringiensis toxins (Bt toxins) which make the plants resistant to certain pests (EP-A-0142924, EP-A-0193259), transgenic crop plants having a modified fatty acid composition (WO 91/13972).

Numerous molecular biology techniques using which novel transgenic plants having modified properties can be produced are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim, 2nd Edition, 1996 or Christou, "Trends in Plant Science" 1 (1996)423–431).

For recombinant manipulations of this type, nucleic acid molecules can be introduced into plasmids which allow mutagenesis or a sequence modification by means of recombination of DNA sequences. With the aid of the abovementioned standard procedures, it is possible, for example, to perform base exchanges, to remove subsequences or to add natural or synthetic sequences. For the connection of the DNA fragments to one another, adaptors or linkers can be attached to the fragments.

For example, plant cells having a reduced activity of a gene product can be produced by the expression of at least one corresponding antisense RNA, a sense RNA to achieve a cosuppression effect or the expression of at least one appropriately constructed ribozyme which specifically cleaves transcripts of the abovementioned gene product.

For this, it is possible to use, on the one hand, DNA molecules which comprise the entire coding sequence of a gene product including flanking sequences which may be present, and also DNA molecules which only comprise parts of the coding sequence, where these parts must be long enough in order to bring about an antisense effect in the cells. The use of DNA sequences which have a high degree of homology to the coding sequences of a gene product, but are not completely identical, is also possible.

When nucleic acid molecules are expressed in plants, the synthesized protein can be localized in any desired compartment of the plant cell. However, in order to achieve localization in a certain compartment, it is possible, for example, to link the coding region with DNA sequences which guarantee localization in a certain compartment. Sequences of this type are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated to give intact plants according to known techniques. In principle, the transgenic plants can be plants of any desired plant species, i.e. both monocotyledonous and dicotyledonous plants. Transgenic plants are thus obtainable which have modified properties as a result of overexpression, suppression or inhibition of homologous (=natural) genes or gene sequences or expression of heterologous (=foreign) genes or gene sequences.

The compounds (I) according to the invention can preferably be employed in transgenic crops which are resistant to herbicides from the group consisting of the sulfonylureas, glufosinate-ammonium or glyphosate-isopropylammonium and analogous active substances.

When the active substances according to the invention are used in transgenic crops, in addition to the effects against harmful plants to be observed in other crops, effects often occur which are specific for application in the particular transgenic crop, for example a modified or specifically widened spectrum of weeds which can be controlled, altered application rates which can be employed for application, preferably good combining ability with the herbicides to which the transgenic crop is resistant, and an effect on growth and yield of the transgenic crop plants.

The invention therefore also relates to the use of the compounds (I) according to the invention as herbicides for controlling harmful plants in transgenic crop plants.

The use according to the invention for controlling harmful plants or for regulating the growth of plants also includes the case where the active substance of the formula (I) or its salt is formed from a prodrug only after application on the plant, in the plant or in the soil.

The compounds according to the invention can be used in the customary preparations in the form of wettable powders, emulsifiable concentrates, sprayable solutions, dusting agents or granules. The invention therefore also relates to herbicidal and plant growth-regulating compositions which contain compounds of the formula (I).

The compounds of the formula (I) can be formulated in various ways, depending on what biological and/or chemicophysical parameters are prespecified. Examples of suitable formulation possibilities are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions on an oil or water basis, oil-miscible solutions, capsule suspensions (CS), dusting agents (DP), dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hauser Verlag Munich, 4th Edition 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary or applicable formulation auxiliaries such as inert materials, surfactants, solvents and other additives are also in many cases known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Edition 1986.

On the basis of these formulations, combinations with other pesticidally active substances such as, for example, insecticides, acaricides, herbicides, fungicides, and also with safeners, fertilizers and/or growth regulators can also be prepared, e.g. in the form of a finished formulation or as a tank mix.

Wettable powders are preparations which are uniformly dispersible in water and which, besides the active compound, also contain surfactants of ionic and/or nonionic type (wetting agents, dispersants), e.g. polyoxyethylated alkylphenols, polyoxethylated fatty alcohols, polyoxethylated fatty amines, fatty alcohol polyglycol ether sulfates, alkanesulfonates, alkylbenzenesulfonates, sodium lignosulfonates, sodium 2,2'-dinaphthylmethane-6,6'-disulfonate, sodium dibutylnaphthalene-sulfonate or alternatively sodium oleoylmethyltaurate in addition to a diluent or inert substance. For preparation of the wettable powders, the herbicidal active substances are finely ground, for example, in customary equipment such as hammer mills, blowing mills and air-jet mills and simultaneously or subsequently mixed with the formulation auxiliaries.

Emulsifiable concentrates are prepared by dissolving the active substance in an organic solvent, e.g. butanol, cyclohexanone, dimethylformamide, xylene or alternatively relatively high-boiling aromatics or hydrocarbons or mixtures of the organic solvents with addition of one or more surfactants of ionic and/or nonionic type (emulsifiers). Examples of emulsifiers which can be used are: alkylarylsulfonic acid calcium salts such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters such as, for example, sorbitan fatty acid esters or polyoxyethylene sorbitan esters such as, for example, polyoxyethylene sorbitan fatty acid esters.

Dusting agents are obtained by grinding the active substance with finely divided solid substances, e.g. talc, natural clays, such as kaolin, bentonite and pyrophyllite, or diatomaceous earth.

Suspension concentrates can be water- or oil-based. They can be prepared, for example, by wet grinding by means of commercially available bead mills and, if appropriate, addition of surfactants, such as have already been mentioned, for example, above in the case of the other formulation types.

Emulsions, e.g. oil-in-water emulsions (EW), can be prepared, for example, by means of stirrers, colloid mills and/or static mixers using aqueous organic solvents and, if appropriate, surfactants, such as have already been mentioned, for example, above in the case of the other formulation types.

Granules can either be prepared by spraying the active substance onto adsorptive, granulated inert material or by applying active substance concentrates to the surface of carriers such as sand, kaolinites or of granulated inert material by means of binders, e.g. polyvinyl alcohol, sodium polyacrylate or alternatively mineral oils. Suitable active substances can also be granulated in the manner customary for the preparation of fertilizer granules—if desired as a mixture with fertilizers.

As a rule, water-dispersible granules are prepared by the customary processes such as spray-drying, fluidized bed granulation, disk granulation, mixing using high-speed mixers and extrusion without solid inert material. For the preparation of disk, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8–57.

For further details on the formulation of plant protection materials see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations contain 0.1 to 99% by weight, in particular 0.1 to 95% by weight, of active substance of the formula (I). In wettable powders, the active substance concentration is, for example, approximately 10 to 90% by weight, the remainder to 100% by weight consists of customary formulation constituents. In the case of emulsifiable concentrates, the active substance concentration can be approximately 1 to 90, preferably 5 to 80, % by weight. Formulations in the form of dusts contain 1 to 30% by weight of active substance, preferably usually 5 to 20% by weight of active substance, sprayable solutions contain approximately 0.05 to 80, preferably 2 to 50, % by weight of active substance. In the case of water-dispersible granules, the active substance content depends partly on whether the active compound is liquid or solid and which granulation auxiliaries, fillers etc. are used. In the case of water-dispersible granules, the content of active substance is, for example, between 1 and 95% by weight, preferably between 10 and 80% by weight.

In addition, the active substance formulations mentioned optionally contain the binders, wetting agents, dispersants, emulsifiers, penetrants, preservatives, antifreeze agents, solvents, fillers, carriers, colorants, antifoams, evaporation inhibitors and the pH and viscosity regulators which are customary in each case.

The compounds of the formula (I) or their salts can be employed as such or in the form of their preparations (formulations) as combinations with other pesticidally active substances, such as, for example, insecticides, acaricides, nematicides, herbicides, fungicides, safeners, fertilizers and/or growth regulators, for example as a premix or as tank mixes.

Components which may be employed for the active substances according to the invention in mixed formulations or in tank mix are, for example, known active compounds which are based on an inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other compounds which can be employed, whose mechanism of action is to a degree unknown or different, are described, for example, in Weed Research 26, 441–445 (1986), or "The Pesticide Manual", 11th Edition 1997 (hereinbelow also abbreviated to "PM") and 12th Edition 2000, The British Crop Protection Council and the Royal Soc. of Chemistry (editors) and literature cited therein. Herbicides which are known from the literature and which can be mentioned, which can be combined with the compounds of the formula (I), are, for example, the following active substances (Note: the compounds are either designated by the common name according to the International Organization for Standardization (ISO) or using the chemical name, if appropriate together with a customary code number): acetochlor; acifluorfen(-sodium); aclonifen; AKH 7088, i.e. [[[1-[5-[2-chloro-4-(trifluoromethyl) phenoxy]-2-nitrophenyl]-2-methoxyethylidene]amino]oxy] acetic acid and its methyl ester; alachlor; alloxydim(-sodium); ametryn; amicarbazone, amidochlor, amidosulfuron; amatory; AMS, i.e. ammonium sulfamate; anilofos; asulam; atrazin; azafenidin, azimsulfurone (DPX-A8947); aziprotryn; barban; BAS 516H, i.e. 5-fluoro-2-phenyl-4H-3,1-benzoxazin-4-one; beflubutamid, benazolin (-ethyl); benfluralin; benfuresate; bensulfuron(-methyl); bensulide; bentazone; benzobicyclon, benzofenap; benzofluor; benzoylprop(-ethyl); benzthiazuron; bialaphos; bifenox; bispyribac(-sodium), bromacil; bromobutide; bromofenoxim; bromoxynil; bromuron; buminafos; busoxinone; butachlor; butafenacil, butamifos; butenachlor; buthidazole; butralin; butroxydim, butylate; cafenstrole (CH-900); carbetamide; carfentrazone(-ethyl) (ICI-A0051); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecolmethyl; chloridazon; chlorimuron(-ethyl); chlomitrofen; chlorotoluron; chloroxuron; chlorpropham; chlorsulfuron; chlorthal-dimethyl; chlorthiamid; chlortoluron, cinidon(-methyl and -ethyl), cinmethylin; cinosulfuron; clefoxydim, clethodim; clodinafop and its ester derivatives (for example clodinafop-propargyl); clomazone; clomeprop; cloproxydim; clopyralid; clopyrasulfuron(-methyl), cloransulam(-methyl), cumyluron (JC 940); cyanazine; cycloate; cyclosulfamuron (AC 104); cycloxydim; cycluron; cyhalofop and its ester derivatives (for example the butyl ester, DEH-112); cyperquat; cyprazine; cyprazole; daimuron; 2,4-D, 2,4-DB; 2,4-DB, dalapon; desmedipham; desmetryn; di-allate; dicamba; dichlobenil; dichlorprop; diclofop and its esters such as diclofop-methyl; diclosulam, diethatyl(-ethyl); difenoxuron; difenzoquat; diflufenican; diflufenzopyr, dimefuron; dimepiperate, dimethachlor; dimethametryn; dimethenamid (SAN-582H); dimethazone, dimexyflam, dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example the ethyl ester, HN-252); ethoxysulfuron, etobenzanid (HW 52); F5231, i.e. N-[2-chloro-4-fluoro-5-[4-(3-fluoropropyl)4,5-dihydro-5-oxo-1H-tetrazol-1-yl]phenyl] ethanesulfon amide; fenoprop; fenoxan, fenoxaprop and fenoxaprop-P and their esters, for example fenoxaprop-P-ethyl and fenoxaprop-ethyl; fenoxydim; fentrazamide, fenuron; flamprop(-methyl or -isopropyl or -isopropyl-L); flazasulfuron; floazulate, florasulam, fluazifop and fluazifop-P and their esters, for example fluazifop-butyl and fluazifop-P-butyl; flucarbazone(-sodium), fluchloralin; flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupyrsulfuron(-methyl or -sodium), flurenol (-butyl), fluridone; flurochloridone; fluroxypyr(-meptyl); flurprimidol, flurtamone; fluthiacet(-methyl), fluthiamide, fomesafen; foramsulfuron, fosamine; furyloxyfen; glufosinate(-ammonium); glyphosate(-isopropylammonium); halosafen; halosulfuron(-methyl) and its esters (for example the methyl ester, NC-319); haloxyfop and its esters; haloxyfop-P (=R-haloxyfop) and its esters; hexazinone; imazamethabenz(-methyl); imazapyr; imazaquin and salts such as the ammonium salt; imazamethapyr, imazamox, imazapic, imazethamethapyr; imazethapyr; imazosulfuron; indanofan, ioxynil; isocarbamid; isopropalin; isoproturon; isouron; isoxaben; isoxachlortole, isoxaflutole, isoxapyrifop; karbutilate; lactofen; lenacil; linuron; MCPA; MCPB; mecoprop; mefenacet; mefluidid; mesosulfuron, mesotrione, metamitron; metazachlor; methabenzthiazuron; metham; methazole; methoxyphenone; methyldymron; metabenzuron, methobenzuron; metobromuron; (alpha-) metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron, oxaziclomefone, oxyfluorfen; paraquat; pebulate; pelargonic acid, pendimethalin, pentoxazone, perfluidone; phenisopham; phenmedipham; picloram; picolinafen, piperophos; piributicarb; pirifenopbutyl; pretilachlor; primisulfuron(-methyl); procarbazone(-sodium), procyazine; prodiamine; profluralin; proglinazine (-ethyl); prometon; prometryn; propachlor; propanil; propaquizafop and its esters; propazine; propham; propisochlor; propyzamide; prosulfalin; prosulfocarb; prosulfuron (CGA-152005); prynachlor; pyraflufen(-ethyl), pyrazolinate; pyrazon; pyrazosulfuron(-ethyl); pyrazoxyfen; pyribenzoxim, pyributicarb, pyridafol, pyridate; pyrimidobac(-methyl), pyrithiobac(-sodium) (KIH-2031); pyroxofop and its esters (for example the propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4, 5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; sulcotrione, sulfentrazon (FMC-97285, F-6285); sulfazuron; sulfometuron(-methyl); sulfosate (ICI-A0224); sulfosulfuron, TCA; tebutam (GCP-5544); tebuthiuron; tepraloxydim, terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide, thiazafluron; thiazopyr (Mon-13200); thidiazimin (SN-24085); thifensulfuron (-methyl); thiobencarb; tiocarbazil; tralkoxydim; tri-allate; triasulfuron; triaziflam, triazofenamide; tribenuron(-methyl); triclopyr; tridiphane; trietazine; trifluralin; triflusulfuron and its esters (for example the methyl ester, DPX-66037); trimeturon; tritosulfuron, tsitodef; vernolate; WL 110547, i.e. 5-phenoxy-1-[3-(trifluoromethyl)phenyl]-1H-tetrazole; BAY MKH 6561, UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

Controlling harmful plants selectively is of particular interest in crops of useful plants and ornamentals. Even though the compounds (I) already exhibit very good to sufficient selectivity in many crops, it is possible, in principle, that symptoms of phytotoxicity occur on the cultivated plants in some crops and especially also in the case of mixtures with other herbicides which are less selective. In this respect, combinations of compounds (I) according to the invention which are of particular interest are those which contain the compounds (I) or their combinations with other herbicides or pesticides and safeners. The safeners, which are employed in such an amount that they act as antidote, reduce the phytotoxic side effects of the herbicides/pesticides employed, for example in economically important crops such as cereals (wheat, barley, rye, maize, rice, sorghum and millet), sugar beet, sugar cane, oilseed rape, cotton and soybeans, preferably cereals. The following groups of compounds are examples of suitable safeners for the compounds (I) and their combinations with further pesticides:

a) compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (S1-1) ("Mefenpyr-diethyl", PM, pp. 781–782) and related compounds as they are described in WO 91/07874;

b) dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds as they are described in EP-A-333 131 and EP-A-269 806;

c) compounds of the triazolecarboxylic acids type, preferably compounds such as fenchlorazol (and its ethyl ester), i.e. ethyl 1-(2,4-dichlorophenyl)-5-trichloromethyl-(1H)-1,2,4-triazole-3-carboxylate (S1-6), and related compounds (see EP-A-174 562 and EP-A-346 620);

d) compounds of the 5-benzyl- or 5-phenyl-2-isoxazoline-3-carboxylic acid type or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds as they are described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as they are described in German Patent Application (WO-A-95/07897);

e) compounds of the 8-quinolinoxyacetic acid type (S2), preferably 1-methylhex-1-yl (5-chloro-8-quinolinoxy)acetate (common name "cloquintocet-mexyl") (S2-1) (see PM, pp. 263–264) 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminooxy)-1-ethyl (5-chloro-8-quinolinoxy)acetate (S2-8), 2-oxoprop-1-yl (5-chloro-8-quinolinoxy)acetate (S2-9), and related compounds as are described in EP-A-86 750, EP-A-94 349 and EP-A-191 736 or EP-A-0 492 366;

f) compounds of the (5-chloro-8-quinolinoxy)malonic acid type, preferably compounds such as diethyl (5-chloro-8-quinolinoxy)malonate, diallyl (5-chloro-8-quinolinoxy)malonate, methylethyl (5-chloro-8-quinolinoxy)malonate and related compounds as are described in EP-A-0 582 198;

g) active substances of the phenoxyacetic or phenoxypropionic acid derivatives type or of the aromatic carboxylic acids type, such as, for example, 2,4-dichlorophenoxyacetic acids (and its esters) (2,4-D), 4-chloro-2-methylphenoxypropionic esters (mecoprop), MCPA or 3,6-dichloro-2-methoxybenzoic acid (and its esters) (dicamba);

h) active substances of the pyrimidines type which are employed in rice as soil-acting safeners, such as, for example, "fenclorim" (PM, pp. 511–512) (=4,6-dichloro-2-phenylpyrimidine), which is also known as safener for pretilachlor in seeded rice;

i) active substances of the dichloroacetamides type, which are frequently employed as pre-emergence safeners (soil-acting safeners), such as, for example, "dichlormid" (PM, pp. 363–364) (=N,N-diallyl-2,2-dichloroacetamide), "R-29148" (=3-dichloroacetyl-2,2,5-trimethyl-1,3-oxazolidine, by Stauffer), "benoxacor" (PM, pp. 102–103) (=4-dichloroacetyl-3,4-dihydro-3-methyl-2H-1,4-benzoxazine), "PPG-1292" (=N-allyl-N-[(1,3-dioxolan-2-yl)methyl]dichloroacetamide by PPG Industries), "DK-24" (=N-allyl-N-[(allylaminocarbonyl)methyl]dichloroacetamide by Sagro-Chem), "AD-67" or "MON 4660" (=3-dichloroacetyl-1-oxa-3-azaspiro[4,5]decane by Nitrokemia and Monsanto, respectively), "diclonon" or "BAS145138" or "LAB145138" (=3-dichloroacetyl-2,5,5-trimethyl-1,3-diazabicyclo[4.3.0]nonane by BASF) and "furilazol" or "MON 13900" (see PM, 637–638) (=(RS)-3-dichloroacetyl-5-(2-furyl-2,2-dimethyloxazolidine);

j) active substances of the dichloroacetone derivatives type, such as, for example, "MG 191" (CAS Reg. No. 96420-72-3) (=2-dichloromethyl-2-methyl-1,3-dioxolane by Nitrokemia), which is known as safener for maize;

k) active substances of the oxyimino compounds type, which are known as seed treatment products, such as, for example, "oxabetrinil" (PM, pp. 902–903) (=(Z)-1,3-dioxolan-2-ylmethoxyimino(phenyl)-acetonitrile), which is known as seed-treatment safener for sorghum and millet against metolachlor damage, "fluxofenim" (PM, pp. 613–614) (=1-(4-chlorophenyl)-2,2,2-trifluoro-1-ethanone O-(1,3-dioxolan-2-ylmethyl) oxime, which is known as seed-dressing safener for sorghum and millet against metolachlor damage, and "cyometrinil" or "-CGA-43089" (PM, p. 1304) (=(Z)-cyanomethoxyimino(phenyl)acetonitrile), which is known as seed-treatment safener for sorghum and millet against metolachlor damage;

l) active substances of the thiazolecarboxylic ester type, which are known as seed treatment products, such as, for example, "flurazol" (PM, pp. 590–591) (=benzyl 2-chloro-4-trifluoromethyl-1,3-thiazole-5-carboxylate), which is known as seed-treatment safener for sorghum and millet against alachlor and metolachlor damage;

m) active substances of the naphthalenedicarboxylic acid derivatives type, which are known as seed treatment products, such as, for example, "naphthalic anhydride" (PM, p. 1342) (=1,8-naphthalenedicarboxylic anhydride), which is known as seed-treatment safener for maize against thiocarbamate herbicide damage;

n) active substances of the chromanacetic acid derivatives type, such as, for example, "CL 304415" (CAS Reg. No. 31541-57-8) (=2-(4-carboxychroman-4-yl)acetic acid by American Cyanamid), which is known as safener for maize against damage by imidazolinones;

o) active substances which, in addition to a herbicidal action against harmful plants, also exhibit a safener action in connection with crop plants such as rice, such as, for example, "dimepiperate" or "MY-93" (PM, pp. 404–405) (=S-1-methyl-1-phenylethyl piperidine-1-carbothioate), which is known as safener for rice against damage by the herbicide molinate, "daimuron" or "SK 23" (PM, p. 330) (=1-(1-methyl-1-phenylethyl)-3-p-tolylurea), which is known as safener for rice against damage by the herbicide imazosulfuron, "cumyluron"="JC-940" (=3-(2-chlorophenylmethyl)-1-(1-methyl-1-phenylethyl)urea, see JP-A-60087254), which is known as safener for rice against damage by several herbicides, "methoxyphenone" or "NK 049" (=3,3'-dimethyl-4-methoxybenzophenone), which is known as safener for rice against damage by several herbicides, "CSB" (=1-bromo-4-(chloromethylsulfonyl)benzene) (CAS Reg. No. 54091-06-4, by Kumiai), which is known as safener in rice against damage by several herbicides;

p) N-acylsulfonamides of the formula (S3) and their salts

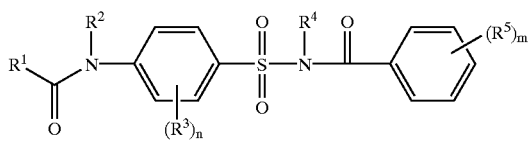

(S3)

as are described in WO-A-97/45016;

q) acylsulfamoylbenzamides of the formula (S4), if appropriate also in salt form,

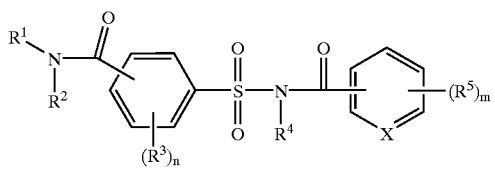

(S4)

as are described in International Application No. PCT/EP98/06097; and r) compounds of the formula (S5),

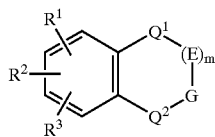

(S5)

as are described in WO-A 98/13 361, including the stereoisomers and the salts conventionally used in agriculture.

Amongst the safeners mentioned, those which are of particular interest are (S1-1) and (S1-9) and (S2-1), in particular (S1-1) and (S1-9).

Some of the safeners are already known as herbicides and therefore simultaneously also display a protective action in connection with the crop plants in addition to the herbicidal action in connection with harmful plants.

The weight ratio of herbicide (mixture) to safener generally depends on the application rate of herbicide and the efficacy of the safener in question; it can vary within wide limits, for example in the range of from 200:1 to 1:200, preferably from 100:1 to 1:100, in particular 20:1 to 1:20. The safeners can be formulated with further herbicides/pesticides, analogously to the compounds (I) or their mixtures, and provided and used as readymix or tank mix together with the herbicides.

For use, the herbicide or herbicide safener formulations, which are present in a customary commercial form, are, if appropriate, diluted in the customary fashion, for example using water in the case of wettable powders, emulsifiable concentrates, dispersions and water-dispersible granules. Preparations in the form of dusts, soil granules, granules for spreading, and sprayable solutions, are usually not diluted further with other inert materials prior to use.

The application rate required of the compounds of the formula (I) varies with, inter alia, the external conditions such as temperature, humidity and the type of the herbicide used. It can vary within wide limits, for example between 0.001 and 10.0 kg/ha or more of active substance, but it is preferably between 0.005 and 5 kg/ha, in particular 0.01 and 3 kg/ha.

In the examples which follow, quantities (also percentages) are weight-based, unless specifically indicated.

A. CHEMICAL EXAMPLES

Example A1

2-Dimethylaminomethyleneamino-4-(1-fluoro-1-methylethyl)-6-(1-cyclopropyl-4-phenyl-1-butylamino)-1,3,5-triazine (see Table 8, Example 8-2)

A solution of 1.71 g (5 mmol) of 2-amino-4-(1-fluoro-1-methylethyl)-6-(1-cyclopropyl-4-phenyl-1-butylamino)-1,3,5-triazine and 2 ml of N,N-dimethylformamide dimethyl acetal in 30 ml of toluene is refluxed for 2 hours. All volatile constituents are subsequently carefully distilled off. This gives 1.94 g (97.5% of theory) of 2-dimethylaminomethyleneamino-4-(1-fluoro-1-methylethyl)-6-(1-cyclopropyl-4-phenyl-1-butylamino)-1,3,5-triazine as colorless oil.

Example A2

N-[4-(1-Fluoro1-methylethyl)-6-(1-cyclopropyl-4-phenyl-1-butylamino)-1,3,5-triazin-2-yl]formamide oxime (see Table 8, Example 8-27)

0.69 g (10 mmol) of hydroxylamine hydrochloride are added with stirring at room temperature to a solution of 1.99 g (5 mmol) of 2-dimethylaminomethyleneamino-4-(1-fluoro-1-methylethyl)-6-(1cyclopropyl-4-phenyl-1-butylamino) -1,3,5-triazine in 20 ml of methanol. The reaction mixture is stirred for 2 hours at room temperature. All volatile constituents are carefully distilled off. The crude product is taken up in methylene chloride. The mixture is washed with water, dried over $Na_2SO_4$ and evaporated in vacuo. This gives 1.81 g (93.7% of theory) of N-[4-(1-fluoro-1-methylethyl)-6-(1-cyclopropyl-4-phenyl-1-butylamino)-1,3,5-triazin-1-yl]formamide oxime as pale yellow oil.

Example A3

2-(4-Chlorobenzylideneamino)-4-(1-fluoro-1-methylethyl)-6-(1-cyclopropyl-4-phenyl-1-butylamino)-1,3,5-triazine (see Table 8, Example 8-37)

A mixture of 2.5 g (7.28 mmol) of 2-amino-4-(1-fluoro-1-methylethyl)-6-(1-cyclopropyl-4-phenyl-1-butylamino)-1,3,5-triazine, 1.08 g (7.70 mmol) of p-chlorobenzaldehyde and 100 mg of p-toluenesulfonic acid in 80 ml of toluene are boiled for 10 hours in a water separator. When cold, all volatile constituents are distilled. The crude product is purified by column chromatography (eluent:toluene/ethyl acetate=85:15). This gives 3.0 g (89% of theory) of 2-(4-chloro-6-benzylideneamino)-4-(1-fluoro-1-methylethyl-)-6-(1-cyclopropyl-4-phenyl-1-butylamino)-1,3,5-triazine as colorless oil.

The compounds described in Tables 1 to 12 hereinbelow are obtained in accordance with, or analogously to, the above Examples A1 to A3 or the methods which have been described in general further above. In the tables, the abbreviations have the following meanings:

| Me = | methyl |
| Et = | ethyl |
| Pr = | propyl |
| i-Pr = | isopropyl |
| c-Pr = | cyclopropyl |
| c-Bu = | cyclobutyl |
| t-Bu = | tertiary butyl |

-continued

| c-hexyl = | cyclohexyl | | |
| A1 = | $(CH_2)_1$ | = | —$CH_2$— |
| Ph = | phenyl | | |
| Bz = | benzyl | | |
| A2 = | $(CH_2)_2$ | = | —$CH_2CH_2$— |
| A3 = | $(CH_2)_3$ | = | —$CH_2CH_2CH_2$— |
| A4 = | $(CH_2)_4$ | = | —$CH_2CH_2CH_2CH_2$— |
| Ac = | $COCH_3$ | = | acetyl |
| Ox = | (oxirane) | = | oxiranyl |
| Ph = | phenyl | | |
| $(X)_n$ = | "—" corresponds to n = 0 | | |

Tables 1 to 11 which follow refer to formula (I) where $L^0$=a direct bond and $R^4$=hydrogen atom:

TABLE 1

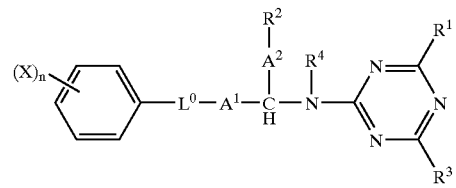

(I)

| No. | $R^1$ | $A^2$—$R^2$ | $R^3$ | $A^1$ | $(X)_n$ | Physical data and stereochemical information |
|---|---|---|---|---|---|---|
| 1-1 | $CH_2OCH_3$ | c-Pr | N=CH—$NMe_2$ | $A^1$ | 4-Cl | racemate |
| 1-2 | $CH(CH_3)(OCH_3)$ | c-Pr | N=CH—$NMe_2$ | $A^1$ | 4-Cl | racemate |
| 1-3 | $CHMe_2$ | c-Pr | N=CH—$NMe_2$ | $A^1$ | 4-F | racemate |
| 1-4 | $CH_2OEt$ | c-Pr | N=C(Et)$NEt_2$ | $A^1$ | 4-Cl | racemate |
| 1-5 | $CH_2CF_3$ | c-Pr | N=C(Ph)($NMe_2$) | $A^1$ | 4-Cl | racemate |
| 1-6 | Ph | c-Bu | N=C(4-MePh)($NMe_2$) | $A^1$ | 4-Br | racemate |
| 1-7 | $CH_2Ph$ | c-Bu- | N=C($CH_2Ph$)($NMe_2$) | $A^1$ | 4-Cl | racemate |
| 1-8 | $CH(CH_3)(CH_2CF_3)$ | c-phenyl | N=C(OMe)($NMe_2$) | $A^1$ | 4-Br | racemate |
| 1-9 | Me | c-Pr | NH—CH=N—OH | $A^1$ | 4-Cl | racemate |
| 1-10 | Et | c-Pr | NH—CH=N—OH | $A^1$ | 2,4-$Cl_2$ | racemate |
| 1-11 | c-Pr | c-Pr | NH—CH=N—$NH_2$ | $A^1$ | 2,4-$Cl_2$ | racemate |
| 1-12 | c-Pr | c-Pr | NH—CH=N—$NMe_2$ | $A^1$ | 2,4,6-$Cl_3$ | racemate |
| 1-13 | c-Bu | $CH_2Ph$ | NHN=CHN(Ph)$_2$ | $A^1$ | 4-Cl | racemate |
| 1-14 | c-Bu | $CH_2Ph$ | N=CHPh | $A^1$ | — | racemate |

TABLE 2

| No. | $R^1$ | $A^2$—$R^2$ | $R^3$ | $A^1$ | $(X)_n$ | Physical data and stereochemical information |
|---|---|---|---|---|---|---|
| 2-1 | $CHMe_2$ | c-Pr | N=CH—$NMe_2$ | $A^2$ | — | racemate, oil |
| 2-2 | CHFMe | c-Pr | N=CH—$NMe_2$ | $A^2$ | 4-J | racemate |
| 2-3 | CHFEt | c-Pr | N=CH—$NMe_2$ | $A^2$ | 3-Br | racemate |
| 2-4 | $CFMe_2$ | c-Pr | N=CH—$NMe_2$ | $A^2$ | 4-Na | racemate |
| 2-5 | Me | c-Pr | N=CH—$NMe_2$ | $A^2$ | — | racemate |
| 2-6 | Et | c-Pr | N=CH—$NMe_2$ | $A^2$ | — | racemate |
| 2-7 | $CHMe_2$ | c-Pr | N=C(Me)($NMe_2$) | $A^2$ | — | racemate |
| 2-8 | $CFMe_2$ | c-Pr | N=C(Me)($NMe_2$) | $A^2$ | 4-$CF_3$ | racemate |
| 2-9 | CHFMe | c-Pr | N=C(Me)($NMe_2$) | $A^2$ | 4-$CF_3$ | racemate |
| 2-10 | CHFEt | c-Pr | N=C(Me)($NMe_2$) | $A^2$ | 4-$CF_3$ | racemate |
| 2-11 | $CFMe_2$ | c-Pr | N=CH—$NEt_2$ | $A^2$ | 4-$CF_3$ | racemate |
| 2-12 | CHFEt | c-Pr | N=CH—$NEt_2$ | $A^2$ | 4-$CF_3$ | racemate |
| 2-13 | $CHMe_2$ | c-Pr | N=CH—$NEt_2$ | $A^2$ | 4-$CF_3$ | racemate |

TABLE 2-continued

| No. | R¹ | A²—R² | R³ | A¹ | (X)ₙ | Physical data and stereochemical information |
|---|---|---|---|---|---|---|
| 2-14 | CFMe₂ | c-Pr | N=C(Me)N(CH₂CH₂OH)₂ | A² | 4-CF₃ | racemate |
| 2-15 | CFMe₂ | c-Pr | N=CH—NEt₂ | A² | — | racemate |
| 2-16 | CFMe₂ | c-Pr | N=CH—NEt₂ | A² | 3-Me | racemate |
| 2-17 | CFMe₂ | c-Pr | N=CH—NEt₂ | A² | 3-Cl | racemate |
| 2-18 | CFMe₂ | c-Pr | N=CH—NEt₂ | A² | 3,5-Me₂ | racemate |
| 2-19 | CFMe₂ | c-Pr | N=CH—NEt₂ | A² | 3-F | racemate |
| 2-20 | CHFMe | c-Pr | N=CH—NEt₂ | A² | — | racemate |
| 2-21 | CHFMe | c-Pr | N=CH—NEt₂ | A² | 3-Me | racemate |
| 2-22 | CHFMe | c-Pr | N=CH—NEt₂ | A² | 3-Cl | racemate |
| 2-23 | CHFMe | c-Pr | N=CH—NEt₂ | A² | 3,5-Me₂ | racemate |
| 2-24 | CHFMe | c-Pr | N=CH—NEt₂ | A² | 3-F | racemate |
| 2-25 | CHFEt | c-Pr | N=CH—NEt₂ | A² | — | racemate |
| 2-26 | CHEEt | c-Pr | N=CH—NEt₂ | A² | 3-Me | racemate |
| 2-27 | CHFEt | c-Pr | N=CH—NEt₂ | A² | 3-Cl | racemate |
| 2-28 | CHFEt | c-Pr | N=CH—NEt₂ | A² | 3,5-Me₂ | racemate |
| 2-29 | CHFEt | c-Pr | N=CH—NEt₂ | A² | 3-F | racemate |
| 2-30 | CFMe₂ | c-Pr | N=CH—NMe₂ | A² | — | racemate |
| 2-31 | CFMe₂ | c-Pr | N=CH—NMe₂ | A² | 3-Me | racemate |
| 2-32 | CFMe₂ | c-Pr | N=CH—NMe₂ | A² | 3-Cl | racemate |
| 2-33 | CFMe₂ | c-Pr | N=CH—NMe₂ | A² | 3,5-Me₂ | racemate |
| 2-34 | CFMe₂ | c-Pr | N=CH—NMe₂ | A² | 3-F | racemate |
| 2-35 | CHFMe | c-Pr | N=CH—NMe₂ | A² | — | racemate, oil |
| 2-36 | CHFMe | c-Pr | N=CH—NMe₂ | A² | 3-Me | racemate, oil |
| 2-37 | CHFMe | c-Pr | N=CH—NMe₂ | A² | 3-Cl | racemate |
| 2-38 | CHFMe | c-Pr | N=CH—NMe₂ | A² | 3,5-Me₂ | racemate |
| 2-39 | CHFMe | c-Pr | N=CH—NMe₂ | A² | 3-F | racemate |
| 2-40 | CHFEt | c-Pr | N=CH—NMe₂ | A² | — | racemate |
| 2-41 | CHFEt | c-Pr | N=CH—NMe₂ | A² | 3-Me | racemate |
| 2-42 | CHFEt | c-Pr | N=CH—NMe₂ | A² | 3-Cl | racemate |
| 2-43 | CHFEt | c-Pr | N=CH—NMe₂ | A² | 3,5-Me₂ | racemate |
| 2-44 | CHFEt | c-Pr | N=CH—NMe₂ | A² | 3-F | racemate |
| 2-45 | CFMe₂ | c-Pr | N=C(Me)NMe₂ | A² | — | racemate, oil |
| 2-46 | CFMe₂ | c-Pr | N=C(Me)NMe₂ | A² | 3-Me | racemate |
| 2-47 | CFMe₂ | c-Pr | N=C(Me)NMe₂ | A² | 3-Cl | racemate |
| 2-48 | CFMe₂ | c-Pr | N=C(Me)NMe₂ | A² | 3,5-Me₂ | racemate |
| 2-49 | CFMe₂ | c-Pr | N=C(Me)NMe₂ | A² | 3-F | racemate |
| 2-50 | CHFMe | c-Pr | N=C(Me)NMe₂ | A² | — | racemate |
| 2-51 | CHFMe | c-Pr | N=C(Me)NMe₂ | A² | 3-Me | racemate |
| 2-52 | CHFMe | c-Pr | N=C(Me)NMe₂ | A² | 3-Cl | racemate |
| 2-53 | CHFMe | c-Pr | N=C(Me)NMe₂ | A² | 3,5-Me₂ | racemate |
| 2-54 | CHFMe | c-Pr | N=C(Me)NMe₂ | A² | 3-F | racemate |
| 2-55 | CHFEt | c-Pr | N=C(Me)NMe₂ | A² | — | racemate, oil |
| 2-56 | CHFEt | c-Pr | N=C(Me)NMe₂ | A² | 3-Me | racemate, oil |
| 2-57 | CHEEt | c-Pr | N=C(Me)NMe₂ | A² | 3-Cl | racemate |
| 2-58 | CHFEt | c-Pr | N=C(Me)NMe₂ | A² | 3,5-Me₂ | racemate |
| 2-59 | CHFEt | c-Pr | N=C(Me)NMe₂ | A² | 3-F | racemate |
| 2-60 | CFMe₂ | c-Pr | N=CHNMe₂ | OA1 | — | racemate |
| 2-61 | CHFEr | c-Pr | N=CHNMe₂ | OA1 | — | racemate |
| 2-62 | CClMe₂ | c-Pr | N=C(Me)(NMe₂) | OA1 | — | racemate |
| 2-63 | CHCeMe | c-Pr | N=CHNEt₂ | OA1 | — | racemate |
| 2-64 | Me | c-Pr | N=C(Et)(NEt₂) | OA1 | — | racemate |
| 2-65 | Et | c-Pr | N=C(Pr)(NMe₂) | OA1 | — | racemate |
| 2-66 | CHMe₂ | c-Pr | N=C(Ph)(NEt₂) | OA1 | — | racemate |
| 2-67 | CFMe₂ | c-Pr | N=C(n-Bu)(NMe₂) | OA1 | 3,5-(OMe)₂ | racemate |
| 2-68 | CFMe₂ | c-Pr | NH—N=CHNMe₂ | OA1 | — | racemate |
| 2-69 | CFMe₂ | c-Pr | N=C(Me)(NMe₂) | OA1 | 3,5-Cl₂ | racemate |
| 2-70 | CFMe₂ | c-Pr | N=C(Me)C(NPh₂) | OA1 | 3,5-F₂ | racemate |
| 2-71 | CBrMe₂ | c-Pr | NC(Me)(NEt2) | OA1 | 2,5-F₂ | racemate |
| 2-72 | CClMe₂ | c-Pr | NCHN(n-Pr)₂ | OA1 | — | racemate |
| 2-73 | CHFEt | c-Pr | NH—CH=N—OH | A2 | — | racemate |
| 2-74 | CHFEt₂ | c-Pr | NH—CH=N—OH | A2 | 3-Cl | racemate |
| 2-75 | CHFEt₂ | c-Pr | NH—CH=N—OH | A2 | 3-F | racemate |
| 2-76 | CHFEt₂ | c-Pr | NH—CH=N—OH | A2 | 4-F, 3-Me | racemate |
| 2-77 | CHFEt₂ | c-Pr | NH—CH=N—OH | A2 | 3,4-F₂ | racemate |
| 2-78 | CFMe₂ | c-Pr | N=CH—Ph | A2 | — | racemate |
| 2-79 | CFMe₂ | c-Pr | N=CH—4-Cl-C₆H₄ | A2 | — | racemate |
| 2-80 | CFMe₂ | c-Pr | N=CH-4-F—C₆H₄ | A2 | — | racemate |
| 2-81 | CFMe₂ | c-Pr | N=CH-3,4-F₂—C₆H₃ | A2 | — | racemate |
| 2-82 | CHFMe | c-Pr | N=C(Me)(C₆H₅) | A2 | — | racemate |
| 2-83 | CHFMe | c-Pr | NH—N=CHNMe₂ | A2 | 3,5-Me₂ | racemate |
| 2-84 | CHFMe | c-Pr | NH—N=CHCHNMe₂ | A2 | 3,4-Me₂ | racemate |
| 2-85 | CHFMe | c-Pr | NH—N=CHNMe₂ | A2 | 3-OEt | racemate |
| 2-86 | CHFMe | c-Pr | NH—N=CHNMe₂ | A2 | 3-OCF₃ | racemate |
| 2-87 | CHFMe | c-Pr | NH—N=CHNMe₂ | A2 | 3-OCHF₂ | racemate |

TABLE 2-continued

| No. | R¹ | A²—R² | R³ | A¹ | (X)ₙ | Physical data and stereochemical information |
|---|---|---|---|---|---|---|
| 2-88 | CFMe₂ | c-Pr | 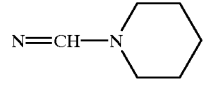 N=CH—N(piperidine) | A2 | — | racemate |
| 2-89 | CFMe₂ | c-Pr | 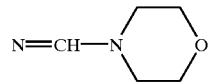 N=CH—N(morpholine) | A2 | — | racemate |
| 2-90 | CFMe₂ | c-Pr | 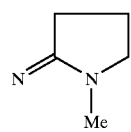 N=C(N-Me pyrrolidine) | A2 | — | racemate |

TABLE 3

| No. | R¹ | A²—R² | R³ | A¹ | (X)ₙ | Physical data and stereochemical information |
|---|---|---|---|---|---|---|
| 3-1 | CFMe₂ | c-Bu | N=CH—NMe₂ | A2 | — | racemate, oil |
| 3-2 | CFMe₂ | c-Bu | N=CH—NMe₂ | A2 | 3-Cl | racemate |
| 3-3 | CHFMe | c-Bu | N=CH—NMe₂ | A2 | 3-OEt | racemate |
| 3-4 | CHFMe | c-Bu | N=CH—NMe₂ | A2 | 3,5-Me₂ | racemate |
| 3-5 | CHMe₂ | c-Bu | N=CH—NMe₂ | A2 | 3-O-i-Pr | racemate |
| 3-6 | CHFMe | c-Bu | N=CH—NMe₂ | A2 | — | racemate |
| 3-7 | CHFEt | c-Bu | N=CH—NMe₂ | A2 | — | racemate |
| 3-8 | Me | c-Bu | N=CH—NMe₂ | A2 | — | racemate |
| 3-9 | Et | c-Bu | N=CH—NMe₂ | A2 | — | racemate |
| 3-10 | CF3 | c-Bu | N=CH—NMe₂ | A2 | — | racemate |
| 3-11 | CClMe₂ | c-Bu | N=NH—NMe₂ | A2 | — | racemate |
| 3-12 | CH₂—O—CH₃ | c-Bu | N=CH—NM₂ | A2 | — | racemate |
| 3-13 | CF₃ | c-Bu | N=C(Me)(NMe₂) | A2 | — | racemate |
| 3-14 | CFMe₂ | c-Bu | N=C(Me)(NMe₂) | A2 | — | racemate, oil |
| 3-15 | CHFMe | c-Bu | N=C(Me)(NMe₂) | A2 | — | racemate |
| 3-16 | CHFEt | c-Bu | N=C(Me)(NMe₂) | A2 | — | racemate |
| 3-17 | Me | c-Bu | N=C(Me)(NMe₂) | A2 | — | racemate |
| 3-18 | c-Pr | c-Bu | N=C(Me)(NMe₂) | A2 | — | racemate |
| 3-19 | CFMe₂ | c-Bu | N=C(Me)(NMe2) | A2 | 3-F | racemate |
| 3-20 | CFMe₂ | c-Bu | N=C(Me)(NMe2) | A2 | 3-CF₃ | racemate |
| 3-21 | CHFMe | c-Bu | N=C(Me)(NMe₂) | A2 | 3-Cl | racemate |
| 3-22 | CFMe₂ | c-Bu | N=C(Me)(NMe₂) | A2 | 3,4-Me₂ | racemate |
| 3-23 | CClMe₂ | c-Bu | N=C(Me)(NMe₂) | A2 | 3-Cl, 5-Me | racemate |
| 3-24 | c-Pr | c-Bu | N=C(Me)(NMe₂) | A2 | 3,5-Me₂ | racemate |
| 3-25 | c-Pr | c-Bu | N=C(Et)(NMe₂) | A2 | — | racemate, oil |
| 3-26 | CFMe₂ | c-Bu | N=CHNEt₂ | A2 | — | racemate |
| 3-27 | CHMe₂ | c-Bu | N=CHNEt₂ | A2 | — | racemate |
| 3-28 | CF₃ | c-Bu | N=CHNEt₂ | A2 | — | racemate |
| 3-29 | CH₂F | c-Bu | N=CHNEt₂ | A2 | — | racemate |
| 3-30 | CFMe₂ | c-Bu | N=CHN(CH₂CH₂OH)₂ | A2 | — | racemate |
| 3-31 | CCH₂Me | c-Bu | N=C(Ph)(NEt₂) | A2 | — | racemate |
| 3-32 | CCH₂Cl | c-Bu | N=C(Ph)(NEt₂) | A2 | — | racemate |
| 3-33 | CCl₃ | c-Bu | N=C(Ph)(NEt₂) | A2 | — | racemate |
| 3-34 | CHCl₂ | c-Bu | N=C(Ph)(N—Pr₂) | A2 | — | racemate |
| 3-35 | CH₂Cl | c-Bu | N=C(3-Cl—Ph)(NMe₂) | A2 | 3,4-Cl₂ | racemate |
| 3-36 | CFMe₂ | c-Bu | N=C(Me)—NMe₂ | A2 | 3-Me | racemate |
| 3-37 | CFMe₂ | c-Bu | N=C(Me)—NMe₂ | A2 | 3,4-F₂ | racemate, oil |
| 3-38 | CFMe₂ | c-Bu | N=C(Me)—NMe₂ | A2 | 3-OMe | racemate, oil |
| 3-39 | CFMe₂ | c-Bu | N=C(Me)—NMe₂ | A2 | 3,4-(OMe)₂ | racemate |
| 3-40 | CFMe₂ | c-Bu | N=C(Me)—NMe₂ | A2 | 3-F | racemate, oil |
| 3-41 | CFMe₂ | c-Bu | N=C(Me)—NMe₂ | A2 | 4-F | racemate, oil |
| 3-42 | CHFMe | c-Bu | N=C(Me)—NMe₂ | A2 | 3-Me | racemate |
| 3-43 | CHFMe | c-Bu | N=C(Me)—NMe₂ | A2 | 3,4-F₂ | racemate, oil |
| 3-44 | CHFMe | c-Bu | N=C(Me)—NMe₂ | A2 | 3-OMe | racemate, oil |
| 3-45 | CHFMe | c-Bu | N=C(Me)—NMe₂ | A2 | 3,4-(OMe)₂ | racemate |
| 3-46 | CHFMe | c-Bu | N=C(Me)—NMe₂ | A2 | 3-F | racemate, oil |
| 3-47 | CHFMe | c-Bu | N=C(Me)—NMe₂ | A2 | 4-F | racemate, oil |
| 3-48 | CHFEt | c-Bu | N=C(Me)—NMe₂ | A2 | 3-Me | racemate |
| 3-49 | CHFEt | c-Bu | N=C(Me)—NMe₂ | A2 | 3,4-F₂ | racemate |

TABLE 3-continued

| No. | R¹ | A²—R² | R³ | A¹ | (X)ₙ | Physical data and stereochemical information |
|---|---|---|---|---|---|---|
| 3-50 | CHFEt | c-Bu | N=C(Me)—NMe₂ | A2 | 3-OMe | racemate |
| 3-51 | CHFEt | c-Bu | N=C(Me)—NMe₂ | A2 | 3,4-(OMe)₂ | racemate |
| 3-52 | CHFEt | c-Bu | N=C(Me)—NMe₂ | A2 | 3-F | racemate |
| 3-53 | CHFEt | c-Bu | N=C(Me)—NMe₂ | A2 | 4-F | racemate |
| 3-54 | CFMe₂ | c-Bu | N=CH—NMe₂ | A2 | 3-Me | racemate |
| 3-55 | CFMe₂ | c-Bu | N=CH—NMe₂ | A2 | 3,4-F₂ | racemate, oil |
| 3-56 | CFMe₂ | c-Bu | N=CH—NMe₂ | A2 | 3-OMe | racemate, oil |
| 3-57 | CFMe₂ | c-Bu | N=CH—NMe₂ | A2 | 3,4-(OMe)₂ | racemate |
| 3-58 | CFMe₂ | c-Bu | N=CH—NMe₂ | A2 | 3-F | racemate, oil |
| 3-59 | CFMe₂ | c-Bu | N=CH—NMe₂ | A2 | 4-F | racemate, oil |
| 3-60 | CHFMe | c-Bu | N=CH—NMe₂ | A2 | 3-Me | racemate |
| 3-61 | CHFMe | c-Bu | N=CH—NMe₂ | A2 | 3,4-F₂ | racemate |
| 3-62 | CHEMe | c-Bu | N=CH—NMe₂ | A2 | 3-OMe | racemate |
| 3-63 | CHFMe | c-Bu | N=CH—NMe₂ | A2 | 3,4-(OMe)₂ | racemate |
| 3-64 | CHFMe | c-Bu | N=CH—NMe₂ | A2 | 3-F | racemate |
| 3-65 | CHFMe | c-Bu | N=CH—NMe₂ | A2 | 4-F | racemate |
| 3-66 | CHFMe | c-Bu | N=CH—NMe₂ | A2 | 3-Me | racemate |
| 3-67 | CHFEt | c-Bu | N=CH—NMe₂ | A2 | 3,4-F₂ | racemate, oil |
| 3-68 | CHFEt | c-Bu | N=CH—NMe₂ | A2 | 3-OMe | racemate, oil |
| 3-69 | CHFEt | c-Bu | N=CH—NMe₂ | A2 | 3,4-(OMe)₂ | racemate |
| 3-70 | CHFEt | c-Bu | N=CH—NMe₂ | A2 | 3-F | racemate, oil |
| 3-71 | CHFEt | c-Bu | N=CH—NMe₂ | A2 | 4-F | racemate, oil |
| 3-72 | CFME₂ | c-Bu | N=CH—NEt₂ | A2 | 3-Me | racemate |
| 3-73 | CFMe₂ | c-Bu | N=CH—NEt₂ | A2 | 3,4-F₂ | racemate |
| 3-74 | CFMe₂ | c-Bu | N=CH—NEt₂ | A2 | 3-OMe | racemate, oil |
| 3-75 | CFMe₂ | c-Bu | N=CH—NEt₂ | A2 | 3,4-(OMe)₂ | racemate |
| 3-76 | CFMe₂ | c-Bu | N=CH—NEt₂ | A2 | 3-F | racemate |
| 3-77 | CFMe₂ | c-Bu | N=CH—NEt₂ | A2 | 4-F | racemate |
| 3-78 | CHEMe | c-Bu | N=CH—NEt₂ | A2 | 3-Me | racemate |
| 3-79 | CHFMe | c-Bu | N=CH—NEt₂ | A2 | 3,4-F₂ | racemate |
| 3-80 | CHFMe | c-Bu | N=CH—NEt₂ | A2 | 3-OMe | racemate |
| 3-81 | CHFMe | c-Bu | N=CH—NEt₂ | A2 | 3,4-(OMe)₂ | racemate |
| 3-82 | CHFMe | c-Bu | N=CH—NEt₂ | A2 | 3-F | racemate |
| 3-83 | CHFMe | c-Bu | N=CH—NEt₂ | A2 | 4-F | racemate |
| 3-84 | CHFEt | c-Bu | N=CH—NEt₂ | A2 | 3-Me | racemate |
| 3-85 | CHFEt | c-Bu | N=CH—NEt₂ | A2 | 3,4-F₂ | racemate, oil |
| 3-86 | CHFEt | c-Bu | N=CH—NEt₂ | A2 | 3-OMe | racemate, oil |
| 3-87 | CHFEt | c-Bu | N=CH—NEt₂ | A2 | 3,4-(OMe)₂ | racemate |
| 3-88 | CHFEt | c-Bu | N=CH—NEt₂ | A2 | 3-F | racemate |
| 3-89 | CHFEt | c-Bu | N=CH—NEt₂ | A2 | 4-F | racemate |
| 3-90 | CHFEt | c-Bu | NH—CH=N—OH | OA1 | — | racemate |
| 3-91 | CHFMe | c-Bu | —NH—CH=N—OH | OA1 | — | racemate |
| 3-92 | CFMe | c-Bu | —NH—CH=N—NH₂ | OA1 | — | racemate |
| 3-93 | CHFEt | c-Bu | —NH—CH=N—NMe₂ | OA1 | — | racemate |
| 3-94 | CFMe₂ | c-Bu | N=CHPh | OA1 | — | racemate |
| 3-95 | CFMe₂ | c-Bu | N=CH-3-Cl—C₆H₃ | OA1 | — | racemate |
| 3-96 | CF₃ | c-Bu | N=CHPh | OA1 | 3,5-Me₂ | racemate |
| 3-97 | CF₃ | c-Bu | N=CHPh | OA1 | 3-F, 4-Me | racemate |
| 3-98 | CF₃ | c-Bu | N=CHPh | OA1 | 3,5-Cl₂ | racemate |
| 3-99 | CF₃ | c-Bu | N=CHPh | OA1 | 3-Cl | racemate |
| 3-100 | CF₃ | c-Bu | N=CHPh | OA1 | 3,4-F₂ | racemate |
| 3-101 | CHF₂ | c-Bu | N=CHPh | OA1 | 2-Cl | racemate |
| 3-102 | CH₂F | c-Bu | N=CH-2,3-Cl₂—C₆H₃ | OA1 | 2,5-Cl₂ | racemate |
| 3-103 | CFMe₂ | c-Bu | N=CH-3,5-Cl₂C₆H₃ | OA1 | 2,6-Cl₂ | racemate |
| 3-104 | CFMe₂ | c-Bu | N=CH—NMe₂ | A2 | — | R enantiomer |
| 3-105 | CFMe₂ | c-Bu | N=CH—NMe₂ | A2 | — | S enantiomer |
| 3-106 | CFMe₂ | c-Bu | N=CH—NMe₂ | OA1 | — | R enantiomer |
| 3-107 | CFMe₂ | c-Bu | N=CH—NMe₂ | OA1 | — | S enantiomer |
| 3-108 | CHMe₂ | c-Bu | NH—CH=N—OH | A2 | 3-F | racemate |
| 3-109 | CHBrMe | c-Bu | NH—CH=N—OH | A2 | 3-CF₃ | racemate |
| 3-110 | CHFMe | c-Bu | NHN=CHNMe₂ | A2 | — | racemate |
| 3-111 | CFMe₂ | c-Bu | NHN=CHNEt₂ | A2 | — | racemate |
| 3-112 | CFMe₂ | c-Bu | NH—NH—CH=NMe | A2 | — | racemate |
| 3-113 | CFMe₂ | c-Bu | NH—CH=N—OH | A2 | — | racemate |
| 3-114 | CFMe₂ | c-Bu | NH—CH=N—OH | A2 | 4-Br | racemate |
| 3-115 | CFMe₂ | c-Bu | NH—CH=N—OH | A2 | 4-NO₂ | racemate |
| 3-116 | CFMe₂ | c-Bu | N=CHPh | A2 | 3-NO₂ | racemate |
| 3-117 | CFMe₂ | c-Bu | N=CH-4-Cl—C₆H₄ | A2 | 2-NO₂ | racemate |
| 3-118 | CFMe₂ | c-Bu | N=CH-3-CH₃—C₆H₄ | A2 | 3-Cl | racemate |
| 3-119 | CFMe₂ | c-Bu | N=CH-3-CF₃—C₆H₄ | A2 | 2,6-Cl₂ | racemate |

TABLE 3-continued

| No. | R¹ | A²—R² | R³ | A¹ | (X)ₙ | Physical data and stereochemical information |
|---|---|---|---|---|---|---|
| 3-120 | CHFMe₂ | c-Bu | N=CH—N(piperidine) | A2 | — | racemate |
| 3-121 | CFMe₂ | c-Bu | N=CH—N(piperidine) | A2 | — | racemate |
| 3-122 | CFMe₂ | c-Bu | N=CH—N(morpholine) | A2 | — | racemate |
| 3-123 | CFMe₂ | c-Bu | N=CH—N(N-Me-piperazine) | A2 | — | racemate |
| 3-124 | CFMe₂ | c-Bu | N=C(N-Me-pyrrolidine) | A2 | — | racemate, oil |
| 3-125 | CFMe₂ | c-Bu | N=C(N-Et-pyrrolidine) | A2 | — | racemate |
| 3-126 | H | c-Bu | N=CH—NEt₂ | A2 | — | racemate |
| 3-127 | CFMe₂ | c-Bu | NHN=CHNMe₂ | A2 | — | racemate |

TABLE 4

| No. | R¹ | A²—R² | R3 | A1 | (X)ₙ | Physical data and stereochemical information |
|---|---|---|---|---|---|---|
| 4-1 | CFMe₂ | c-pentyl | N=CHNMe₂ | A2 | — | racemate |
| 4-2 | CFMe₂ | c-pentyl | N=CHNMe₂ | A2 | 3,4-F₂ | racemate |
| 4-3 | CClMe₂ | c-pentyl | N=CHNMe₂ | A2 | — | racemate |
| 4-4 | CHCl₂ | c-pentyl | N=CHNMe₂ | A2 | — | racemate |
| 4-5 | i-Pr | c-hexyl | N=CHNMe₂ | A2 | — | racemate |
| 4-6 | i-Bu | c-hexyl | N=C(Me)NMe₂ | A2 | — | racemate |
| 4-7 | CFMe₂ | c-pentyl | N=CH—N(thiomorpholine) | A2 | — | racemate |

TABLE 5

| No. | R¹ | A²—R² | R³ | A¹ | (X)ₙ | Physical data and stereochemical information |
|---|---|---|---|---|---|---|
| 5-1 | CFMe₂ | CH₂-c-Pr | N=CH—NEt₂ | A2 | 3-Me | racemate, oil |
| 5-2 | CFMe₂ | CH₂-c-Pr | N=CH—NEt₂ | A2 | 3-OMe | racemate |
| 5-3 | CFMe₂ | CH₂-c-Pr | N=CH—NEt₂ | A2 | 3-Cl | racemate |
| 5-4 | CFMe₂ | CH₂-c-Pr | N=CH—NEt₂ | A2 | — | racemate |
| 5-5 | CHFMe | CH₂-c-Pr | N=CH—NEt₂ | A2 | 3-Me | racemate |
| 5-6 | CHFMe | CH₂-c-Pr | N=CH—NEt₂ | A2 | 3-OMe | racemate |
| 5-7 | CHFMe | CH₂-c-Pr | N=CH—NEt₂ | A2 | 3-Cl | racemate |
| 5-8 | CHFMe | CH₂-c-Pr | N=CH—NEt₂ | A2 | — | racemate |

TABLE 5-continued

| No. | R¹ | A²—R² | R³ | A¹ | (X)ₙ | Physical data and stereochemical information |
|---|---|---|---|---|---|---|
| 5-9 | CHFEt | CH₂-c-Pr | N=CH—NEt₂ | A2 | 3-Me | racemate |
| 5-10 | CHFEt | CH₂-c-Pr | N=CH—NEt₂ | A2 | 3-OMe | racemate |
| 5-11 | CHFEt | CH₂-c-Pr | N=CH—NEt₂ | A2 | 3-Cl | racemate |
| 5-12 | CHFEt | CH₂-c-Pr | N=CH—NEt₂ | A2 | — | racemate |
| 5-13 | CHMe₂ | CH₂-c-Pr | N=CH—NEt₂ | A2 | 3-Me | racemate |
| 5-14 | CHMe₂ | CH₂-c-Pr | N=CH—NEt₂ | A2 | 3-OMe | racemate |
| 5-15 | CHMe₂ | CH₂-c-Pr | N=CH—NEt₂ | A2 | 3-Cl | racemate |
| 5-16 | CHMe₂ | CH₂-c-Pr | N=CH—NEt₂ | A2 | — | racemate |
| 5-17 | CFMe₂ | CH₂-c-Pr | N=C(Me)—NMe₂ | A2 | 3-Me | racemate |
| 5-18 | CFMe₂ | CH₂-c-Pr | N=C(Me)—NMe₂ | A2 | 3-OMe | racemate, oil |
| 5-19 | CFMe₂ | CH₂-c-Pr | N=C(Me)—NMe₂ | A2 | 3-Cl | racemate |
| 5-20 | CFMe₂ | CH₂-c-Pr | N=C(Me)—NMe₂ | A2 | — | racemate |
| 5-21 | CHFMe | CH₂-c-Pr | N=C(Me)—NMe₂ | A2 | 3-Me | racemate |
| 5-22 | CHFMe | CH₂-c-Pr | N=C(Me)—NMe₂ | A2 | 3-OMe | racemate |
| 5-23 | CHFMe | CH₂-c-Pr | N=C(Me)—NMe₂ | A2 | 3-Cl | racemate |
| 5-24 | CHFMe | CH₂-c-Pr | N=C(Me)—NMe₂ | A2 | — | racemate |
| 5-25 | CHFEt | CH₂-c-Pr | N=C(Me)—NMe₂ | A2 | 3-Me | racemate |
| 5-26 | CHFEt | CH₂-c-Pr | N=C(Me)—NMe₂ | A2 | 3-OMe | racemate |
| 5-27 | CHFEt | CH₂-c-Pr | N=C(Me)—NMe₂ | A2 | 3-Cl | racemate |
| 5-28 | CHFEt | CH₂-c-Pr | N=C(Me)—NMe₂ | A2 | — | racemate |
| 5-29 | CFMe₂ | CH₂-c-Pr | N=C(Me)—NMe₂ | A2 | 3-Me | racemate |
| 5-30 | CFMe₂ | CH₂-c-Pr | N=C(Me)—NMe₂ | A2 | 3-OMe | racemate |
| 5-31 | CFMe₂ | CH₂-c-Pr | N=C(Me)—NMe₂ | A2 | 3-Cl | racemate |
| 5-32 | CFMe₂ | CH₂-c-Pr | N=C(Me)—NMe₂ | A2 | — | racemate |
| 5-33 | CFMe₂ | CH₂-c-Pr | N=CH—NMe₂ | A2 | 3-Me | racemate |
| 5-34 | CFMe₂ | CH₂-c-Pr | N=CH—NMe₂ | A2 | 3-OME | racemate |
| 5-35 | CFMe₂ | CH₂-c-Pr | N=CH—NMe₂ | A2 | 3-Cl | racemate |
| 5-36 | CFMe₂ | CH₂-c-Pr | N=CH—NMe₂ | A2 | — | racemate, oil |
| 5-37 | CHFMe | CH₂-c-Pr | N=CH—NMe₂ | A2 | 3-Me | racemate |
| 5-38 | CHFMe | CH₂-c-Pr | N=CH—NMe₂ | A2 | 3-OME | racemate |
| 5-39 | CHFMe | CH₂--Pr | N=CH—NMe₂ | A2 | 3-Cl | racemate |
| 5-40 | CHFMe | CH₂-c-Pr | N=CH—NMe₂ | A2 | — | racemate, oil |
| 5-41 | CHFEt | CH₂-c-Pr | N=CH—NMe₂ | A2 | 3-Me | racemate |
| 5-42 | CHFEt | CH₂-Pr | N=CH—NMe₂ | A2 | 3-OMe | racemate |
| 5-43 | CHFEt | CH₂-c-Pr | N=CH—NMe₂ | A2 | 3-Cl | racemate |
| 5-44 | CHFEt | CH₂-c-Pr | N=CH—NMe₂ | A2 | — | racemate |
| 5-45 | CHMe₂ | CH₂-c-Pr | N=CH—NMe₂ | A2 | 3-Me | racemate |
| 5-46 | CHMe₂ | CH₂-c-Pr | N=CH—NMe₂ | A2 | 3-OMe | racemate |
| 5-47 | CHMe₂ | CH₂-c-Pr | N=CH—NMe₂ | A2 | 3-Cl | racemate |
| 5-48 | CHMe₂ | CH₂-c-Pr | N=CH—NMe₂ | A2 | — | racemate |
| 5-49 | CFMe₂ | CH₂-c-Pr | N=CH—NMe₂ | OA1 | — | racemate |
| 5-50 | CHMe₂ | CH₂-c-Pr | N=CH—NMe₂ | OA1 | — | racemate |
| 5-51 | Ph | CH₂-c-Pr | N=CH—NMe₂ | OA1 | — | racemate |
| 5-52 | c-Bu | CH₂-c-Pr | N=CH—NMe₂ | SA1 | — | racemate |
| 5-53 | c-pentyl | CH₂-c-Pr | N=CH—NMe₂ | SA1 | — | racemate |
| 5-54 | c-Pr | CH₂-c-Pr | N=CH—NMe₂ | SA1 | — | racemate |
| 5-55 | CF₃ | CH₂-c-Pr | N=CH—NMe₂ | SA1 | — | racemate |
| 5-56 | CFMe₂ | CH₂-c-Pr | N=CH—NMe₂ | NMeA1 | — | racemate |
| 5-57 | CHFMe | CH₂-c-Pr | N=CH—NMe₂ | NMe-A1 | — | racemate |
| 5-58 | CFMe₂ | CH₂-c-Pr | N=CH—NMe₂ | NEt-A1 | — | racemate |
| 5-59 | CHFPr | CH₂-c-Pr | N=CH—NMe₂ | NEt-A1 | — | racemate |
| 5-60 | CH₂CH₂CF₃ | CH₂-c-Pr | N=CH—NMe₂ | NPh-A1 | — | racemate |
| 5-61 | CF₂CHF₂ | CH₂-c-Pr | N=CH—NMe₂ | NPh-A1 | — | racemate |
| 5-62 | CFCl₂ | CH₂-c-Pr | N=CH—NMe₂ | NBz-A1 | 2-NO₂ | racemate |
| 5-63 | CFMe₂ | CH₂-c-Pr | N=CHNMe-Ph | A2 | 2-NO₂ | racemate |
| 5-64 | CFMe₂ | CH₂-c-Pr | N=CHNMePh | A2 | — | racemate |
| 5-65 | CFMe₂ | CH₂-c-Pr | N=C(Me)NMe₂ | A2 | — | racemate |
| 5-66 | CFMe₂ | CH₂-c-Pr | N=C(NMe₂)(NMeNMe₂) | A2 | — | racemate |
| 5-67 | CFMe | CH₂-c-Pr | N=C(NEt₂)(NMeNMe₂) | A2 | — | racemate |
| 5-68 | CH₂F | CH₂-c-Pr | N=C(SMe)(NMe₂) | A2 | — | racemate |
| 5-69 | CH₂F | CH₂-c-Pr | N=C(SMe)(NMeOMe) | A2 | — | racemate |
| 5-70 | CH₂F | CH₂-c-Pr | N=C(SMe)(NMeNMe₂) | A2 | — | racemate |
| 5-71 | CH₂CH₂CF₃ | CH₂-c-Pr | N=C(Et)(NHNH₂) | A2 | — | racemate |
| 5-72 | CH₂CH₂CF₃ | CH₂-c-Pr | NH—N=CH—NMeOMe | A2 | — | racemate |
| 5-73 | CH₂CH₂CF₃ | CH₂-c-Pr | NH—N=CHNMeSMe | A2 | — | racemate |
| 5-74 | H | CH₂-c-Pr | N=CH—NMe₂ | A2 | — | racemate |

TABLE 6

| No. | R¹ | A²—R² | R³ | A¹ | (X)$_n$ | Physical data and stereochemical information |
|---|---|---|---|---|---|---|
| 6-1 | CHFMe | 3-furyl | N=CHNMe$_2$ | A2 | — | racemate |
| 6-2 | CHFMe | 3-furyl | N=C(Me)(NMe$_2$) | A2 | — | racemate |
| 6-3 | CHFMe | 3-furyl | N=C(Et)(NMe$_2$) | A2 | — | racemate |

TABLE 6-continued

| No. | R¹ | A²—R² | R³ | A¹ | (X)$_n$ | Physical data and stereochemical information |
|---|---|---|---|---|---|---|
| 6-4 | CHFMe | 3-furyl | N=CHNEt$_2$ | A2 | — | racemate |
| 6-5 | CFMe$_2$ | 3-furyl | N=CMeNMe$_2$ | A2 | — | racemate |
| 6-6 | CFMe$_2$ | 3-furyl | N=CHNMe$_2$ | A2 | — | racemate |

TABLE 7

| No. | R¹ | A²—R² | R³ | A¹ | (X)$_n$ | Physical data and stereochemical information |
|---|---|---|---|---|---|---|
| 7-1 | CFMe$_2$ | 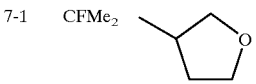 | N=CHNMe$_2$ | A2 | — | racemate |
| 7-2 | CFMe$_2$ | 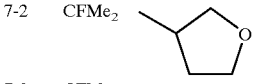 | N=CHNMe$_2$ | A2 | 3-Me | racemate |
| 7-3 | CFMe$_2$ | 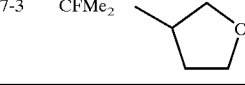 | N=CHNMe$_2$ | A2 | 3,5-Me$_2$ | racemate |

TABLE 8

| No. | R¹ | A²—R² | R³ | A¹ | (X)$_n$ | Physical data and stereochemical information |
|---|---|---|---|---|---|---|
| 8-1 | c-Pr | c-Pr | N=CHNMe$_2$ | A3 | — | racemate |
| 8-2 | CFMe$_2$ | c-Pr | N=CHNMe$_2$ | A3 | — | racemate, oil |
| 8-3 | CF$_3$ | c-Pr | N=CHNMe$_2$ | A3 | 3,5-Cl$_2$ | racemate |
| 8-4 | CF$_2$CF$_3$ | c-Pr | N=CHNMe$_2$ | A3 | — | racemate |
| 8-5 | CFMe$_2$ | c-Pr | N=CHNMe$_2$ | A3 | 3-CF$_3$ | racemate |
| 8-6 | CFMe$_2$ | c-Pr | N=CHNMe$_2$ | A3 | 2-F | racemate |
| 8-7 | CFMe$_2$ | c-Pr | N=CHNMe$_2$ | A3 | 4-F | racemate |
| 8-8 | CFMe$_2$ | c-Pr | N=CHNMe$_2$ | A3 | 4-OCF$_3$ | racemate |
| 8-9 | CFMe$_2$ | c-Pr | N=CHNMe$_2$ | A3 | 4-Cl | racemate |
| 8-10 | CH$_2$F | c-Pr | N=CHNEt$_2$ | A3 | — | racemate |
| 8-11 | CFMe$_2$ | c-Pr | N=CHNEt$_2$ | A3 | — | racemate, oil |
| 8-12 | CFMe$_2$ | c-Pr | N=CHNEt$_2$ | A3 | 4-F, 3-Me | racemate |
| 8-13 | CFMe$_2$ | c-Pr | N=CHNEt$_2$ | A3 | 3-Et | racemate |
| 8-14 | CHFMe | c-Pr | N=CHNEt$_2$ | A3 | — | racemate |
| 8-15 | CHFEt | c-Pr | N=CHNEt$_2$ | A3 | — | racemate |
| 8-16 | CHFPr | c-Pr | N=CHNEt$_2$ | A3 | — | racemate |
| 8-17 | CFMe$_2$ | c-Pr | N=CH—NMe$_2$ | A3 | 3-Cl | racemate |
| 8-18 | CHFMe | c-Pr | N=CH—NMe$_2$ | A3 | 3-Cl | racemate |
| 8-19 | CHFEt | c-Pr | N=CH—NMe$_2$ | A3 | 3-Cl | racemate |
| 8-20 | CFMe$_2$ | c-Pr | N=C(Me)(NMe$_2$) | A3 | 3-F | racemate, oil |
| 8-21 | CHFMe | c-Pr | N=C(Me)(NMe$_2$) | A3 | 3-F | racemate, oil |
| 8-22 | CHFEt | c-Pr | N=C(Me)(NMe$_2$) | A3 | 3-F | racemate |
| 8-23 | CHMe$_2$ | c-Pr | N=CH—NEt$_2$ | A3 | 3-OMe | racemate |
| 8-24 | CFMe$_2$ | c-Pr | N=CH—NEt$_2$ | A3 | 3-OMe | racemate |
| 8-25 | CHFMe | c-Pr | N=CH—NEt$_2$ | A3 | 3-OMe | racemate |
| 8-26 | CHFEt | c-Pr | N=CH—NEt$_2$ | A3 | 3-OMe | racemate |
| 8-27 | CFMe$_2$ | c-Pr | NH—CH=N—OH | A3 | — | racemate |
| 8-28 | CFMe$_2$ | c-Pr | NH—CH=N—NH$_2$ | A3 | — | racemate, oil |
| 8-29 | CFMe$_2$ | c-Pr | NH—CH=N—NMe$_2$ | A3 | — | racemate |
| 8-30 | CFMe$_2$ | c-Pr | N=CH(Me)(Ph) | A3 | — | racemate |
| 8-31 | CFMe$_2$ | c-Pr | N=CH(Ph)$_2$ | A3 | — | racemate |
| 8-32 | CFMe$_2$ | c-Pr | N=CH(2-Cl—C$_6$H$_4$)$_2$ | A3 | — | racemate |
| 8-33 | CFMe$_2$ | c-Pr | N=CH(Me)(4-NO$_2$—C$_6$H$_4$) | A3 | — | racemate |
| 8-34 | CFMe$_2$ | c-Pr | N=CH(Et)(Ph) | A3 | — | racemate |
| 8-35 | CFMe$_2$ | c-Pr | N=CH(n-Pr)(Ph) | A3 | — | racemate |

TABLE 8-continued

| No. | R¹ | A²—R² | R³ | A¹ | (X)ₙ | Physical data and stereochemical information |
|---|---|---|---|---|---|---|
| 8-36 | CHFMe | c-Pr | N=CH(3-Cl—C₆H₄) | A3 | — | racemate |
| 8-37 | CFMe₂ | c-Pr | N=CH(4-Cl—C₆H₄) | A3 | — | racemate, oil |
| 8-38 | CFMe₂ | c-Pr | N=CH—NMe₂ | OA2 | — | racemate |
| 8-39 | CMe=CH₂ | c-Pr | N=CH—NMe₂ | OA2 | — | racemate |
| 8-40 | CF₃ | c-Pr | N=CH—NMe₂ | OA2 | — | racemate |
| 8-41 | CHF₂ | c-Pr | N=CH—NMe₂ | OA2 | — | racemate |
| 8-42 | CHF₂ | c-Pr | N=CH—NMe₂ | OA2 | — | racemate |
| 8-43 | CF₃ | c-Pr | N=CH—NMe₂ | OA2 | 3,5-Me₂ | racemate |
| 8-44 | CCl₃ | c-Pr | N=CH—NMe₂ | OA2 | 3-Et | racemate |
| 8-45 | CFCe₂ | c-Pr | N=CH—NMe₂ | OA2 | — | racemate |
| 8-46 | Me | c-Pr | N=C(NMe₂)₂ | OA2 | — | racemate |
| 8-47 | Me | c-Pr | N=C(NEt₂)₂ | OA2 | — | racemate |
| 8-48 | i-Pr | c-Pr | N=C(NMe₂)(NEt₂) | OA2 | — | racemate |
| 8-49 | i-Bu | c-Pr | N=C(NMe₂)(NMeOMe) | OA2 | — | racemate |
| 8-50 | sec-Bu | c-Pr | N=C(NEt₂)(NEtOEt) | OA2 | — | racemate |
| 8-51 | n-Bu | c-Pr | N=C(NMe₂)(NMeSMe) | OA2 | — | racemate |
| 8-52 | CF₂CHF₂ | c-Pr | N=C(OMe)(NMeOMe) | OA2 | — | racemate |
| 8-53 | CFMe₂ | c-Pr | N=CH—NMe₂ | A3 | — | R enantiomer |
| 8-54 | CFMe₂ | c-Pr | N=CH—NMe₂ | A3 | — | S enantiomer |
| 8-55 | CFMe₂ | c-Pr | N=CHNEt₂ | A3 | — | R enantiomer |
| 8-56 | CFMe₂ | c-Pr | N=CHNEt₂ | A3 | — | S enantiomer |
| 8-57 | CFMe₂ | c-Pr | N=CHNMe₂ | A3 | 3-F | racemate, oil |
| 8-58 | CHFMe | c-Pr | N=CHNMe₂ | A3 | 3-F | racemate, oil |
| 8-59 | CFMe₂ | c-Pr | N=CHNEt₂ | A3 | 3-F | racemate, oil |

TABLE 9

| No. | R¹ | A²—R² | R³ | A¹ | (X)ₙ | Physical data and stereochemical information |
|---|---|---|---|---|---|---|
| 9-1 | CFMe₂ | c-Bu | N=CH—NMe₂ | A3 | — | racemate |
| 9-2 | CHMe₂ | c-Bu | N=CH—NMe₂ | A3 | — | racemate |
| 9-3 | CHFMe | c-Bu | N=CH—NMe₂ | A3 | — | racemate |
| 9-4 | CHFMe | c-Bu | N=CH—NMe₂ | OA2 | — | racemate |
| 9-5 | CF₃ | c-Bu | N=C(Me)(NPr₂) | OA2 | — | racemate |

TABLE 10

| No. | R¹ | A²—R² | R³ | A¹ | (X)ₙ | Physical data and stereochemical information |
|---|---|---|---|---|---|---|
| 10-1 | CH₂OEt | c-Pr | N=C(Ph)(NMe₂) | A4 | — | racemate |
| 10-2 | 4-Cl—C₆H₄ | c-Pr | N=C(Bu)(NMe₂) | A4 | — | racemate |
| 10-3 | c-Pr | c-Pr | N=C(Me)(NEt₂) | A4 | — | racemate |
| 10-4 | c-Bu | c-Pr | N=CHN(CH₂Ph)₂ | A4 | — | racemate |
| 10-5 | CFMe₂ | c-Pr | N=CHNMe₂ | A4 | — | racemate |
| 10-6 | CFMe₂ | c-Pr | N=CHNMe₂ | OA3 | — | racemate |

TABLE 11

| No. | R¹ | A²—R² | R³ | A¹ | (X)ₙ | Physical data and stereochemical information |
|---|---|---|---|---|---|---|
| 11-1 | Me | Ph | N=CH—NEt₂ | A2 | — | racemate |
| 11-2 | Me | Ph | N=CH—NEt₂ | A2 | 3,5—Cl₂ | racemate |
| 11-3 | Me | 4-CF₃—C₆H₄ | N=CH—NMe₂ | OA1 | — | racemate |
| 11-4 | CFMeEt | CH₂Ph | N=CH—NMe₂ | OA1 | — | racemate |
| 11-5 | CFMeEt | 4-CN—C₆H₄ | N=CH—NMe₂ | OA2 | — | racemate |

TABLE 12

Compounds of the formula

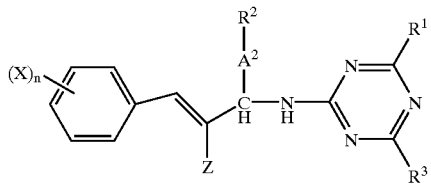

| No. | $R^1$ | $A^2$—$R^2$ | $R^3$ | Z | $(X)_n$ | Physical data and stereochemical information |
|---|---|---|---|---|---|---|
| 12-1 | CFMe$_2$ | c-Pr | N=CH—NMe$_2$ | H | — | racemate |
| 12-2 | CHFMe | c-Pr | N=CH—NMe$_2$ | H | — | racemate |
| 12-3 | CFMe$_2$ | c-Pr | N=CH—NMe$_2$ | H | 3-Cl | racemate |
| 12-4 | CFMe$_2$ | c-Pr | N=CH—NMe$_2$ | H | 3-F | racemate |
| 12-5 | CFMe$_2$ | c-Pr | N=CH—NMe$_2$ | H | 3-CH$_3$ | racemate |
| 12-6 | CFMe$_2$ | c-Pr | N=CH—NMe$_2$ | H | 3-OCH$_3$ | racemate |
| 12-7 | CHFMe | c-Pr | N=CH—NMe$_2$ | H | 3-Cl | racemate |
| 12-8 | CHFMe | c-Pr | N=CH—NMe$_2$ | H | 3-F | racemate |
| 12-9 | CHFMe | c-Pr | N=CH—NMe$_2$ | H | 3-CH$_3$ | racemate |
| 12-10 | CHFMe | c-Pr | N=CH—NMe$_2$ | H | 3-OCH$_3$ | racemate |
| 12-11 | CFMe$_2$ | c-Pr | N=CH—NMe$_2$ | F | H | racemate |
| 12-12 | CFMe$_2$ | c-Pr | N=CH—NMe$_2$ | F | 3-Cl | racemate |
| 12-13 | CFMe$_2$ | c-Pr | N=CH—NMe$_2$ | F | 3-F | racemate |
| 12-14 | CFMe$_2$ | c-Pr | N=CH—NMe$_2$ | F | 3-Me | racemate |
| 12-15 | CFMe$_2$ | c-Pr | N=CH—NMe$_2$ | F | 3-OMe | racemate |
| 12-16 | CHFMe | c-Pr | N=CH—NMe$_2$ | F | — | racemate |
| 12-17 | CHFMe | c-Pr | N=CH—NMe$_2$ | F | — | racemate |
| 12-18 | CHFMe | c-Pr | N=CH—NMe$_2$ | F | — | racemate |
| 12-19 | CHFMe | c-Pr | N=CH—NMe$_2$ | F | — | racemate |
| 12-20 | CFMe$_2$ | c-Pr | N=CHNEt$_2$ | H | — | racemate |
| 12-21 | CFMe$_2$ | c-Pr | N=C(Me)NEt$_2$ | H | — | racemate |
| 12-22 | CFMe$_2$ | c-Pr | N=C(Me)NPr$_2$ | H | — | racemate |
| 12-23 | CHFMe | c-Pr | N=CH—NEt$_2$ | H | — | racemate |
| 12-24 | CHFEt | c-Pr | N=CH—NEt$_2$ | H | — | racemate |
| 12-25 | CHFEt | c-Pr | N=CH—NEt$_2$ | Me | — | racemate |
| 12-26 | CHFMe | c-Pr | N=CH—NEt$_2$ | Me | — | racemate |
| 12-27 | CFMe | c-Pr | N=CH—NEt$_2$ | Me | — | racemate |
| 12-28 | CHF$_2$ | c-Pr | N=CH—NEt$_2$ | Et | 3,5-(OEt)$_2$ | racemate |
| 12-29 | CFMe$_2$ | c-Bu | N=CH—NMe$_2$ | H | — | racemate |
| 12-30 | CHFMe | c-Bu | N=CH—NMe$_2$ | H | — | racemate |
| 12-31 | CHFEt | c-Bu | N=CH—NMe$_2$ | H | — | racemate |
| 12-32 | CHFPr | c-Bu | N=CH—NMe$_2$ | H | — | racemate |
| 12-33 | CFMe$_2$ | c-Bu | N=CH—NMe$_2$ | H | — | racemate |
| 12-34 | CFMe$_2$ | c-Bu | N=CH—NMe$_2$ | F | — | racemate |
| 12-35 | CFMe$_2$ | c-Bu | N=CH—NMe$_2$ | Cl | — | racemate |
| 12-36 | CFMe$_2$ | c-Bu | N=CH—NMe$_2$ | Br | — | racemate |
| 12-37 | CFMe$_2$ | c-Bu | N=CH—NMe$_2$ | Me | — | racemate |
| 12-38 | CFMe$_2$ | c-Bu | N=CH—NMe$_2$ | Et | — | racemate |
| 12-39 | CHFMe | c-Bu | N=CH—NMe$_2$ | H | — | racemate |
| 12-40 | CHFMe | c-Bu | N=CH—NMe$_2$ | F | — | racemate |
| 12-41 | CHMe | c-Bu | N=CH—NMe$_2$ | Me | — | racemate |
| 12-42 | CFMe$_2$ | c-Bu | N=CH—Net$_2$ | H | — | racemate |
| 12-43 | CHFEt | c-Bu | N=CH—Net$_2$ | F | — | racemate |
| 12-44 | CF$_3$ | c-Bu | N=CH—Net$_2$ | Me | — | racemate |
| 12-45 | CF$_3$ | c-Bu | N=C(Me)(NMe$_2$) | H | — | racemate |
| 12-46 | CF$_2$Me | c-Bu | N=C(Me)(NMe$_2$) | H | — | racemate |
| 12-47 | CFMe$_2$ | c-Bu | N=C(Me)(NMe$_2$) | H | — | racemate |
| 12-48 | CFMe$_2$ | c-Bu | N=C(Me)(NMe$_2$) | | 4-F, 3-Me | racemate |
| 12-49 | CFMe$_2$ | c-Bu | N=C(Et)(NEt$_2$) | | 4-F, 3-Me | racemate |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert material, 10 parts by weight of potassium lignosulfonate and 1 part by weight of sodium oleoylm-ethyltaurate as wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether ®Triton X 207), 3 parts by weight of isotridecanol polyglycol ether (8 EO) and 71 parts by weight of paraffinic mineral oil (boiling range for example approx. 255 to over 277° C.) and grinding the mixture in a grinding-ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.
e) Water-dispersible granules are obtained by mixing > 75 parts by weight of a compound of the formula (I),
> 10 parts by weight of calcium lignosulfonate,
> 5 parts by weight of sodium laurylsulfate,
> 3 parts by weight of polyvinyl alcohol and
> 7 parts by weight of kaolin, grinding the mixture on a pinned-disk mill and granulating the powder in a fluidized bed by spraying on water of granulation liquid.
f) Water-dispersible granules are also obtained by homogenizing and precomminuting > 25 parts by weight of a compound of the formula (I),
> 5 parts by weight 2,2'-dinaphthylmethane-6,6'-disulfonate,
> 2 parts by weight sodium oleoylmethyltaurate,
> 1 part by weight of polyvinyl alcohol,
> 17 parts by weight of calcium carbonate and
> 50 parts by weight of water in a colloid mill, subsequently grinding the mixture in a bead mill and atomizing and drying the resulting suspension in a spray tower by means of a single-substance nozzle.

C. Biological Examples

1. Pre-Emergence Herbicidal Action

Seeds or rhizome pieces of monocotyledonous and dicotyledonous weed plants are placed in sandy loam in plastic pots and covered with soil. The compounds according to the invention, which are formulated in the form of wettable powders or emulsion concentrates, are then applied to the surface of the soil cover as aqueous suspension or emulsion at various dosages with an application rate of 600 to 800 l of water per ha (converted).

After the treatment, the pots are placed into a greenhouse and kept under good growth conditions for the weeds. The plant or emergence damage is scored visually after the test plants have emerged after an experimental time of 3 to 4 weeks by comparison with untreated controls.

The compounds according to the invention show a very good pre-emergence activity against a broad spectrum of grass weeds and broad-leaved weeds. For example, compounds according to the invention (see Examples A1 to A3 and compounds 2-1, 2-35, 2-36, 2-45, 2-55, 2-56, 3-1,3-14, 3-25, 3-37, 3-38, 3-40, 3-41, 3-43, 3-44, 3-46, 3-47, 3-55, 3-56, 3-58, 3-59, 3-67, 3-68, 3-70, 3-71, 3-74, 3-85, 3-86, 3-124, 5-1, 5-40, 8-2, 8-11, 8-20, 8-21, 8-27 and 8-37 of Tables 1 to 12) effect a very good pre-emergence control on harmful plants such as *Stellaria media, Lolium multiforum, Amaranthus retroflexus, Sinapis alba, Avena sativa* and *Setaria viridis*.

2. Post-Emergence Herbicidal Action

Seeds or rhizome pieces of monocotyledonous and dicotyledonous weeds are placed in sandy loam in plastic pots, covered with soil and grown in the greenhouse under good growth conditions. Three weeks after sowing, the test plants are treated in the three-leaf stage. Various dosages of the compounds according to the invention, which are formulated as wettable powders or emulsion concentrates, are sprayed to the green plant parts at an application rate of 600 to 800 l of water per ha (converted). After the test plants have been left to stand in the greenhouse for approx. 3 to 4 weeks under optimal growth conditions, the effect of the preparations is scored visually by comparison with untreated controls. The compositions according to the invention also have a good herbicidal post-emergence activity against a broad spectrum of economically important grass weeds and broad-leaved weeds, for example against harmful plants such as *Sinapis alba, Echinochloa crus-galli, Lolium multiflorum, Stellaria media, Cyperus iria, Amaranthus retroflexus, Setaria viridis* and *Avena sativa* when an application rate of 1 kg and less active substance of the compounds according to the invention (see Examples A1 to A3 and compounds 2-1, 2-35, 2-36, 2-45, 2-55, 2-56, 3-1, 3-14, 3-25, 3-37, 3-38, 3-40, 3-41, 3-43, 3-44, 3-46, 3-47, 3-55, 3-56, 3-58, 3-59, 3-67, 3-68, 3-70, 3-71, 3-74, 3-85, 3-86, 3-124, 5-1, 5-40, 8-2, 8-11, 8-20, 8-21, 8-27 and 8-37 of Tables 1 to 12) is applied post-emergence per hectare.

3. Action Against Harmful Plants in Rice

Transplanted and seeded rice and typical rice weeds (broad-leaved and grass weeds) are grown in the greenhouse until they have reached the three-leaf stage (*Echinochloa crus-galli* 1.5-leaves) under paddy rice conditions (flooding level of the water: 2–3 cm) in closed plastic pots. They are then treated with the compounds according to the invention. To this end, the formulated active substances are suspended, dissolved or emulsified in water and applied to the paddy water of the test plants at various dosages by application by pouring. After the treatment has been carried out in this way, the test plants are placed into the greenhouse under optimal growth conditions and kept in this way over the entire experimental period.

Approximately three weeks after application, the experiments are evaluated by visually scoring the plant damage in comparison with untreated controls. The compounds according to the invention (see Examples A1 to A3 and compounds 2-1, 2-35, 2-36, 2-45, 2-55, 2-56, 3-1, 3-14, 3-25, 3-37, 3-38, 3-40, 3-41, 3-43, 3-44, 3-46, 3-47, 3-55, 3-56, 3-58, 3-59, 3-67, 3-68, 3-70, 3-71, 3-74, 3-85, 3-86, 3-124, 5-1, 5-40, 8-2, 8-11, 8-20, 8-21, 8-27 and 8-37 of Tables 1 to 12) show a very good herbicidal action against harmful plants such as, for example, *Cyperus monti, Echinochloa crus-galli* and *Sagittaria pygmaea*.

4. Crop Plant Tolerance

In further greenhouse experiments seeds of a larger number of crop plants and weeds are placed in sandy loam covered with soil. Some of the pots are coated immediately as described in Section 1, while the remaining pots are placed in the greenhouse until the plants have developed two to three leaves and are then sprayed with various dosages of the substances of formula (I) according to the invention as described under Section 2. Four to five weeks after the application and standing time in the greenhouse, it is found by means of visual scoring that the compounds according to the invention leave dicotyledonous crops such as, for example, soybeans, cotton, oilseed rape, sugar beet and potatoes unharmed when applied pre- and post-emergence, even at high rates of active substance. In addition, some substances also leave graminaceous crops such as, for example, barley, wheat, rye, sorghum, maize or rice, unharmed. Some of the compounds of the formula (I) show a high degree of selectivity and are therefore suitable for controlling undesired vegetation in agricultural crops.

What is claimed is:
1. A compound of the formula (I) or a salt thereof

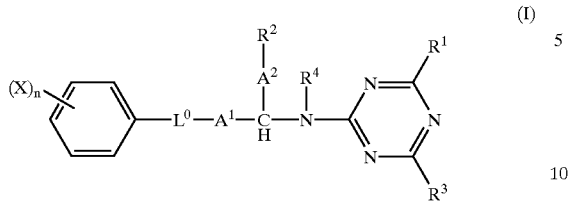

in which
R$^1$ is aryl, aryloxy, arylthio, arylamino, N-aryl-N-(C$_1$–C$_4$)alkylamino, (C$_3$–C$_9$)cycloalkyl, (C$_3$–C$_9$)cycloalkyloxy, (C$_3$–C$_9$)cycloalkylthio, (C$_3$–C$_9$)cycloalkylamino, N-(C$_3$–C$_9$)cycloalkyl-N-(C$_1$–C$_4$)alkylamino, di-[(C$_3$–C$_9$)cycloalkyl]amino, heterocyclyl, heterocyclyloxy, heterocyclylthio, heterocyclylamino or N-heterocyclyl-N-(C$_1$–C$_4$)alkylamino, where each of the last-mentioned 16 radicals is unsubstituted or substituted, or is hydrogen, (C$_1$–C$_6$)alkyl, (C$_2$–C$_6$)alkenyl, (C$_2$–C$_6$)alkynyl, (C$_1$–C$_6$)alkoxy, (C$_2$–C$_6$)alkenyloxy, (C$_2$–C$_6$)alkynyloxy, (C$_1$–C$_6$)alkylthio, (C$_2$–C$_6$)alkenylthio, (C$_2$–C$_6$)alkynylthio, (C$_1$–C$_6$)alkylamino or di-[(C$_1$–C$_6$)alkyl]amino,
where each of the last-mentioned 11 radicals can be unsubstituted or substituted by one or more radicals selected from the group consisting of halogen, hydroxyl, cyano, nitro, thiocyanato, (C$_1$–C$_4$)alkoxy, (C$_1$–C$_4$)haloalkoxy, (C$_2$–C$_4$)alkenyloxy, (C$_2$–C$_4$)haloalkenyloxy, (C$_1$–C$_4$)alkylthio, (C$_1$–C$_4$)alkylsulfinyl, (C$_1$–C$_4$)alkylsulfonyl, (C$_1$–C$_4$)haloalkylthio, (C$_1$–C$_4$)haloalkylsulfinyl, (C$_1$–C$_4$)haloalkylsulfonyl, (C$_3$–C$_9$)cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—,
where R', R" and R'" in each case independently of one another are hydrogen (C$_1$–C$_6$)alkyl, aryl, aryl-(C$_1$–C$_6$)alkyl, (C$_3$–C$_9$)cycloalkyl or (C$_3$–C$_9$)cycloalkyl-(C$_1$–C$_6$)alkyl, where each of the 5 last-mentioned radicals is unsubstituted or substituted, and where Z and Z' independently of one another are in each case an oxygen or sulfur atom,
R$^2$ is (C$_3$–C$_9$)cycloalkyl which is unsubstituted or substituted, (C$_4$–C$_9$)cycloalkenyl which is unsubstituted or substituted, heterocyclyl which is unsubstituted or substituted, or phenyl which is unsubstituted or substituted,
R$^3$ is a group

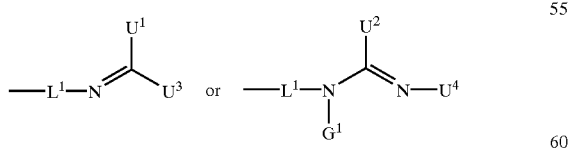

in which
L$^1$ is a direct bond, —O—, —S— or a group of the formula —NG$^2$—,
U$^1$, U$^2$ independently of one another are a group of the formula G$^3$, OG$^4$, SG$^5$, NG$^6$G$^7$, NG$^8$NG$^9$G$^{10}$, NG$^{11}$OG$^{12}$ or NG$^{11}$SG$^{12}$, U$^3$ is a group of the formula G$^{13}$, OG$^{14}$, SG$^{15}$, NG$^{16}$G$^{17}$, NG$^{18}$NG$^{19}$G$^{20}$, NG$^{21}$OG$^{22}$ or NG$^{23}$SG$^{24}$,
U$^4$ is a group of the formula G$^{25}$, OG$^{26}$, SG$^{27}$ or NG$^{28}$G$^{29}$,
where the radicals G$^1$ to G$^{29}$ independently of one another are aryl which is unsubstituted or substituted or (C$_3$–C$_9$)cycloalkyl which is unsubstituted or substituted, or heterocyclyl which is substituted or unsubstituted, or are (C$_1$–C$_6$)alkyl, (C$_2$–C$_6$)alkenyl or (C$_2$–C$_6$)alkynyl,
where each of the last-mentioned 3 radicals is unsubstituted or substituted by one or more radicals selected from the group consisting of halogen, hydroxyl, cyano, nitro, thiocyanato, (C$_1$–C$_4$)alkoxy, (C$_1$–C$_4$)haloalkoxy, (C$_2$–C$_4$)alkenyloxy, (C$_2$–C$_4$)haloalkenyloxy, (C$_1$–C$_4$)alkylthio, (C$_1$–C$_4$)alkylsulfinyl, (C$_1$–C$_4$)alkylsulfonyl, (C$_1$–C$_4$)haloalkylsulfonyl, (C$_3$–C$_9$)cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—,
where R', R" and R'" in each case independently of one another are hydrogen, (C$_1$–C$_6$)alkyl, aryl, aryl-(C$_1$–C$_6$)alkyl, (C$_3$–C$_9$)cycloalkyl or (C$_3$–C$_9$)cycloalkyl-(C$_1$–C$_6$)alkyl, where each of the 5 last-mentioned radicals is unsubstituted or substituted and where Z and Z' independently of one another are in each case an oxygen or sulfur atom, and, inclusive of substituents, has 1 to 30 carbon atoms, or G$^1$, G$^2$, G$^3$, G$^6$, G$^7$, G$^8$, G$^9$, G$^{10}$, G$^{11}$, G$^{12}$, G$^{13}$, G$^{16}$, G$^{17}$, G$^{18}$, G$^{19}$, G$^{20}$, G$^{21}$, G$^{22}$, G$^{23}$, G$^{24}$, G$^{25}$, G$^{26}$, G$^{27}$, G$^{28}$ and G$^{29}$ independently of one another are hydrogen, or the radicals U$^1$ and U$^3$ or U$^2$ and U$^4$ or U$^2$ and G$^1$ or U$^4$ and G$^1$, as a pair, together with the atoms linking them are in each case a carbocyclic or heterocyclic ring having 4 to 7 ring atoms, the ring being unsubstituted or substituted,
R$^4$ is a radical of the formula —B$^1$—D$^4$, where B$^1$ and D$^1$ are as defined hereinbelow,
A$^1$ is a direct bond or straight-chain alkylene having 1 to 5 carbon atoms or straight-chain alkenylene or alkynylene having in each case 2 to 5 carbon atoms, where each of the three last-mentioned diradicals is unsubstituted or substituted by one or more radicals selected from the group consisting of halogen, nitro, cyano, thiocyanato and radicals of the formula —B$^2$—D$^2$, where B$^2$ and D$^2$ are as defined hereinbelow,
A$^2$ is a direct bond or straight-chain alkylene having 1 to 4 carbon atoms or straight-chain alkenylene or alkynylene having in each case 2 to 5 carbon atoms, where each of the three last-mentioned diradicals is unsubstituted or substituted by one or more radicals selected from the group consisting of halogen, nitro, cyano, thiocyanato and radicals of the formula —B$^3$D$^3$, or a divalent radical of the formula V$^1$, V$^2$, V$^3$, V$^4$ or V$^5$, —CR$^a$R$^b$—W*—CR$^c$R$^d$— (V$^1$)

—CR$^a$R$^b$—W*—CR$^c$R$^d$—CR$^e$R$^f$— (V$^2$)

—CR$^a$R$^b$—CR$^c$R$^d$—W*—CR$^e$R$^f$— (V$^3$)

—CR$^a$R$^b$—CR$^c$R$^d$—W*— (V$^4$)

—CR$^a$R$^b$—W*— (V$^5$)

where each of the radicals R$^a$, R$^b$, R$^c$, R$^d$, R$^e$ and R$^f$ in each case independently of one another is hydrogen, halogen, nitro, cyano, thiocyanato or a radical of the formula —B$^4$—D$^4$, W* is in each case an oxygen atom, a sulfur atom or a group of the formula N(B$^5$—D$^5$) and B$^3$, B$^4$, B$^5$, D$^3$, D$^4$ and D$^5$ are as defined hereinbelow, B$^1$ and B$^5$ in each case independently of one another are a direct bond or a divalent group of the formulae —C(=Z*)—, —C(=Z*)—Z**—, —C(=Z*)—NH— or —C(=Z*)—NR*—, where Z*=an oxygen or sulfur atom, Z**=an oxygen or sulfur atom and R* —(C$_1$–C$_6$)alkyl, aryl, aryl-(C$_1$–C$_6$)alkyl, (C$_3$–C$_9$)cycloalkyl or (C$_3$–C$_9$)cycloalkyl-(C$_1$–C$_6$)alkyl, where each of the 5 last-mentioned radicals is unsubstituted or substituted, B$^2$, B$^3$ and B$^4$ in each case independently of one another are a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —NR$^O$—, —O—NR$^O$—, —NR$^O$—O—, —NR$^O$—CO—, —CO—NR$^O$—, —O—CO—NR$^O$— or —NR$^O$—CO—O—, where p is the integer 0, 1 or 2 and R$^O$ is hydrogen, (C$_1$–C$_6$)alkyl, aryl, aryl-(C$_1$–C$_6$)alkyl, (C$_3$–C$_9$)cycloalkyl or (C$_3$–C$_9$)cycloalkyl-(C$_1$–C$_6$)alkyl, where each of the 5 last-mentioned radicals is unsubstituted or substituted, D$^1$, D$^2$, D$^3$, D$^4$ and D$^5$ in each case independently of one another are hydrogen, (C$_1$–C$_6$)alkyl, aryl, aryl-(C$_1$–C$_6$)alkyl, (C$_3$–C$_9$)cycloalkyl or (C$_3$–C$_9$)cycloalkyl-(C$_1$–C$_6$)alkyl, where each of the 5 last-mentioned radicals is unsubstituted or substituted, or in each case two radicals D$^3$ of two groups —B$^3$—D$^3$ bound to one carbon atom are linked to each other and form an alkylene group having 2 to 4 carbon atoms which is unsubstituted or substituted by one or more radicals selected from the group consisting of (C$_1$–C$_4$)alkyl and (C$_1$–C$_4$)alkoxy, L$^O$ is a direct bond, oxygen, sulfur or a group NG$^{30}$ in which the radical G$^{30}$ is hydrogen, aryl which is unsubstituted or substituted, or (C$_3$–C$_9$)cycloalkyl which is unsubstituted or substituted, or heterocyclyl which is unsubstituted or substituted, or (C$_1$–C$_6$)alkyl, (C$_2$–C$_6$)alkenyl or (C$_2$–C$_6$)alkynyl, where each of the last-mentioned 3 radicals is unsubstituted or substituted by one or more radicals selected from the group consisting of halogen, hydroxyl, cyano, nitro, thiocyanato, (C$_1$–C$_4$)alkoxy, (C$_1$–C$_4$)haloalkoxy, (C$_2$–C$_4$)alkenyloxy, (C$_2$–C$_4$)haloalkenyloxy, (C$_1$–C$_4$)alkylthio, (C$_1$–C$_4$)alkylsulfinyl, (C$_1$–C$_4$)alkylsulfonyl, (C$_1$–C$_4$)haloalkylsulfinyl, (C$_1$–C$_4$)haloalkylsulfonyl, (C$_3$–C$_9$)cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'''—, where R', R" and R''' in each case independently of one another are hydrogen, (C$_1$–C$_6$)alkyl, aryl, aryl-(C$_1$–C$_6$)alkyl, (C$_3$–C$_9$)cycloalkyl or (C$_3$–C$_9$)cycloalkyl-(C$_1$–C$_6$)alkyl, where each of the 5 last-mentioned radicals is unsubstituted or substituted and where Z and Z' independently of one another are in each case an oxygen or sulfur atom, (X)n is n substituents X, where the X in each case independently of one another are halogen, hydroxyl, amino, nitro, formyl, carboxyl, cyano, thiocyanato, aminocarbonyl or (C$_1$–C$_6$)alkyl, (C$_1$–C$_6$)alkoxy, (C$_1$–C$_6$)alkylthio, mono(C$_1$–C$_6$)alkylamino, di(C$_1$–C$_4$)alkylamino, (C$_2$–C$_6$)alkenyl, (C$_2$–C$_6$)alkynyl, [(C$_1$–C$_6$)alkyl]carbonyl, [(C$_1$–C$_6$)alkoxy]carbonyl, mono-(C$_1$–C$_6$)alkylaminocarbonyl, di(C$_1$–C$_4$)alkylaminocarbonyl, N—(C$_1$–C$_6$)alkanoylamino or N—(C$_1$–C$_4$)alkanoyl-N—(C$_1$–C$_4$)alkylamino, where each of the last-mentioned 13 radicals is unsubstituted or substituted, or (C$_3$–C$_9$)cycloalkyl, (C$_3$–C$_9$)cycloalkoxy, (C$_3$–C$_9$)cycloalkylamino, phenyl, phenoxy, phenylthio, phenylcarbonyl, heterocyclyl, heterocyclyloxy, heterocyclylthio or heterocyclylamino, where each of the last-mentioned 11 radicals is unsubstituted or substituted, or two adjacent radicals X together are a fused cycle having 4 to 6 ring atoms which is carbocyclic or contains hetero ring atoms selected from the group consisting of O, S and N and which is unsubstituted or substituted by one or more radicals selected from the group consisting of halogen, (C$_1$–C$_4$)alkyl and oxo, n is 0, 1, 2, 3, 4 or 5 and heterocyclyl in the abovementioned radicals independently of one another in each case is a heterocyclic radical having 3 to 7 ring atoms and 1 to 3 hetero atoms selected from the group consisting of N, O and S.

2. A compound or a salt thereof as claimed n claim 1, wherein

R$^1$ is phenyl, phenoxy, phenylthio, phenylamino, N-phenyl-N-(C$_1$–C$_4$)alkylamino, where each of the last-mentioned 5 radicals is unsubstituted or substituted by one or more radicals selected from the group consisting of halogen, hydroxyl, amino, nitro, formyl, carboxyl, sulfo, cyano, thiocyanato, (C$_1$–C$_4$)alkyl, (C$_1$–C$_4$)haloalkyl, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl and (C$_1$–C$_4$)haloalkylsulfonyl and, inclusive of substituents, has 6 to 30 carbon atoms, or is (C$_3$–C$_9$)cycloalkyl which is unsubstituted or substituted by one or more radicals selected from the group consisting of halogen, hydroxyl, amino, cyano, thiocyanato, (C$_1$–C$_4$)alkyl, (C$_1$–C$_4$)haloalkyl, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino and di(C$_1$–C$_4$)alkylamino and, inclusive of substituents, has 3 to 30 carbon atoms, or is heterocyclyl which is unsubstituted or substituted by one or more radicals selected from the group consisting of halogen, hydroxyl, amino, nitro, formyl, carboxyl, sulfonyl, cyano, thiocyanato, (C$_1$–C$_4$)alkyl, (C$_1$–C$_4$)haloalkyl, (C$_1$–C$_4$)alkoxy, (C$_1$–C$_4$)haloalkoxy, (C$_1$–C$_4$)alkylthio, (C$_1$–C$_4$)haloalkylthio, mono-(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono-(C$_1$–C$_4$)

alkylaminocarbonyl, di($C_1$–$C_4$)alkylaminocarbonyl, ($C_1$–$C_4$)alkylsulfonyl and ($C_1$–$C_4$)haloalkylsulfonyl and, inclusive of substituents, has 2 to 30 carbon atoms, or is hydrogen or ($C_1$–$C_6$)alkyl, ($C_2$–$C_6$)alkenyl, (C2–6)alkynyl, ($C_1$–$C_6$)alkoxy or ($C_1$–$C_6$)alkylthio, where each of the last-mentioned 5 radicals is unsubstituted or substituted by one or more radicals selected form the group consisting of halogen, hydroxyl, cyano, nitro, thiocyanato, ($C_1$–$C_4$)alkoxy, ($C_1$–$C_4$)haloalkoxy, ($C_2$–$C_4$)alkenyloxy, ($C_2$–$C_4$)haloalkenyloxy, ($C_1$–$C_4$) alkylthio, ($C_1$–$C_4$)alkylsulfinyl, ($C_1$–$C_4$)alkylsulfonyl, ($C_1$–$C_4$)haloalkylsulfinyl, ($C_1$–$C_4$)haloalkylsulfonyl and ($C_3$–$C_6$)cycloalkyl, which is unsubstituted or substituted by one or more radicals selected from the group consisting of halogen, hydroxyl, amino, cyano, thiocyanato, ($C_1$–$C_4$)alkyl, ($C_1$–$C_4$)haloalkyl, ($C_1$–$C_4$) alkoxy, ($C_1$–$C_4$)haloalkoxy, ($C_1$–$C_4$)alkylthio, ($C_1$–$C_4$) haloalkylthio, mono-($C_1$–$C_4$)alkylamino and di($C_1$–$C_4$)alkylamino, and phyenyl and heterocyclyl, where each of the two last-mentioned radicals is unsubstituted or substituted by one or more radicals selected from the group consisting of halogen, hydroxyl, amino, nitro, formyl, carboxyl, sulfonyl, cyano, thiocyanato, ($C_1$–$C_4$)alkyl, ($C_1$–$C_4$) haloalkyl, ($C_1$–$C_4$)alkoxy, ($C_1$–$C_4$)haloalkoxy, ($C_1$–$C_4$) alkylthio, ($C_1$–$C_4$)haloalkylthio, mono($C_1$–$C_4$) alkylamino, di($C_1$–$C_4$)alkylamino, ($C_3$–$C_9$)cycloalkyl, [($C_1$–$C_4$)alkyl]carbonyl, [($C_1$–$C_4$)alkoxy]carbonyl, aminocarbonyl, mono-($C_1$–$C_4$)alkylaminocarbonyl, di($C_1$–$C_4$)alkylaminocarbonyl, ($C_1$–$C_4$)alkylsulfonyl and ($C_1$–$C_4$)haloalkylsulfonyl, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are ($C_1$–$C_4$) alkyl, phenyl, phenyl($C_1$–$C_4$)alkyl, ($C_3$–$C_6$)cycloalkyl or ($C_3$–$C_6$)cycloalkyl-($C_1$–$C_4$)alkyl, where each of the 5 last-mentioned radicals is unsubstituted or substituted by one or more radicals selected from the group consisting of halogen, hydroxyl, amino, nitro, formyl, cyano, thiocyanato, ($C_1$–$C_4$)alkoxy, ($C_1$–$C_4$)alkylthio, mono-($C_1$–$C_4$)alkylamino, di($C_1$–$C_4$)alkylamino, ($C_2$–$C_4$)alkenyl, ($C_2$–$C_4$)alkynyl, ($C_3$–$C_6$)cycloalkyl and, in the case of cyclic radicals, also ($C_1$–$C_4$)alkyl and ($C_1$–$C_4$)haloalkyl, and where Z and Z' independently of one another are in each case one oxygen or sulfur atom, and $R^2$ is ($C_3$–$C_9$)cycloalkyl which is unsubstituted or substituted by one or more radicals selected from the group consisting of the radicals A), B), C) and D), where group A) consists of the radicals halogen, hydroxyl, amino, nitro, formyl, carboxyl, aminocarbonyl, sulfo, cyano, thiocyanato and oxo group B) consists of the radicals ($C_1$–$C_6$)alkyl, ($C_1$–$C_6$) alkoxy, ($C_1$–$C_6$)alkylthio, mono($C_1$–$C_6$)alkylamino, di($C_1$–$C_4$)alkylamino, ($C_2$–$C_6$)alkenyl, ($C_2$–$C_6$) alkynyl, ($C_3$–$C_9$)cycloalkyl, ($C_4$–$C_9$)cycloalkenyl, ($C_1$–$C_6$)alkylidene, ($C_4$–$C_9$)cycloalkylidene, radicals of the formulae R'—C(=Z')—, R'—C(=Z')—Z—, R'Z—C(=Z')—, R'R"N—C(=Z')—, R'—Z—C(=Z')—O—, R'R"N—C(=Z')—Z—, R'Z—C(=Z')— NR"— and R'R"N—C(=Z')—NR'"—, where R', R" and R'" in each case independently of one another are hydrogen, ($C_1$–$C_6$)alkyl, phenyl, phenyl-($C_1$–$C_6$)alkyl, ($C_3$–$C_9$)cycloalkyl or ($C_3$–$C_9$) cycloalkyl-($C_1$–$C_6$)alkyl and where Z and Z' independently of one another are in each case an oxygen or sulfur atom, group C) consists of radicals as defined for group B), but where each radical is substituted by one or more radicals selected from the group consisting of halogen, hydroxyl, amino, nitro, formyl, carboxyl, sulfo, cyano, thiocyanato, ($C_1$–$C_4$)alkoxy, ($C_1$–$C_4$) haloalkoxy, ($C_1$–$C_4$)alkylthio, ($C_1$–$C_4$)haloalkylthio, mono($C_1$–$C_4$)alkylamino, di($C_1$–$C_4$)alkylamino, ($C_3$–$C_9$)cycloalkyl, ($C_4$–$C_9$)cycloalkylene, ($C_4$–$C_9$) cycloalkylidene, [($C_1$–$C_4$)alkyl]carbonyl, [($C_1$–$C_4$) alkoxy]carbonyl, aminocarbonyl, mono($C_1$–$C_4$) alkylaminocarbonyl, di($C_1$–$C_4$)alkylaminocarbonyl, phenyl, phenoxy, phenylthio, phenylcarbonyl, heterocyclyl, heterocyclyloxy, heterocyclylthio and heterocyclylamino, where each of the last-mentioned 21 radicals is unsubstituted or substituted by one or more radicals selected from the group consisting of halogen, nitro, cyano, ($C_1$–$C_4$)alkoxy, ($C_1$–$C_4$)alkylthio, ($C_1$–$C_4$)haloalkoxy, formyl, ($C_1$–$C_4$) alkylcarbonyl and ($C_1$–$C_4$)alkoxycarbonyl and, in the case of cyclic radicals, also ($C_1$–$C_4$)alkyl, ($C_1$–$C_4$)haloalkyl and ($C_1$–$C_6$)alkylidene, and, in the case of cyclic radicals, also ($C_1$–$C_6$)alkyl, ($C_1$–$C_6$)haloalkyl and ($C_1$–$C_6$)alkylidene, and group D) consists of divalent or trivalent aliphatic bridges having 1 to 6 carbon atoms which, in the case of divalent bridges, connect two and, in the case of trivalent bridges, three carbon atoms of the cyclic skeleton and the radical $R^2$ thus constitutes the radical of a bicyclic or tricyclic system, where each of the bridges is unsubstituted or substituted by one or more substituents selected from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$)haloalkoxy, formyl, ($C_1$–$C_4$)alkylcarbonyl, ($C_1$–$C_4$)alkoxycarbonyl and oxo, and where $R^2$, inclusive of substituents, has 3 to 20 carbon atoms, or $R^2$ is ($C_4$–$C_9$)cycloalkenyl which is unsubstituted or substituted by one or more radicals selected from the group consisting of the radicals A), B), C) and D) as are defined as radicals for the case where $R^2$=($C_3$–$C_9$) cycloalkyl and, in this context, inclusive of substituents has 4 to 20 carbon atoms, or $R^2$ is heterocyclyl which is unsubstituted or substituted by one or more radicals selected from the group consisting of the radicals A), B), C) and D) as are defined as radicals for the case where $R^2$($C_3$–$C_9$)cycloalkyl, or $R^2$ is phenyl which is unsubstituted or substituted by one or more radicals selected from the group consisting of the radicals A), B) and C) as are defined as radicals for $R^2$=($C_3$–$C_9$)cycloalkyl, where R2 inclusive of substituents has up to 20 carbon atoms.

3. A compound or a salt thereof as claimed in claim 1, wherein $R^3$ is a radical of the formula

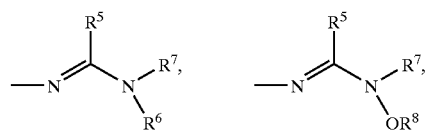

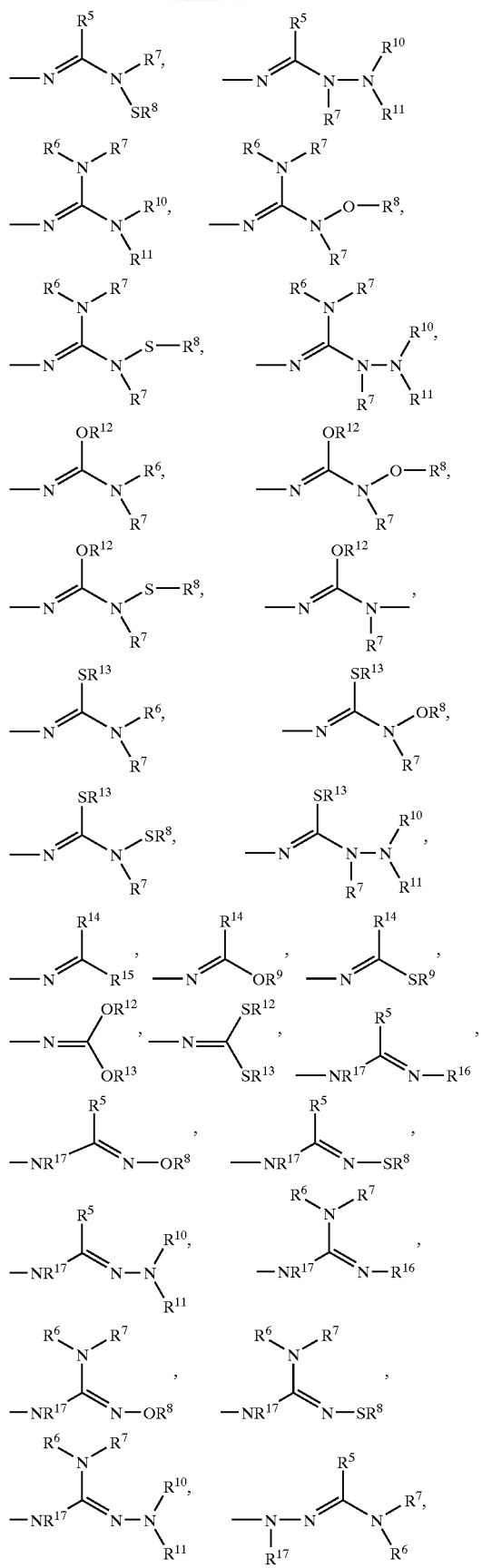

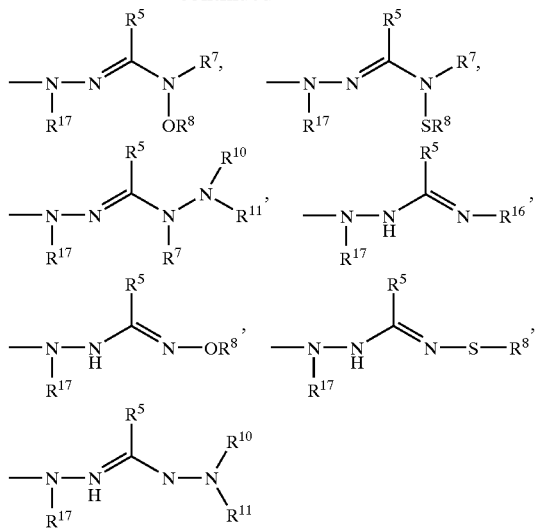

where $R^6$ and $R^7$ together with the nitrogen atom of the group $NR^6R^7$, $R^7$ and $OR^8$ together with the nitrogen atom of the group $NOR^8R^7$, $R^7$ and $SR^8$ together with the nitrogen atom of the group $NSR^8R^7$, $R^{10}$ and $R^{11}$ together with the nitrogen atom of the group $NR^{10 11}$, $OR^{12}$ and $OR^{13}$, or $SR^{12}$ and $SR^{13}$, together with the carbon atom of the groups of the formulae

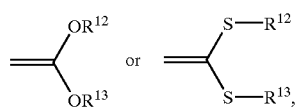

respectively, $OR^9$ and $R^{14}$ or $SR^9$ and $R^{14}$ together with the carbon atom of the groups

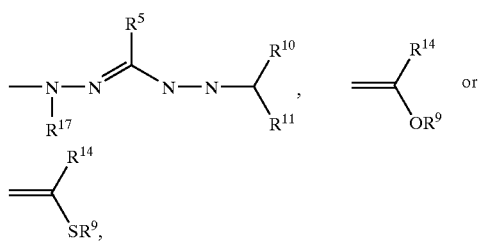

respectively, $R^{14}$ and $R^{15}$ together with the carbon atom of the group

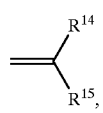

$R^5$ and $R^7$ together with the atom group

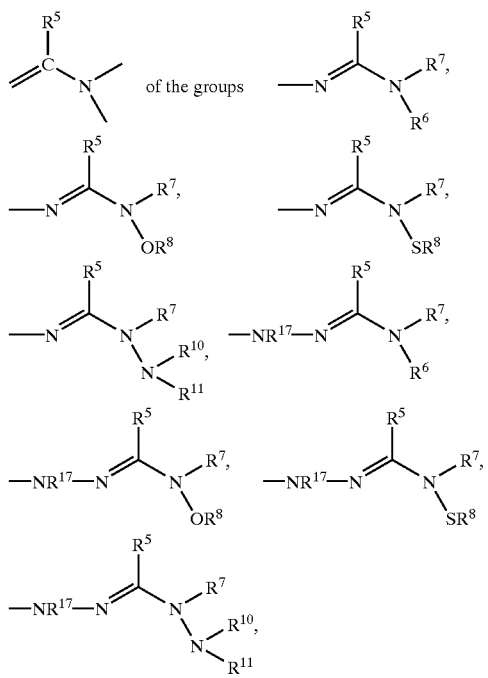

of the groups $R^5$ and $R^{17}$ together with the carbon atom of the group

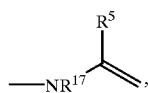

$R^5$ and $R^{16}$ together with the atom group

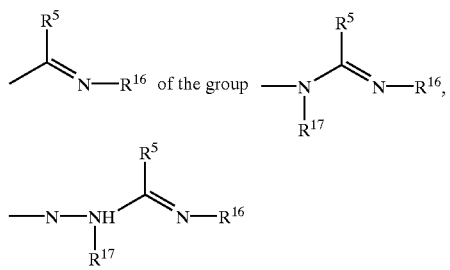

$R^7$ and $R^{10}$ together with the atom group

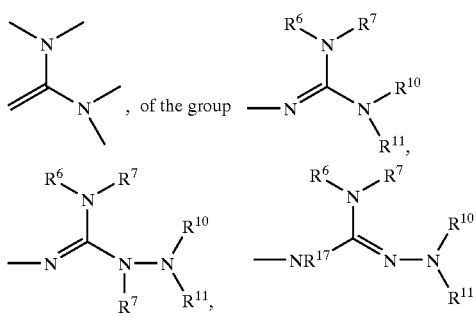

of the group in each case independently of one another form a carbocyclic or heterocyclic ring having 3 to 7 ring atoms and 1 to 6 hetero atoms, the optional further hetero ring atoms being selected from the group consisting of N, O and S and the carbocyclic or heterocyclic ring in each case being unsubstituted or substituted, and the radicals $R^5$, $R^6$, $R^7$, $R^8$, $R^9$, $R^{10}$, $R^{11}$, $R^{14}$ $R^{15}$, $R^{16}$, $R^{17}$ in the above formulae independently of one another are hydrogen, aryl which is unsubstituted or substituted, or $(C_3-C_9)$cycloalkyl which is unsubstituted or substituted, or heterocyclyl which is unsubstituted or substituted, or $(C_1-C_6)$alkyl, $(C_2-C_6)$alkenyl or $(C_2-C_6)$alkynyl, where each of the last-mentioned 3 radicals is unsubstituted or substituted by one or more radicals selected from the group consisting of halogen, hydroxyl, cyano, nitro, thiocyanato, $(C_1-C_4)$alkoxy, haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"—, where R', R" and R'" in each case independently of one another are hydrogen, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted, and where Z and Z' independently of one another are in each case an oxygen or sulfur atom, and $R^{12}$, $R^{13}$ in each case independently of one another are aryl which is unsubstituted or substituted, or $(C_3-C_9)$cycloalkyl which is unsubstituted or substituted, or heterocyclyl which is substituted, or $(C_1-C_6)$alkyl, $(C_2-C_6)$alkenyl or $(C_2-C_6)$alkynyl, where each of the last-mentioned 3 radicals is unsubstituted or substituted by one or more radicals selected form the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, $(C_3-C_9)$cycloalkyl which is unsubstituted or substituted, phenyl which is unsubstituted or substituted, heterocyclyl which is unsubstituted or substituted, and radicals of the formulae R'—C(=Z')—, R'—C(=Z')—Z—, R'—Z—C(=Z')—, R'R"N—C(=Z')—O—, R'R"N—C(=Z')—Z—, R'Z—C(=Z')—NR"— and R'R"N—C(=Z')—NR'"—, where R', R" and R'" in each case independently of one another are hydrogen $(C_1-C_6)$alkyl, aryl, aryl $(C_1-C_6)$alkyl, $(C_3-C_9)$cycloalkyl or $(C_3-C_9)$cycloalkyl-$(C_1-C_6)$alkyl, where each of the 5 last-mentioned radicals is unsubstituted or substituted, and where Z and Z' independently of one another are in each case an oxygen or sulfur atom.

4. A compound or a salt thereof as claimed in claim 1, wherein $R^4$ is hydrogen, $(C_1-C_4)$alkyl, phenyl or $(C_3-C_6)$cycloalkyl, where each of the 3 last-mentioned radicals is unsubstituted or substituted by one or more radicals selected from the group consisting of halogen, hydroxyl, amino, nitro, formyl, carboxyl, sulfonyl, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, or is formyl, $[(C_1-C_4)$alkyl]carbonyl, $[(C_1-C_4)$alkoxy]carbonyl, aminocarbonyl, mono$(C_1-C_4)$alkylaminocarbonyl or di$(C_1-C_4)$alkylaminocarbonyl; and $L^o$ is a direct bond or oxygen, $A^1$ is straight-chain alkylene having 1 to 5 carbon atoms or straight-chain alkenylene or alkynylene having in each case 2 to 5 carbon atoms, where each of the three last-mentioned diradicals is unsubstituted or substituted by one or more radicals selected from the group consisting of halogen, nitro, cyano, thiocyanato and a radical of the formula —$B^2$—$D^2$, in which $B^2$ is a direct bond or a divalent group of the formulae —O—, —$SO_2$—, —CO—, —O—CO—, —$NR^O$—, —$NR^O$—CO—, —CO—$NR^O$—, —O—CO—$NR^O$— or —$NR^O$—CO—O—, in which $R^O$ independently of one another are in each case hydrogen, $(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, where each of the last-mentioned 5 radicals is unsubstituted or substituted by one or more radicals selected from the group consisting of halogen, hydroxyl, amino, nitro, formyl, carboxyl, sulfonyl, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, $A^2$ is a direct bond or a group of the formula —$CH_2$—, —$CH_2CH_2$—, —$CH_2CH_2CH_2$— or —$CH_2CH_2CH_2CH_2$—, where each of the 4 last-mentioned diradicals is unsubstituted or substituted by one or more radicals selected form the group consisting of halogen, nitro, cyano, thiocyanato and radicals of the formula —$B^3$—$D^3$, or a divalent radical of the formula $V^1$, $V^2$, $V^3$, $V^4$ or $V^5$,

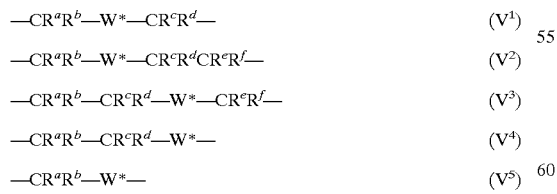

—$CR^aR^b$—$W^*$—$CR^cR^d$— (V¹)

—$CR^aR^b$—$W^*$—$CR^cR^d CR^eR^f$— (V²)

—$CR^aR^b$—$CR^cR^d$—$W^*$—$CR^eR^f$— (V³)

—$CR^aR^b$—$CR^cR^d$—$W^*$— (V⁴)

—$CR^aR^b$—$W^*$— (V⁵)

where each of the radicals $R^a$ to $R^f$ in each case independently of one other is hydrogen, halogen, nitro, cyano, thiocyanato or a radical of the formula —$B^4$—$D^4$, $W^*$ is in each case O, S or a group of the formula $N(B^5$—$D^5)$, and $B^5$ is a direct bond or a divalent group of the formulae —C(=Z*)—, —C(=Z*)—Z**—, —C(=Z*)—NH— or —C(=Z*)—NR*—, where Z*=O or S, Z**=O or S and R*=$(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, where each of the 5 last-mentioned radicals is unsubstituted or substituted, $B^2$, $B^3$ and $B^4$ in each case independently of one another are a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —$NR^O$—, —$NR^O$—O—, —$NR^O$—CO—, —CO—$NR^O$—, —CO—$NR^O$—, —O—CO—$NR^O$— or —$NR^O$—CO—O—, where p is the integer 0, 1 or 2 and $R^O$ is hydrogen, $(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, where each of the 5 last-mentioned radicals is unsubstituted or substituted by one or more radicals selected from the group consisting of halogen, hydroxyl, amino, nitro, formyl, carboxyl, sulfo, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and, in the case of cyclic radicals, also $(C_1-C_4)$alkyl and $(C_1-C_4)$haloalkyl, and $D^2$, $D^3$, $D^4$ and $D^5$ independently of one another are hydrogen, $(C_1-C_6)$alkyl, phenyl, phenyl-$(C_1-C_4)$alkyl, $(C_3-C_6)$cycloalkyl-$(C_3-C_6)$alkyl, where each of the 5 last-mentioned radicals is unsubstituted or substituted.

5. A compound or a salt thereof as claimed in claim 1, wherein (X)n is n substituents X, where X preferably in each case independently of one another are halogen, hydroxyl, amino, nitro, formyl, carboxyl, cyano, thiocyanato, aminocarbonyl or $(C_1-C_4)$alkyl, $(C_1-C_4)$alkoxy, $(C_1-C_4)$alkylthio, mono$(C_1-C_4)$alkylamino, di$(C_1-C_4)$alkylamino, $(C_2-C_4)$alkenyl, $(C_2-C_4)$alkynyl, $[(C_1-C_4)$alkyl]carbonyl, $[(C_1-C_4)$alkoxy]carbonyl, mono$(C_1-C_4)$alkylaminocarbonyl, di$(C_1-C_4)$alkylaminocarbonyl, N—$(C_1-C_6)$alkanoylamino or N—$(C_1-C_4)$alkanoyl-N—$(C_1-C_4)$alkylamino, where each of the last-mentioned 13 radicals unsubstituted or substituted by one or more radicals selected form the group consisting of halogen, hydroxyl, amino, cyano, thiocyanato, $(C_1-C_4)$alkoxy, $(C_1-C_4)$haloalkoxy, $(C_1-C_4)$alkylthio, mono$(C_1-C_4)$alkylamino, di$(C_1-C_4)$alkylamino, $(C_3-C_6)$cycloalkyl, $(C_3-C_6)$cycloalkylamino, $[(C_1-C_4)$alkyl]carbonyl, $[(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, where each of the last-mentioned 8 radicals is unsubstituted or has one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl and $(C_1-C_4)$alkoxycarbonyl, or is $(C_3-C_9)$cycloalkyl, phenyl, phenoxy, phenylthio, phenylcarbonyl, heterocyclyl, heterocyclyloxy, heterocyclylthio or heterocyclylamino, where each of the last-mentioned 9 radicals is unsubstituted or substituted by one or more radicals selected from the group consisting of halogen, hydroxyl, amino, nitro, formyl, carboxyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, $[(C_1-C_4)$alkyl]carbonyl, $[(C_1-C_4)$alkoxy]carbonyl, aminocarbonyl, mono$(C_1-C_4)$alkylaminocarbonyl and di$(C_1-C_4)$alkylaminocarbonyl, or two adjacent radicals X together are a fused cycle having 4 to 6 ring atoms which is carbocyclic or contains hetero ring atoms selected from the group consisting of O, S and N and which is unsubstituted or substituted by one or more radicals selected form the group consisting of halogen, $(C_1-C_4)$alkyl and oxo, and n is o, 1, 2 or 3.

6. A process for the preparation of a compound of the formula (I) or a salt thereof as defined in claim 1,

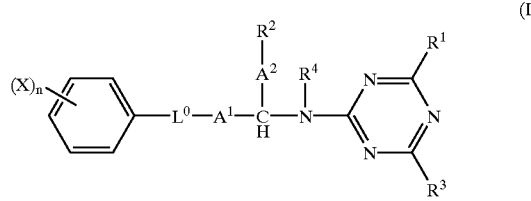
(I)

where $A^1$, $A^2$, $L^0$, $R^1$, $R^2$, $R^3$, $R^4$, X and n are as defined in formula (I) in claim 1, wherein a) in the event that $R^3$ in formula (I) is a group of the formula $-L^1-N=C(U^1)(U^3)$, where $L^1$, $U^1$ and $U^3$ are as defined under $R^3$ in formula (I), a compound of the formula (II)

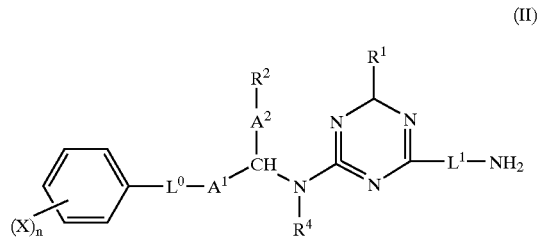
(II)

where $A^1$, $A^2$, $L^0$, $L^1$, $R^1$, $R^2$, $R^4$, X and n are as defined in formula (I), is reacted with a compound of the formula (III)

(III)

where $U^1$ and $U^3$ are as defined in formula (I) and $R^{18}$ and $R^{19}$ independently of one another are unsubstituted or substituted alkyl having up to 12 carbon atoms, or jointly linked are an alkylene group having 2 to 4 carbon atoms, or b) in the event that $R^3$ in formula (I) is a group of the formula $L^1-NG^1-C(U^2)=N-U^4$ where $L^1$, $G^1$, $U^2$ and $U^4$ are as defined under $R^3$ in formula (I), a compound of the formula (IV)

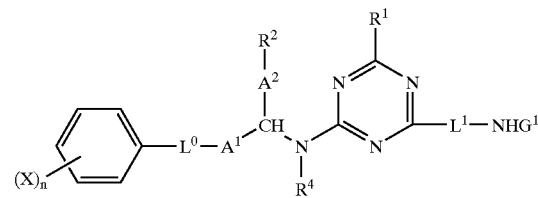
(IV)

where $A^1$, $A^2$, $L^0$, $L^1$, $R^1$, $R^2$, $R^4$, $G^1$, X and n are as defined in formula (I) in claim 1 is reacted with a compound of the formula (V)

(V)

where $U^2$ and $U^4$ are as defined in formula (I) and $R^{18}$ is as defined in formula (III) in variant a) of the present claim, or c) in the event that $R^3$ in formula (I) is a group of the formula $-L^1-N=C(U^1)(U^3)$ where $U^3$ $=NG^{18}NG^{19}G^{20}$, $NG^{21}OG^{22}$ or $NG^{23}SG^{24}$ and $L^1$, $U^1$, $G^{18}$, $G^{19}$, $G^{20}$, $G^{21}$, $G^{22}$, $G^{23}$, $G^{24}$ are as defined under $R^3$ in formula (I), a compound of the formula (VI)

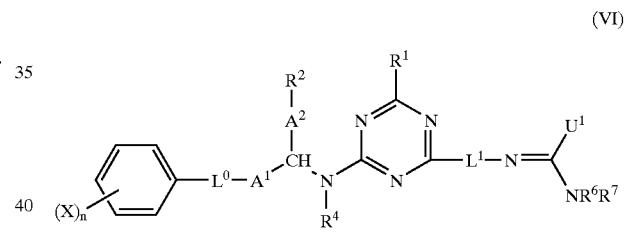
(VI)

where $A^1$, $A^2$, $L^0$, $L^1$, $R^1$, $R^2$, $R^4$, $U^1$, X and n are as defined in formula (I) and $R^6$ and $R^7$ are as defined under $R^3$ in formula (I) are reacted with a compound of the formula (VII) or its acid adducts

$H-U^3$ (VII)

where $U^3$ is as defined in formula (I), or d) in the event that $R^3$ in formula (I) is a group of the formula $-L^1-N=C(U^1)(U^3)$ where $U^1=R^{14}$ and $U^3=R^{15}$ and where $L^1$, $R^{14}$ and $R^{15}$ are as defined under $R^3$ in claim 3, a compound of the formula (II) as defined in variant a) of the present claim is reacted with an aldehyde or ketone of the formula (VIII)

$U^1-CO-U^3$ (VIII)

where $U^1$ and $U^3$ are as defined in formula (I).

7. A herbicidal or plant-growth-regulating composition, which comprises one or more compounds of the formula (I) or their salts as claimed in claims 1 and formulation auxiliaries applicable in crop protection.

8. A method of controlling harmful plants or for regulating the growth of plants, which comprises applying an active amount of one or more compounds of the formula (I) or their salts as claimed in claim 1 to the plants, plant seeds or the area under cultivation.

9. The method according to claim 8, wherein the compounds of the formula (I) or their salts are employed for controlling harmful plants or for regulating the growth of crops of useful plants or ornamentals.

* * * * *